(12) United States Patent
Bedian et al.

(10) Patent No.: US 10,329,345 B2
(45) Date of Patent: *Jun. 25, 2019

(54) STABILIZED ANGIOPOIETIN-2 ANTIBODIES AND USES THEREOF

(71) Applicant: MedImmune Limited, Cambridge (GB)

(72) Inventors: Vahe Bedian, Framingham, MA (US); William Dall'Acqua, Gaithersburg, MD (US); Herren Wu, Gaithersburg, MD (US); Michael Bowen, Rockville, MD (US); Jeffrey Brown, Waltham, MA (US); Ralph Minter, Cambridge (GB); Andrew Buchanan, Cambridge (GB)

(73) Assignee: MedImmune Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/335,610

(22) Filed: Oct. 27, 2016

(65) Prior Publication Data

US 2017/0174756 A1 Jun. 22, 2017

Related U.S. Application Data

(60) Division of application No. 13/932,485, filed on Jul. 1, 2013, now abandoned, which is a continuation of application No. 12/864,544, filed as application No. PCT/US2009/032224 on Jan. 28, 2009, now Pat. No. 8,507,656.

(60) Provisional application No. 61/023,958, filed on Jan. 28, 2008, provisional application No. 61/100,063, filed on Sep. 25, 2008, provisional application No. 61/142,778, filed on Jan. 6, 2009.

(51) Int. Cl.
| | |
|---|---|
| *A61K 39/00* | (2006.01) |
| *C07K 16/22* | (2006.01) |
| *A61K 39/395* | (2006.01) |
| *A61K 31/282* | (2006.01) |
| *A61K 31/4375* | (2006.01) |
| *A61K 31/513* | (2006.01) |
| *A61K 31/519* | (2006.01) |
| *A61K 31/7068* | (2006.01) |
| *A61K 38/17* | (2006.01) |
| *A61K 31/337* | (2006.01) |
| *A61K 31/4745* | (2006.01) |
| *A61K 31/496* | (2006.01) |
| *A61K 31/573* | (2006.01) |

(52) U.S. Cl.
CPC .......... *C07K 16/22* (2013.01); *A61K 31/282* (2013.01); *A61K 31/337* (2013.01); *A61K 31/4375* (2013.01); *A61K 31/4745* (2013.01); *A61K 31/496* (2013.01); *A61K 31/513* (2013.01); *A61K 31/519* (2013.01); *A61K 31/573* (2013.01); *A61K 31/7068* (2013.01); *A61K 38/1793* (2013.01); *A61K 39/3955* (2013.01); *A61K 39/39558* (2013.01); *A61K 39/39591* (2013.01); *A61K 2039/505* (2013.01); *C07K 2317/21* (2013.01); *C07K 2317/56* (2013.01); *C07K 2317/73* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,650,490 | A | 7/1997 | Davis et al. |
| 5,814,464 | A | 9/1998 | Davis et al. |
| 6,166,185 | A | 12/2000 | Davis et al. |
| 6,455,035 | B1 | 9/2002 | Suri et al. |
| 7,067,475 | B2 | 6/2006 | Cerretti et al. |
| 7,205,275 | B2 | 4/2007 | Oliner |
| 7,485,297 | B2 | 2/2009 | Wood et al. |
| 7,521,053 | B2 | 4/2009 | Oliner |
| 7,658,924 | B2 | 2/2010 | Oliner et al. |
| 2003/0124129 | A1 | 7/2003 | Oliner |
| 2006/0018909 | A1 | 1/2006 | Oliner et al. |
| 2006/0057138 | A1 | 3/2006 | Wood et al. |
| 2006/0079564 | A1 | 4/2006 | Jansen et al. |

FOREIGN PATENT DOCUMENTS

| | | |
|---|---|---|
| EP | 0784683 B1 | 2/2001 |
| EP | 1165115 B1 | 5/2003 |
| EP | 0821728 B1 | 8/2004 |
| WO | WO 96/031598 | 10/1996 |
| WO | WO 00/75323 A1 | 12/2000 |
| WO | WO 03/030833 | 4/2003 |
| WO | WO 2006/068953 A2 | 6/2006 |
| WO | WO 2007/075323 | 7/2007 |
| WO | WO 2007/109254 A2 | 9/2007 |
| WO | WO 2007/134050 A2 | 11/2007 |
| WO | WO 2009/097352 A2 | 8/2009 |
| WO | WO 2011/014469 A1 | 2/2011 |

OTHER PUBLICATIONS

Ahmad, Syed A. et al., 2001, "The Effects of Angiopoietin-1 and -2 on Tumor Growth and Angiogenesis in Human Colon Cancer", Cancer Research, 61:1255-1259.
Ahmad, Syed A. et al., 2001, "Differential Expression of Angiopoietin-1 and Angiopoietin-2 in Colon Carcinoma", Cancer, 92:1138-1143.
Asahara, Takayuki et al., 1998, "Tie2 Receptor Ligands, Angiopoietin-1 and Angiopoietin-2, Modulate VEGF-Induced Postnatal Neovascularization", Circ. Res. 83:233-240.
Buchanan Declaration for European Patent No. 1838733 B1 filed Oct. 9, 2013.

(Continued)

*Primary Examiner* — Brad Duffy

(57) ABSTRACT

Stabilized antibodies directed to Angiopoeitin-2 and uses of such antibodies are described. Nucleic acid and amino acid sequences, hybridomas or other cell lines for expressing such antibodies are also provided.

15 Claims, 39 Drawing Sheets

Specification includes a Sequence Listing.

(56) References Cited

OTHER PUBLICATIONS

Buchanan Declaration for European Patent No. 1838733 B1 filed Dec. 5, 2013.

Buchanan et al., 2013, "Engineering a therapeutic IgG molecule to address cysteinylation, aggregation and enhance thermal stability and expression", mAbs 5:2, 255-262.

Brown, Jeffrey L. Et al. 2010, "A Human Monoclonal Anti-ANG2 Antibody Leads to Broad Antitumor Activity in Combination with VEGF Inhibitors and Chemotherapy Agents ini Preclinical Models", Mol. Cancer Ther., 9(1):145-156.

Bunone, Giuseppe et al., 1999, "Expression of Angiogenesis Stimulators and Inhibitors in Human Thyroid Tumors and Correlation with Clinical Pathological Features", American Journal of Pathology, 155(6):1967-1976.

Cai, Mingqing, et al., 2003, "Single chain Fv antibody against angiopoietin-2 inhibits VEGF-induced endothelial cell proliferation and migration in vitro", Biochemical and Biophysical Research Communications, 309:946-951.

Chen, Yvonne et al., 1999, "Selection and Analysis of an Optimized Anti-VEGF Antibody: Crystal Structure of an Affinity-matured Fab in Complex with Antigen", J. Mol. Biol., 293:865-881.

Chen, L. et al., 2001, "Expression of angiopoietin-2 gene and its receptor Tie2 in hepatocellular carcinoma", J. Tongji Med. Univ., 21(3):228-230, 235. English Abstract Only.

Chowdhury, Partha S. et al., 1999, "Improving antibody affinity by mimicking somatic hypermutation in vitro", Nature Biotechnology, 17:568-572.

Davis, Samuel et al., 1996, "Isolation of Angiopoietin-1, a Ligand for the TIE2 Receptor, by Secretion-Trap Expression Cloning", Cell, 87:1161-1169.

Dumont, Daniel J., et al., 1994, "Dominant-negative and targeted null mutations in the endothelial receptor tyrosine kinase, tek, reveal a critical role in vasculogenesis of the embryo", Genes & Development, 8:1897-1909.

Etoh, Tsuyoshi et al., 2001, "Angiopoietin-2 Is Related to Tumor Angiogenesis in Gastric Carcinoma: Possible in Vivo Regulation via Induction of Proteases", Cancer Research, 61:2145-2153.

European Search Report for European Patent Application No. 10185152.5 dated Jan. 13, 2011.

Flessner, Michael F. et al., 2005, "Resistance of Tumor Interstitial Pressure to the Penetration of Intraperitoneally Delivered Antibodies into Metastatic Ovarian Tumors", Clin Cancer Res., 11(8):3117-3125.

Fiedler, Ulrike et al., 2003, "Angiopoietin-1 and Angiopoietin-2 Share the Same Binding Domains in the Tie-2 Receptor Involving the First Ig-like Loop and the Epidermal Growth Factor-like Repeats", The Journal of Biological Chemistry 278(3):1721-1727.

Gale, Nicholas W. et al., 2002, "Angiopoietin-2 Is Required for Postnatal Angiogenesis and Lymphatic Patterning, and Only the Latter Role Is Rescued by Angiopoietin-1", Developmental Cell, 3:411-423.

Gura, Trisha, 1997, "Systems for Identifying New Drugs Are Often Faulty", Science, 278:1041-1042.

Hanahan, Douglas, 1997, "Signaling Vascular Morphogenesis and Maintenance", Science, 277 (5322):48-50.

Holash, J. et al., 1999, Vessel Cooption, Regression, and Growth in Tumors Mediated by Angiopoietins and VEGF, Science, 284:1994-1998.

Holash, J. et al., 1999, "New model of tumor angiogenesis: dynamic balance between vessel regression and growth mediated by angiopoietins and VEGF", Oncogene, 18:5356-5362.

Hudson, Peter J., 1998, "Recombinant antibody fragments", Current Opinion in Biotechnology, 9:395-402.

Interlocutory Decison in Opposition for European Patent No. 05 854 387.7 dated Jan. 17, 2014.

International Preliminary Report on Patentability for PCT/US2005/045657 dated Jul. 10, 2007.

Jain, Rakesh K. 1990, "Physiological Barriers to Delivery of Monoclonal Antibodies and Other Macromolecules in Tumors", Cancer Research, 50:814s-819s.

Kim, Injune et al., 1999, "Molecular cloning and characterization of a novel angiopoietin family protein, angiopoietin-3", FEBS Letters 443:353-356.

Kim, Injune et al., 1999, "Molecular Cloning, Expression, and Characterization of Angiopoietin-related Protein", The Journal of Biological Chemistry, 274(37):26523-26528.

Kim, Injune et al., 2000, "Angiopoietin-2 at high concentration can enhance endothelial cell survival through the phosphatidylinositol 3'-kinase/Akt signal transduction pathway", Oncogene, 19:4549-4552.

Koga, Kazunari et al., 2001, "Expression of Angiopoietin-2 in Human Glioma Cells and Its Role for Angiogenesis", Cancer Research 61:6248-6254.

Korff, Thomas et al., 2001, "Blood vessel maturation in a 3-dimensional spheroidal coculture model: direct contact with smooth muscle cells regulates endothelial cell quiescence and abrogates VEGF responsiveness", The FASEB Journal, 15:447-457.

Kwak, Hee Jin et al., 1999, "Angiopoietin-1 is an apoptosis survival factor for endothelial cells", FEBS Letters, 448:249-253.

Lee, Ji Hee et al., 2001, "Comparative study of angiostatic and anti-invasive gene expressions as prognostic factors in gastric cancer", International Journal of Oncology, 18:355-361.

Leow, Ching Ching et al., 2012, "MEDI3617, a human anti-Angiopoietin 2 monoclonal antibody, inhibits angiogenesis and tumor growh in human xenograft models", International Journal of Oncology, 40:1321-1330.

Lewis, Claire E. et al., 2007, "Tie2-Expressing Monocytes and Tumor Angiogenesis: Regulation by Hypoxia and Angiopoietin-2", Cancer Research, 67(18):8429-8432.

Lin, Pengnian et al., 1997, "Inhibition of Tumor Angiogenesis Using a Soluable Receptor Establishes a Role for Tie2 in Pathologic Vascular Growth", The American Society for Clinical Investigation, Inc., 100(8):2072-2078.

Lin, Pengnian et al., 1998, "Antiangiogenic gene therapy targeting the endothelium-specific receptor tyrosine kinase Tie2", Proc. Natl. Acad. Sci. USA, 95:8829-8834.

Lobov, Ivan B. et al., 2002, "Angiopoietin-2 displays VEGF-dependent modulation of capillary structure and endothelial cell survival in vivo:", Proc. Natl. Acad. Sci. USA, 99:11205-11210.

Maisonpierre, Peter C.et al., 1997, "Angiopoietin-2, a Natural Antagonist for Tie2 That Disrupts in vivo Angiogenesis", Science, 277:55-60.

Mochizuki, Yasushi et al., 2002, "Angiopoietin 2 stimulates migration and tube-like structure formation of murine brain capillary endothelial cells through c-Fes and c-Fyn", Journal of Cell Science, 115:175-183.

Oliner et al., 2004, "Peptide-Fc Protein Expression", Cancer Cell, Cancer Cell Supplemental Data.

Oliner, Jonathan et al., 2004, "Suppression of angiogenesis and tumor growth by selective inhibition of angiopoietin-2", Cancer Cell, 6:507-516.

Opposition for EP 05854387.7 filed May 23, 2012.

Opponent Appeal EP 05854387.7 filed May 26, 2014.

Osada, Hideo, et al., 2001, "Gene expression of angiogenesis related factors in glioma", International Journal of Oncology, 18:305-309.

Reichmann, Lutz et al., 1988, "Reshaping human antibodies for therapy", Nature, 332:324-327.

Robinson, Candy S. et al., 2001, "The Effects of Angiopoietin-2 and Neutralizing Anti-Tie-2 Antibody on Microvessel Growth, Branching, and Regression in the Ex Vivo Rat Aortic Ring Explant Model of Angiogenesis", Proceedings of the American Association for Cancer Research, vol. 42, Abstract.

Rudikoff, Stuart et al., 1982, "Single amino acid substitution altering antigen-binding specificity", Proc. Natl. Acad. Sci. USA, 79:1979-1983.

Sato, Thomas N., et al., 1995, "Distinct roles of the receptor tyrosine kinases Tie-1 and Tie-2 in blood vessel formation", Nature, 376:70-74.

Shim, Winston S.N. et al., 2007, "Angiopoietin: A TIE(d) Balance in Tumor Angiogenesis", Mol. Cancer Research, 5(7):655-665.

(56) References Cited

OTHER PUBLICATIONS

Sfiligoi, Christian et al., 2003, "Angiopoietin-2 Expression in Breast Cancer Correlates With Lymph Node Invasion and Short Survival", Int. J. Cancer, 103:466-474.

Siemeister, Gerhard et al., 1999, "Two Independent Mechanisms Essential for Tumor Angiogenesis: Inhibition of Human Melanoma Xenograft Growth by Interfering with either the Vascular Endothelial Growth Factor Receptor Pathway or the Tie-2 Pathway", Cancer Research, 59:3185-3191.

Spinelli, Gian Paolo et al., 2006, "Long-Term Survival in Metastatic Pancreatic Cancer", Journal of the Pancreas, 7(5):486-491.

Supplementary European Search Report corresponding to EP 09706411 dated Oct. 4, 2012.

Suri, Chitra et al., 1998, "Increased Vascularization in Mice Overexpressing Angiopoietin-1", Science, 282:468-71.

Tanaka, Shinji et al., 1999, "Biologic significance of angiopoietin-2 expression in human hepatocellular carcinoma", The Journal of Clinical Investigation, 103(3):341-345.

Tanaka, Fumihiro et al., 2002, "Expression of Angiopoietins and Its Clinical Significance in Non-Small Cell Lung Cancer", Cancer Research, 62:7124-7129.

Teichert-Kuliszewska, Krystyna et al., 2001, "Biological action of angiopoietin-2 in a fibrin matrix model of angiogenesis is associated with activation of Tie2", Cardiovascular Research 49:659-670.

Thurston, G. et al., 1999, "Leakage-Resistant Blood Vessels in Mice Transgenically Overexpressing Angiopoietin-1", Science, 286:2511-2514.

Thurston, G. et al., 2000, "Angiopoietin-1 protects the adult vasculature against plasma leakage", 6(4):460-463.

Vajkoczy, Peter et al., 2002, "Microtumor growth initiates angiogenic sprouting with simultaneous expression of VEGF, VEGF receptor-2, and angiopoietin-2", The Journal of Clinical Investigation, 109(6):777-785.

Wong, Maria Pik et al., 2000, "The angiopoietins, tie2 and vascular endothlial growth factor are differently expressed in the transformation of normal lung to non-small cell lung carcinomas", Lung Cancer 29:11-12/.

Wurmbach, Jan-Henner et al., 2000, "The Expression of Angiopoietins and their Receptor Tie-2 in Human Prostate Carcinoma", Anticancer Research, 20:5217-5220.

Yancopoulos, George D. et al., 2000, "Vascular-specific growth factors and blood vessel formation", Nature, 407:242-248.

Zagzag, David et al., 1999, "In Situ Expression of Angiopoietins in Astrocytomas Identifies Angiopoietin-2 as an Early Marker of Tumor Angiogenesis", Experimental Neurology, 159:391-400.

Buchanan Declaration for European Patent No. 1838733 B1 filed Oct. 19, 2014.

Leow, Ching Ching et al., 2012, "MEDI3617, a human anti-Angiopoietin 2 monoclonal antibody, inhibits angiogenesis and tumor growth in human tumor xenograft models", International Journal of Oncology, 40:1321-1330.

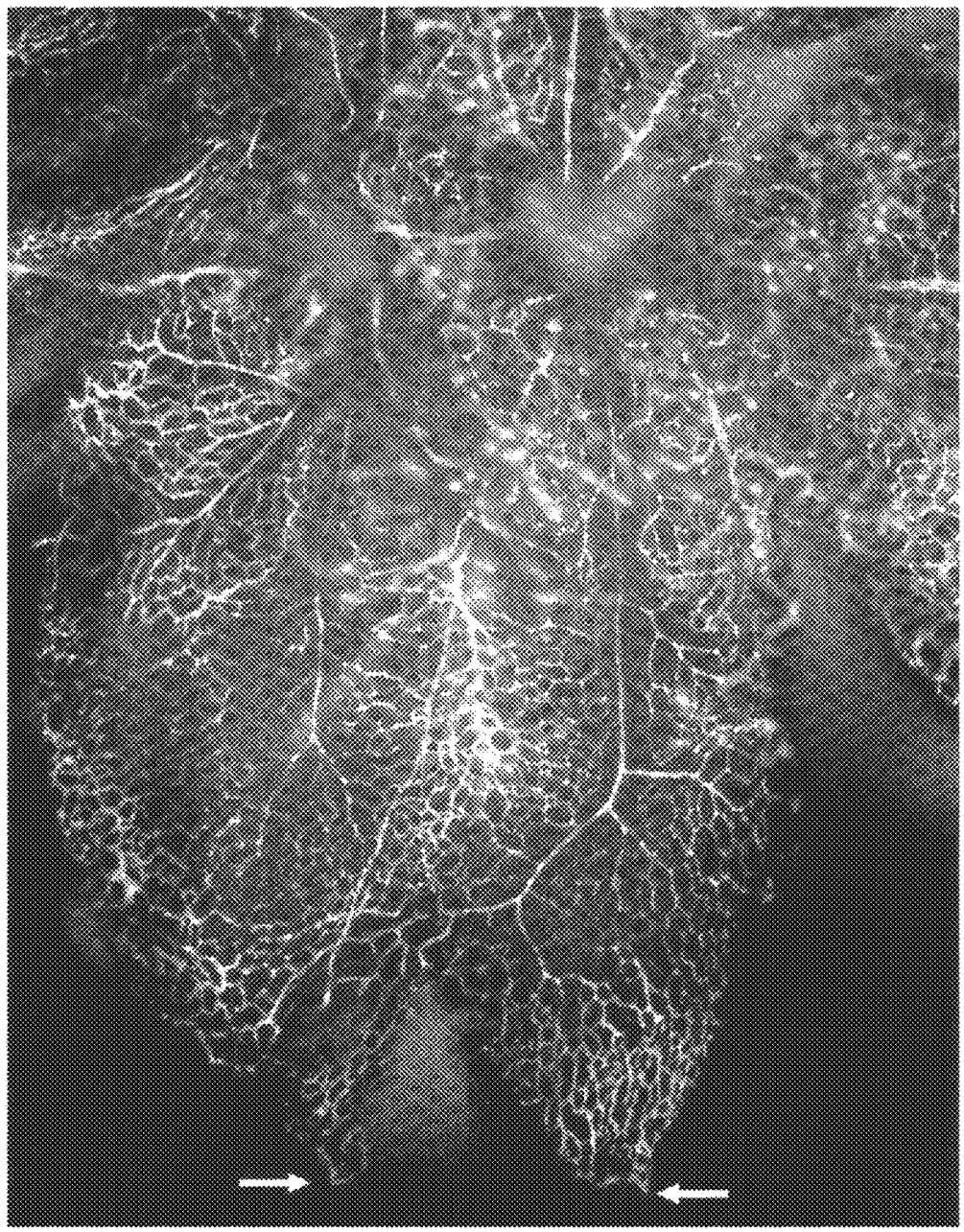

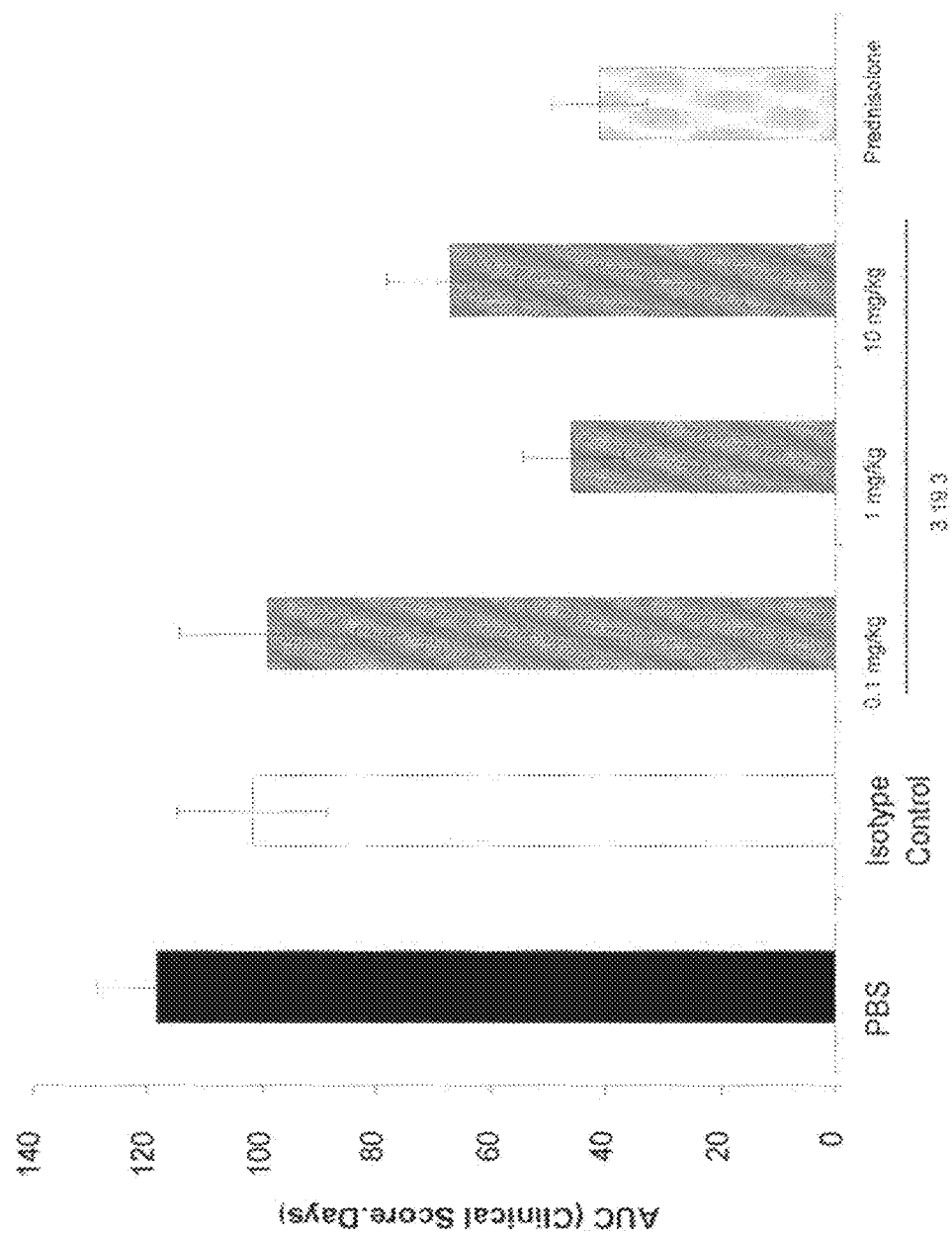

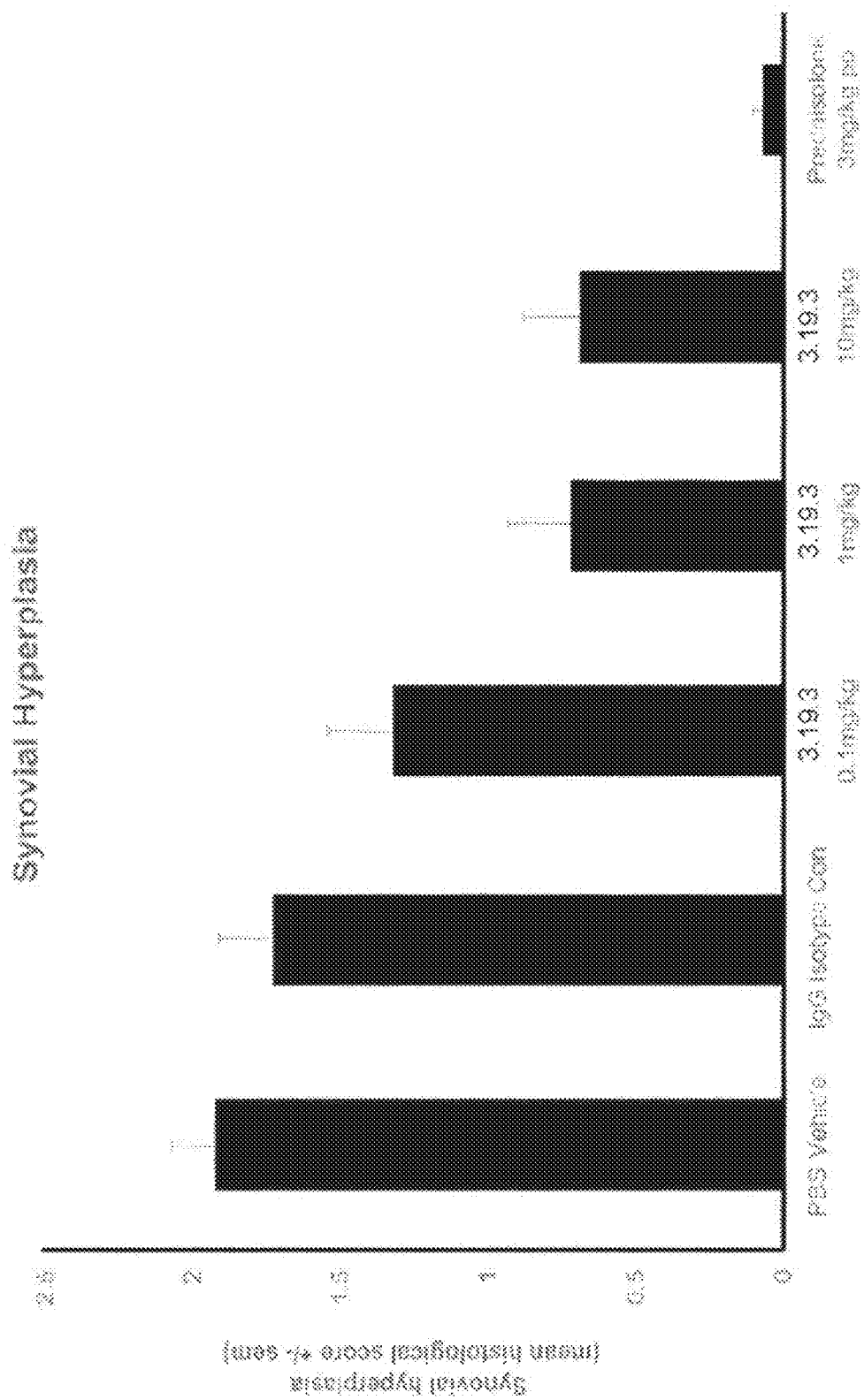

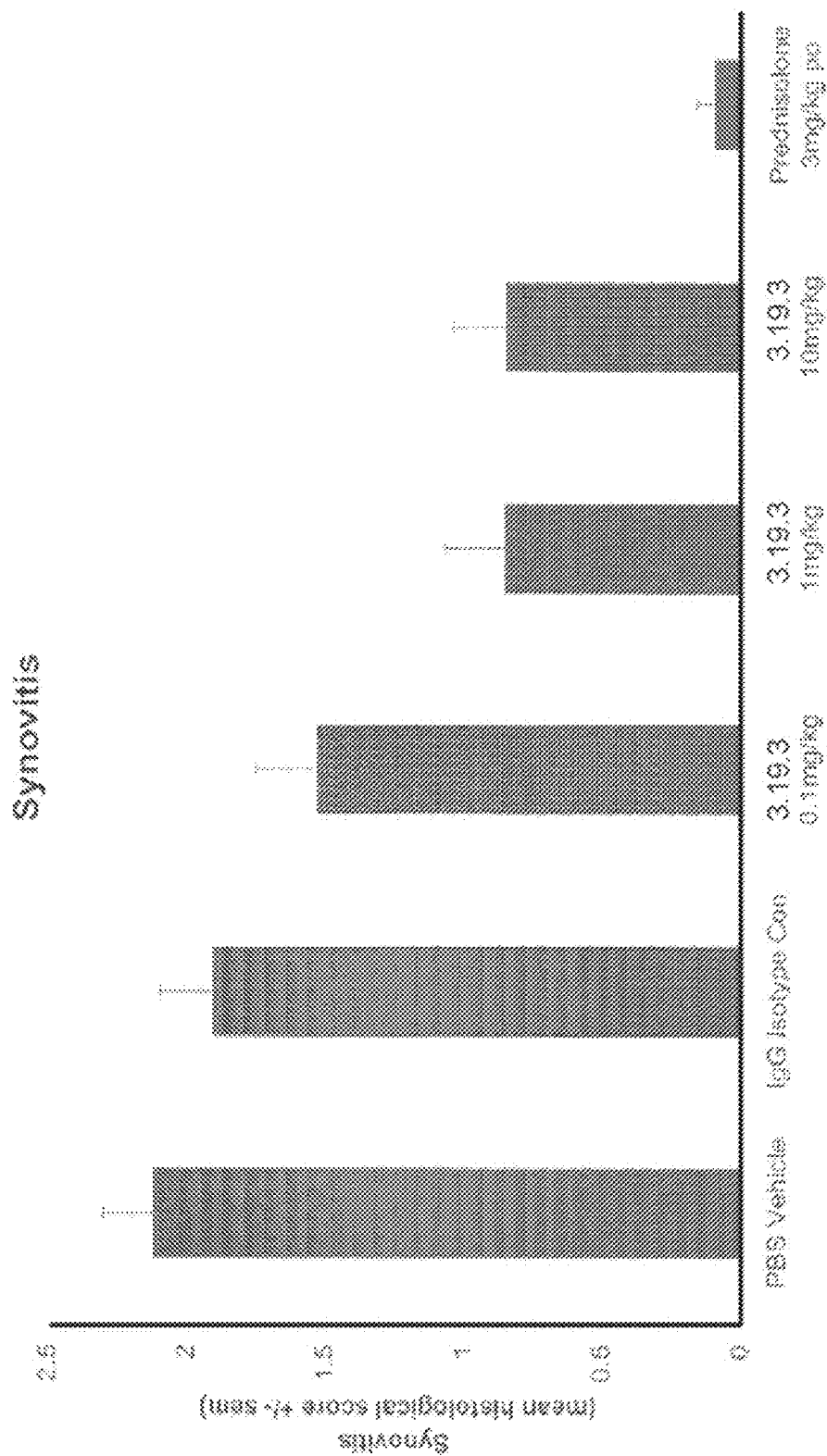

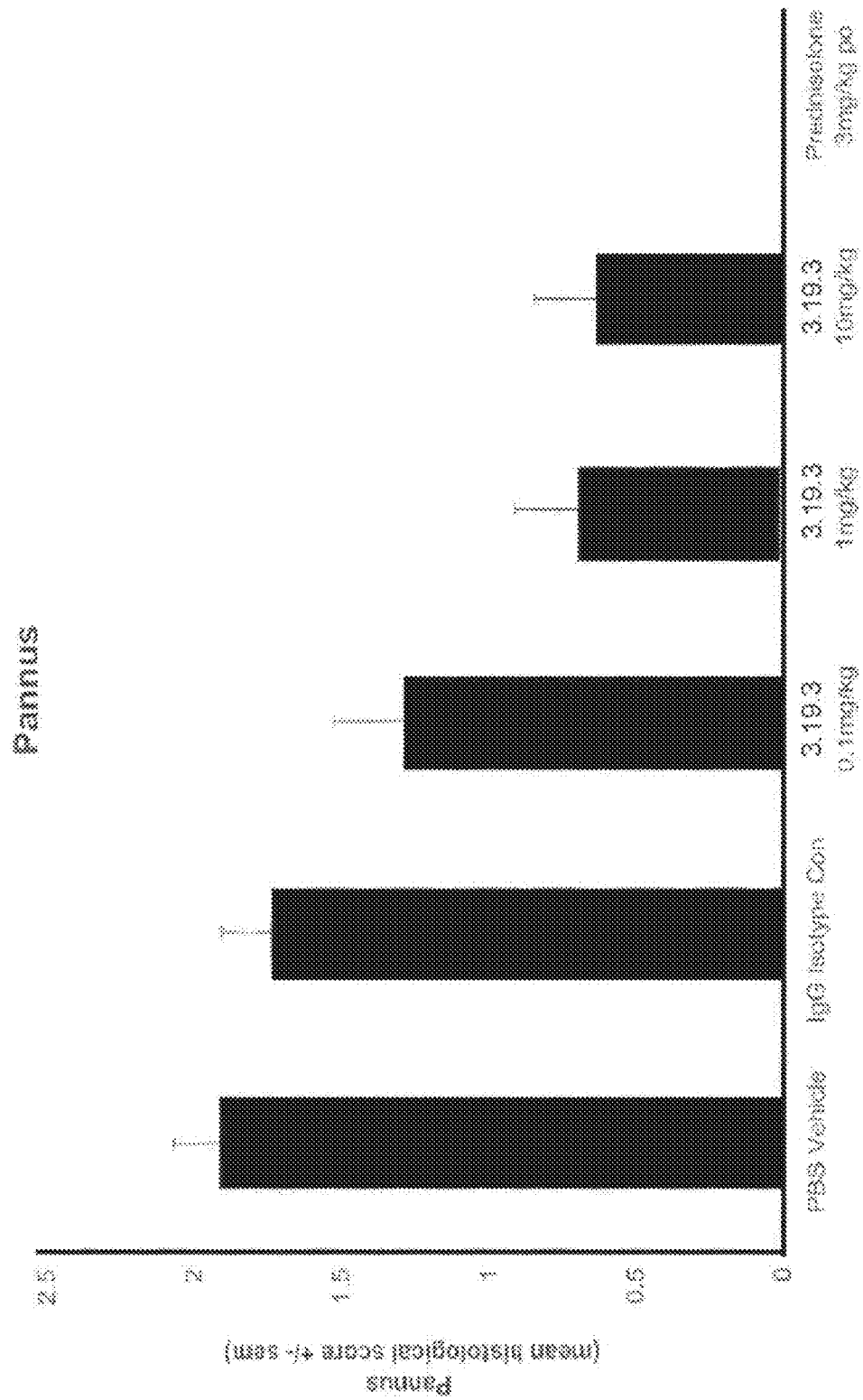

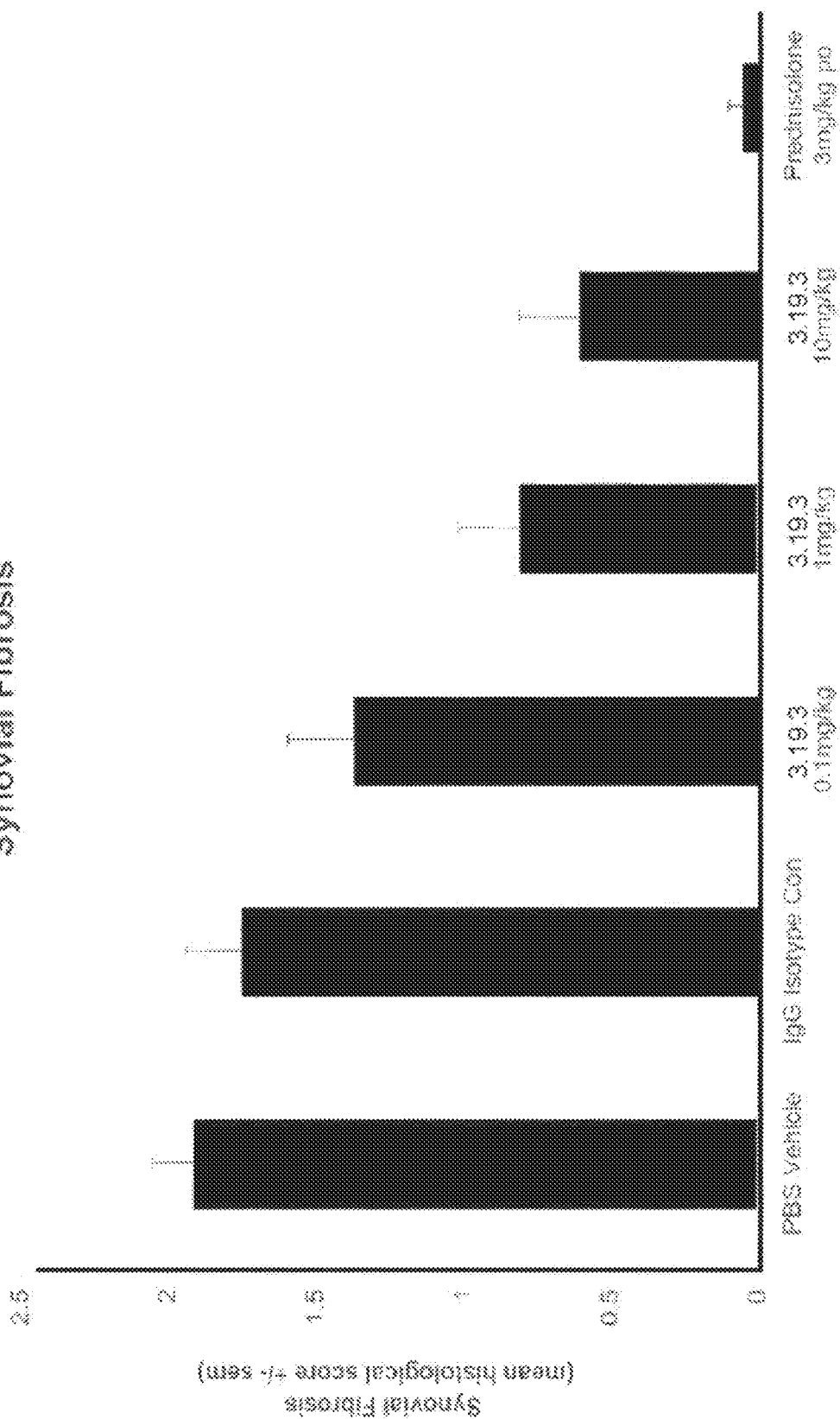

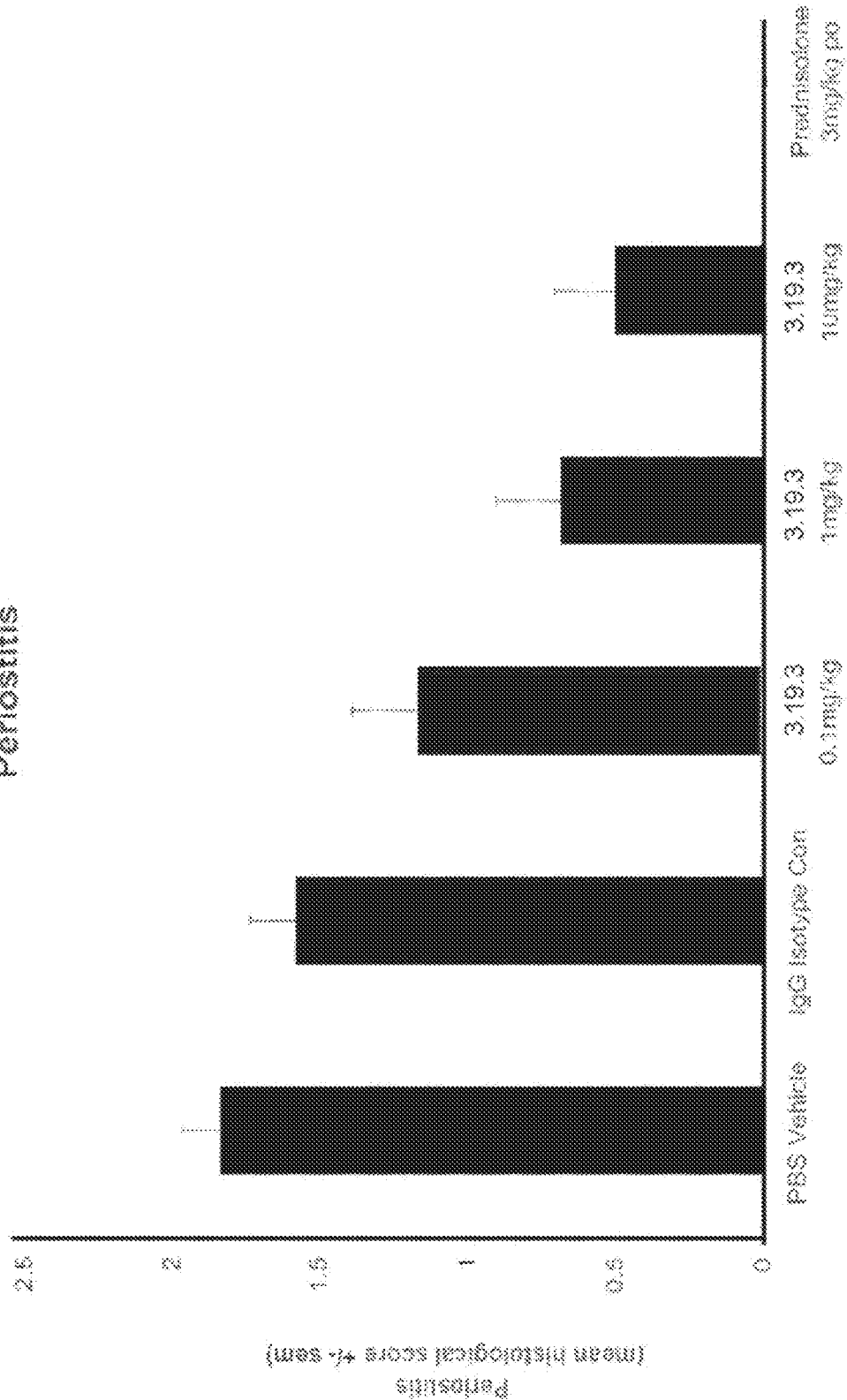

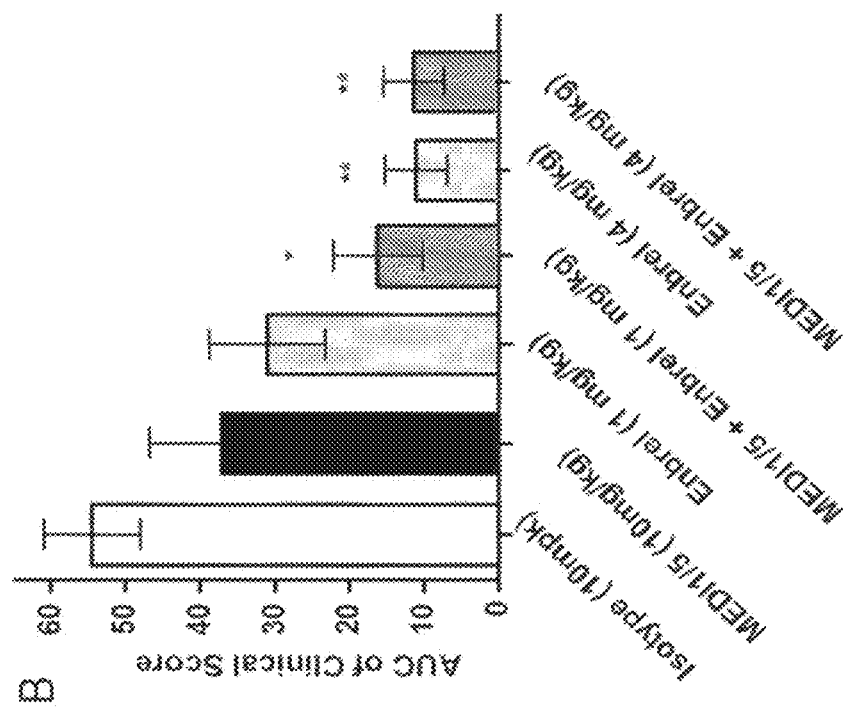
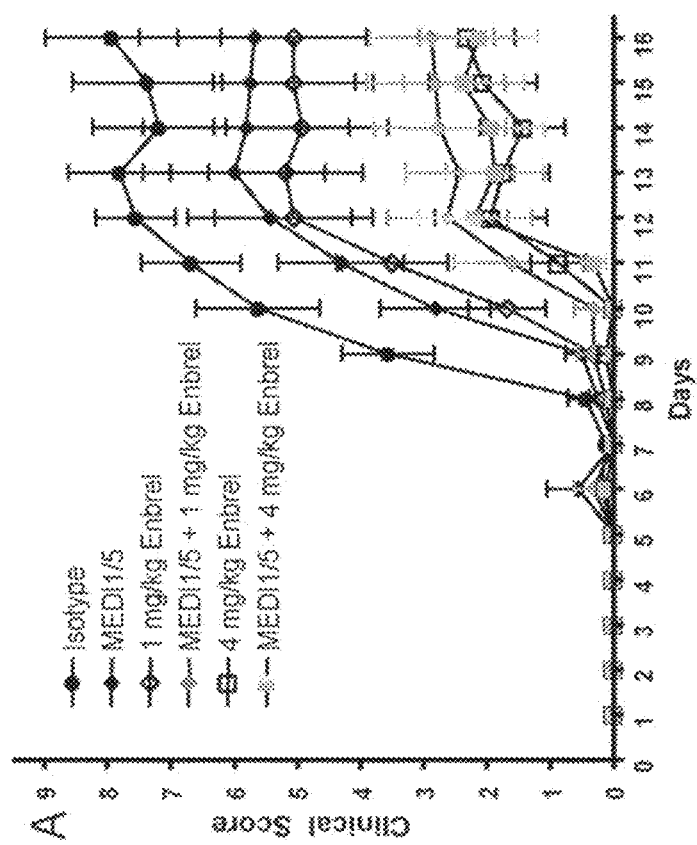
FIG. 16A
FIG. 16B

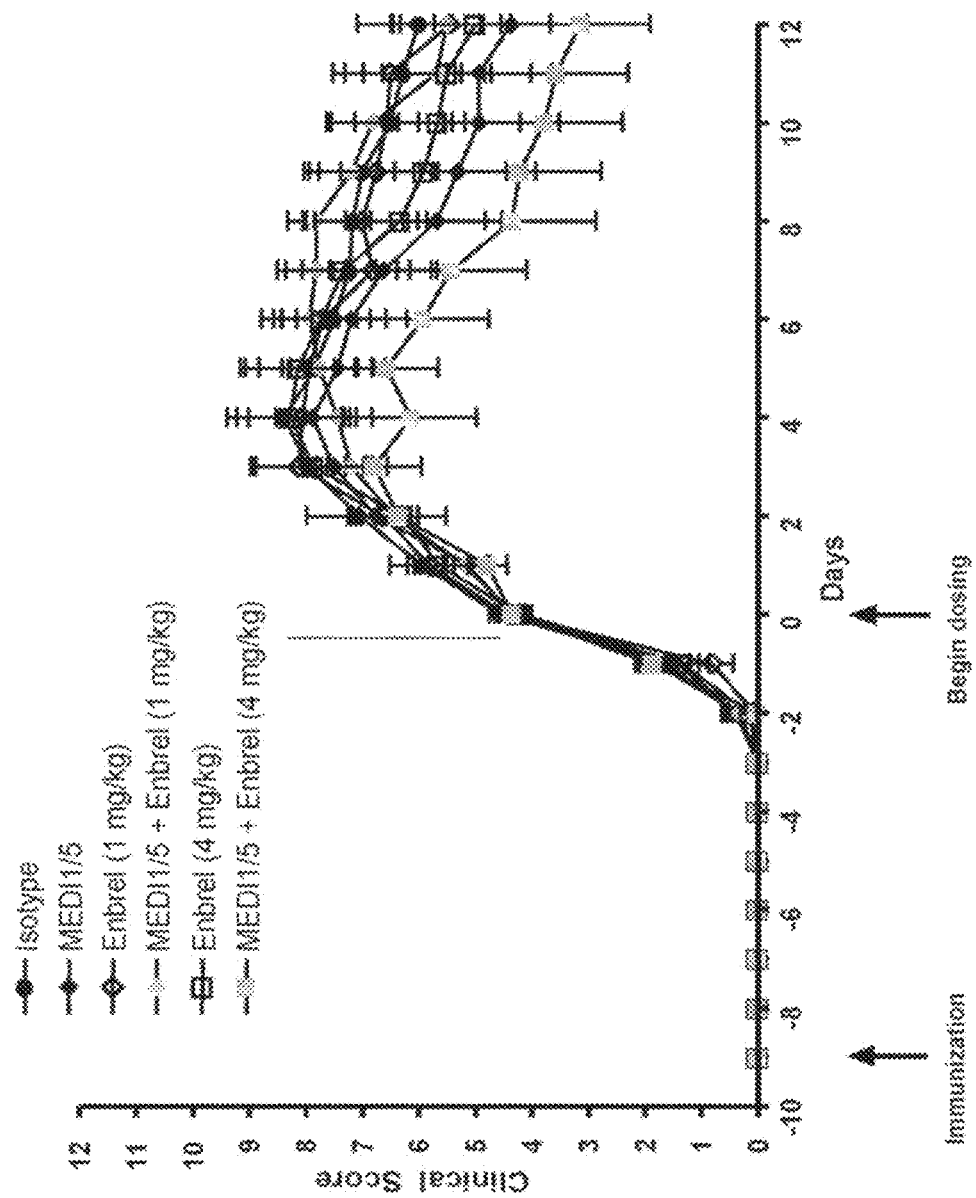

STABILIZED ANGIOPOIETIN-2 ANTIBODIES AND USES THEREOF

CROSS REFERENCE TO RELATED APPLICATIONS

This application is a divisional of U.S. application Ser. No. 13/932,485, filed on Jul. 1, 2013. U.S. application Ser. No. 13/932,485 is a continuation of U.S. application Ser. No. 12/864,544 filed on Nov. 3, 2010, now U.S. Pat. No. 8,507,656, issued on Aug. 13, 2016. U.S. application Ser. No. 12/864,544 is a U.S. national stage application of International Application No. PCT/US2009/032224 filed on Jan. 28, 2009 which claims benefit under 35 U.S.C. § 119(e) to the following U.S. Provisional Application Nos. 61/023, 958 filed Jan. 28, 2008, 61/100,063 filed on Sep. 25, 2008, and 61/142,778 filed on Jan. 6, 2009. Each of the above listed applications is incorporated by reference herein in its entirety for all purposes.

REFERENCE TO THE SEQUENCE LISTING

This application incorporates by reference a Sequence Listing submitted with this application as text file entitled ANGST100USDIV_sequence_listing created on Oct. 24, 2016 and having a size of 14 kilobytes.

FIELD

The invention relates to stabilized monoclonal antibodies against Angiopoietin-2 (Ang-2) and uses of such antibodies. Aspects of the invention also relate to hybridomas or other cell lines expressing such antibodies. The described antibodies are useful as diagnostics and for the treatment of diseases associated with the activity of Ang-2 and/or Ang-1.

BACKGROUND

Angiogenesis is the process of forming new capillaries from preexisting blood vessels and is an essential component of embryogenesis, normal physiological growth, repair, and tumor expansion. Although a variety of factors can modulate endothelial cell (EC) responses in vitro and blood vessel growth in vivo, only vascular endothelial growth factor (VEGF) family members and the angiopoietins are believed to act almost exclusively on vascular ECs (Yancopoulos et al., *Nature* 407:242-48 (2000)).

The angiopoietins were discovered as ligands for the Ties, a family of tyrosine kinases that is selectively expressed within the vascular endothelium (Yancopoulos et al., *Nature* 407:242-48 (2000)). There are now four definitive members of the angiopoietin family: Angiopoietin-3 and -4 (Ang-3 and Ang-4) may represent widely diverged counterparts of the same gene locus in mouse and man (Kim et al., *FEBS Let,* 443:353-56 (1999); Kim et al., *J Biol Chem* 274:26523-28 (1999)). Ang-1 and Ang-2 were originally identified in tissue culture experiments as agonist and antagonist, respectively (Davis et al., *Cell* 87:1161-69 (1996); Maisonpierre et al., *Science* 277:55-60 (1997)). All of the known angiopoietins bind primarily to Tie2, and both Ang-1 and -2 bind to Tie2 with an affinity of 3 nM (Kd) (Maisonpierre et al., *Science* 277:55-60 (1997)). Ang-1 was shown to support EC survival and to promote endothelium integrity, (Davis et al., *Cell* 87:1161-69 (1996); Kwak et al., *FEBS Lett* 448:249-53 (1999); Suri et al., *Science* 282:468-71 (1998); Thurston et al., *Science* 286: 2511-14 (1999); Thurston et al., *Nat. Med.* 6:460-63 (2000)), whereas Ang-2 had the opposite effect and promoted blood vessel destabilization and regression in the absence of the survival factors VEGF or basic fibroblast growth factor (Maisonpierre et al., *Science* 277:55-60 (1997)). However, many studies of Ang-2 function have suggested a more complex situation. Ang-2 might be a complex regulator of vascular remodeling that plays a role in both vessel sprouting and vessel regression. Supporting such roles for Ang-2, expression analyses reveal that Ang-2 is rapidly induced, together with VEGF, in adult settings of angiogenic sprouting, whereas Ang-2 is induced in the absence of VEGF in settings of vascular regression (Holash et al., *Science* 284:1994-98 (1999); Holash et al., *Oncogene* 18:5356-62 (1999)). Consistent with a context-dependent role, Ang-2 binds to the same endothelial-specific receptor, Tie-2, which is activated by Ang-1, but has context-dependent effects on its activation (Maisonpierre et al., *Science* 277:55-60 (1997)).

Corneal angiogenesis assays have shown that both Ang-1 and Ang-2 had similar effects, acting synergistically with VEGF to promote growth of new blood vessels (Asahara et al., *Circ. Res.* 83:233-40 (1998)). The possibility that there was a dose-dependent endothelial response was raised by the observation that in vitro at high concentration, Ang-2 can also be pro-angiogenic (Kim et al., *Oncogene* 19:4549-52 (2000)). At high concentration, Ang-2 acts as an apoptosis survival factor for endothelial cells during serum deprivation apoptosis through activation of Tie2 via PI-3 kinase and Akt pathway (Kim et al., *Oncogene* 19:4549-52 (2000)).

Other in vitro experiments suggested that during sustained exposure, the effects of Ang-2 may progressively shift from that of an antagonist to an agonist of Tie2, and at later time points, it may contribute directly to vascular tube formation and neovessel stabilization (Teichert-Kuliszewska et al., *Cardiovasc. Res.* 49:659-70 (2001)). Furthermore, if ECs were cultivated on fibrin gel, activation of Tie2 with Ang-2 was also observed, perhaps suggesting that the action of Ang-2 could depend on EC differentiation state (Teichert-Kuliszewska et al., *Cardiovasc. Res.* 49:659-70 (2001)). In microvascular EC cultured in a three-dimensional collagen gel, Ang-2 can also induce Tie2 activation and promote formation of capillary-like structures (Mochizuki et al., *J. Cell. Sci.* 115:175-83 (2002)). Use of a 3-D spheroidal coculture as an in vitro model of vessel maturation demonstrated that direct contact between ECs and mesenchymal cells abrogates responsiveness to VEGF, whereas the presence of VEGF and Ang-2 induced sprouting (Korff et al., *Faseb J.* 15:447-57 (2001)). Etoh et al. demonstrated that ECs that constitutively express Tie2, the expression of MMP-1, -9 and u-PA were strongly up-regulated by Ang-2 in the presence of VEGF (Etoh, et al., *Cancer Res.* 61:2145-53 (2001)). With an in vivo pupillary membrane model, Lobov et al. showed that Ang-2 in the presence of endogenous VEGF promotes a rapid increase in capillary diameter, remodeling of the basal lamina, proliferation and migration of endothelial cells, and stimulates sprouting of new blood vessels (Lobov et al., *Proc. Natl. Acad. Sci. USA* 99:11205-10 (2002)). By contrast, Ang-2 promotes endothelial cell death and vessel regression without endogenous VEGF (Lobov et al., *Proc. Natl. Acad. Sci. USA* 99:11205-10 (2002)). Similarly, with an in vivo tumor model, Vajkoczy et al. demonstrated that multicellular aggregates initiate vascular growth by angiogenic sprouting via the simultaneous expression of VEGFR-2 and Ang-2 by host and tumor endothelium (Vajkoczy et al., *J. Clin. Invest.* 109:777-85 (2002)). This model illustrated that the established microvasculature of growing tumors is characterized by a continuous remodeling, putatively mediated by the expression of VEGF and Ang-2.

Knock-out mouse studies of Tie-2 and Angiopoietin-1 show similar phenotypes and suggest that Angiopoietin-1 stimulated Tie-2 phosphorylation mediates remodeling and stabilization of developing vessel, promoting blood vessel maturation during angiogenesis and maintenance of endothelial cell-support cell adhesion (Dumont et al., *Genes & Development*, 8:1897-1909 (1994); Sato, *Nature*, 376:70-74 (1995); (Thurston, G. et al., 2000 Nature Medicine: 6, 460-463)). The role of Angiopoietin-1 is thought to be conserved in the adult, where it is expressed widely and constitutively (Hanahan, *Science*, 277:48-50 (1997); Zagzag, et al., *Exp Neurology*, 159:391-400 (1999)). In contrast, Angiopoietin-2 expression is primarily limited to sites of vascular remodeling where it is thought to block the constitutive stabilizing or maturing function of Angiopoietin-1, allowing vessels to revert to, and remain in, a plastic state which may be more responsive to sprouting signals (Hanahan, 1997; Holash et al., *Oncogene* 18:5356-62 (1999); Maisonpierre, 1997). Studies of Angiopoietin-2 expression in pathological angiogenesis have found many tumor types to show vascular Angiopoietin-2 expression (Maisonpierre et al., *Science* 277:55-60 (1997)). Functional studies suggest Angiopoietin-2 is involved in tumor angiogenesis and associate Angiopoietin-2 overexpression with increased tumor growth in a mouse xenograft model (Ahmad, et al., *Cancer Res.*, 61:1255-1259 (2001)). Other studies have associated Angiopoietin-2 overexpression with tumor hypervascularity (Etoh, et al., *Cancer Res.* 61:2145-53 (2001); Tanaka et al., *Cancer Res.* 62:7124-29 (2002)).

In recent years Angiopoietin-1, Angiopoietin-2 and/or Tie-2 have been proposed as possible anti-cancer therapeutic targets (See, for example, U.S. Pat. Nos. 6,166,185, 5,650,490, 5,814,464, US Patent Publication No. 20060018909 and PCT publication Nos. WO2006/068953 and WO2007/068895).

Ang-2 is expressed during development at sites where blood vessel remodeling is occurring (Maisonpierre et al., *Science* 277:55-60 (1997)). In adult individuals, Ang-2 expression is restricted to sites of vascular remodeling as well as in highly vascularized tumors, including glioma (Osada et al., *Int. J. Oncol.* 18:305-09 (2001); Koga et al., *Cancer Res.* 61:6248-54 (2001)), hepatocellular carcinoma, (Tanaka et al, *J. Clin. Invest.* 103:341-45 (1999)), gastric carcinoma, (Etoh, et al., *Cancer Res.* 61:2145-53 (2001); Lee et al, *Int. J. Oncol.* 18:355-61 (2001)), thyroid tumor (Bunone et al., *Am J Pathol* 155:1967-76 (1999)), non-small cell lung cancer (Wong et al., *Lung Cancer* 29:11-22 (2000)), cancer of colon (Ahmad et al., *Cancer* 92:1138-43 (2001)), and prostate Wurmbach et al., *Anticancer Res.* 20:5217-20 (2000)). Some tumor cells are found to express Ang-2. For example, Tanaka et al. (1999) detected Ang-2 mRNA in 10 out of 12 specimens of human hepatocellular carcinoma (HCC). Ellis' group reported that Ang-2 is expressed ubiquitously in tumor epithelium (Ahmad et al., *Cancer* 92:1138-43 (2001)). Other investigators reported similar findings (Chen et al., *J. Tongji Med. Univ.* 21:228-30, 235 (2001)). By detecting Ang-2 mRNA levels in archived human breast cancer specimens, Sfilogoi et al. (*Int. J. Cancer* 103:466-74 (2003)) reported that Ang-2 mRNA is significantly associated with auxiliary lymph node invasion, short disease-free time and poor overall survival. Tanaka et al. (*Cancer Res.* 62:7124-29 (2002) reviewed a total of 236 patients of non-small cell lung cancer (NSCLC) with pathological stage-I to -IIIA, respectively. Using immunohistochemistry, they found that 16.9% of the NSCLC patients were Ang-2 positive. The microvessel density for Ang-2 positive tumor is significantly higher than that of Ang-2 negative. Such an angiogenic effect of Ang-2 was seen only when VEGF expression was high. Moreover, positive expression of Ang-2 was a significant factor to predict a poor postoperative survival. However, they found no significant correlation between Ang-1 expression and the microvessel density (Tanaka et al., *Cancer Rev.* 62:7124-29 (2002)). These results suggest that Ang-2 is an indicator of poor prognosis patients with several types of cancer.

The development of antibody therapeutics for the treatment of disease is a complex process in which candidate molecules must pass through multiple tests to ensure suitability in every application. In most cases, the initial candidates are developed based on a pre-determined group of desired characteristics, such as antigen affinity, antibody format, and others. Once a candidate molecule is chosen, the suitability for large scale production and stability are considered. Often, the candidate molecule, although highly applicable based on initial desired characteristics, needs to be refined to ensure the prolonged stability and high production efficiency required for feasibility as a commercial therapeutic.

Disulfide bond formation in proteins is a complex process, which is determined by the redox potential of the environment and specialized thiol-disulfide exchanging enzymes (Creighton, Methods Enzymol. 107, 305-329, 1984; Houee-Levin, Methods Enzymol. 353, 35-44, 2002). The disulfides are formed in cells during or shortly after secretion of the nascent chains into the endoplasmic reticulum. Several conformational isoforms of the same protein, but with different disulfide structures, can be generated during recombinant protein production in mammalian cells due to the failing disulfide formation process, close proximity of cysteine residues in the protein structure or surface exposure of unpaired cysteine residues.

In general, cysteine residues in proteins (for example, antibodies specific for Ang-2) are either engaged in cysteine-cysteine disulfide bonds or sterically protected from the disulfide bond formation when they are a part of folded protein region. When a cysteine residue does not have a pair in protein structure and is not sterically protected by folding, it can form a disulfide bond with a free cysteine from solution in a process known as disulfide shuffling. In another process known as disulfide scrambling, free cysteines may also interfere with naturally occurring disulfide bonds (such as those present in antibody structures) and lead to low binding, low biological activity and/or low stability.

Glycosylation of immunoglobulins has also been shown to have significant effects on their binding characteristics, effector functions, structural stability, and rate of secretion from antibody-producing cells (Leatherbarrow et al., *Mol. Immunol.* 22:407 (1985)). In particular, glycosylation of the variable region of antibodies may influence the interaction of the antibody with its cognate antigen. It has been shown that glycosylation in the variable region can have a negative effect on antibody binding affinity, likely due to steric hindrance (Co, M. S., et al., Mol. Immunol. (1993) 30:1361-1367). The heterogeneity of the glycosylation process may also lead to a number of antibody species with altered binding properties. As such, it is desirable to remove or alter the interfering glycosylation site to ensure a consistent antigen binding profile.

Thus, there is a need to develop highly stable antibodies specific for Ang-2 for a variety of therapeutic and diagnostic applications.

Citation or discussion of a reference herein shall not be construed as an admission that such is prior art to the present invention.

SUMMARY

One aspect of the invention provides certain antibodies directed to Angiopoietin-2 (hereinafter referred to as "antibodies of the invention") which are stable and do not readily aggregate in certain pharmaceutical formulations.

In one embodiment, an Ang-2 antibody is provided which comprises a light chain shown as MEDI1, MEDI2, MEDI3, MEDI6 or MEDI4 and/or a heavy chain shown as MEDI5.

Antibodies of the invention have the ability to specifically bind Ang-2 and inhibit tumor angiogenesis and reduce tumor growth. Mechanisms by which this can be achieved can include, but are not limited to, either inhibition of binding of Ang-2 and/or Ang1 to its receptor Tie2, inhibition of Ang-2 and/or Ang-1 induced Tie2 signaling, inhibition of Ang-2 and/or Ang-1 induced Tie2 phosphorylation, or increased clearance of Ang-2 and/or Ang1, therein reducing the effective concentration of Ang-2 and/or Ang-1.

In one embodiment, the antibodies of the invention exhibit enhanced stability as compared to the control Ang-2 specific antibody 3.19.3. In another embodiment, the antibodies of the invention exhibit enhanced production yields as compared to a control Ang-2 specific antibody. In one embodiment, the antibody of the invention is a human Ang-2 antibody which comprises a Val substitution at position 37 of the heavy chain as defined by the EU numbering system ((Kabat et al., *Sequences of Proteins of Immunological Interest*, Fifth Edition, NIH Publication 91-3242, Bethesda Md. (1991), vols. 1-3.), and a substitution of Asp, Thr, Asn, or Ala at position 49 of the light chain based on the Kabat numbering system.

In another embodiment, the antibodies of the invention may comprise a variable light chain amino acid sequence selected from the group consisting of MEDI1 (SEQ ID No.:3), MEDI2 (SEQ ID No.:4), MEDI3 (SEQ ID No.:5), MEDI6 (SEQ ID No.:8) and MEDI4 (SEQ ID No.:6). In another embodiment, the antibodies of the invention may comprise the heavy chain variable amino acid sequence MEDI5 (SEQ ID No.:7). In another embodiment, the antibodies of the invention may comprise a variable light chain amino acid sequence selected from the group consisting of MEDI1 (SEQ ID No.:3), MEDI2 (SEQ ID No.:4), MEDI3 (SEQ ID No.:5), MEDI6 (SEQ ID No.:8) and MEDI4 (SEQ ID No.:6) as well as a heavy chain variable sequence defined as MEDI5 (SEQ ID No.:7).

In another aspect, the invention also provides nucleic acid sequences, vectors and cell lines for expression of the antibodies of the invention.

The invention further provides methods for assaying the level of Angiopoietin-2 (Ang-2) in a patient sample, comprising contacting an anti-Ang-2 antibody with a biological sample from a patient, and detecting the level of binding between said antibody and Ang-2 in said sample. In more specific embodiments, the biological sample is blood.

In other embodiments the invention provides compositions, including an antibody or functional fragment thereof, and a pharmaceutically acceptable carrier.

Further embodiments include methods of effectively treating an animal suffering from an angiogenesis-related disease, including selecting an animal in need of treatment for a neoplastic or non-neoplastic disease, and administering to said animal a therapeutically effective dose of a monoclonal antibody of the invention.

Treatable angiogenesis-related diseases can include neoplastic diseases, such as, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies and epidermoid carcinoma.

Additional embodiments include methods of inhibiting Angiopoietin-2 (Ang-2) induced angiogenesis in an animal. These methods include selecting an animal in need of treatment for Ang-2 induced angiogenesis, and administering to said animal a therapeutically effective dose of an antibody of the invention.

Further embodiments include the use of an antibody of the invention in the preparation of medicament for the treatment of angiogenesis-related diseases in an animal, wherein said antibody specifically binds to Angiopoietin-2 (Ang-2). Treatable angiogenesis-related diseases can include neoplastic diseases, such as, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, cholangiocarcinoma, small bowel adenocarcinoma, pediatric malignancies and epidermoid carcinoma.

Embodiments of the invention described herein relate to monoclonal antibodies that bind Ang-2 and affect Ang-2 and/or Ang1 function. Other embodiments relate to fully human anti-Ang-2 antibodies and anti-Ang-2 antibody preparations with desirable properties from a therapeutic perspective, including high binding affinity for Ang-2, the ability to neutralize Ang-2 and/or Ang1 in vitro and in vivo, and the ability to inhibit Ang-2 and/or Ang-1 induced angiogenesis.

Another embodiment of the invention is a fully human antibody that binds to other Angiopoietin-2 family members including, but not limited to, Angiopoietin-1, Angiopoietin-3, and Angiopoietin-4. A further embodiment herein is an antibody that cross-competes for binding to Tie2 with Ang-2 with the fully human antibodies of the invention. In one embodiment of the invention, the antibody binds to and neutralizes Angiopoietin-2, and also binds to and neutralizes, Angiopoietin-1.

It will be appreciated that embodiments of the invention are not limited to any particular form of an antibody or method of generation or production. For example, the anti-Ang-2 antibody may be a full-length antibody (e.g., having an intact human Fc region) or an antibody fragment (e.g., a Fab, Fab' or F(ab')$_2$). In addition, the antibody may be manufactured from a hybridoma that secretes the antibody, or from a recombinantly produced cell that has been transformed or transfected with a gene or genes encoding the antibody.

Other embodiments of the invention include isolated nucleic acid molecules encoding any of the antibodies described herein or portions thereof, vectors having isolated nucleic acid molecules encoding anti-Ang-2 antibodies or a host cell transformed with any of such nucleic acid molecules. In addition, one embodiment of the invention is a method of producing an anti-Ang-2 antibody by culturing host cells under conditions wherein a nucleic acid molecule is expressed to produce the antibody followed by recovering the antibody. It should be realized that embodiments of the invention also include any nucleic acid molecule which encodes an antibody or fragment of an antibody of the invention including nucleic acid sequences optimized for increasing yields of antibodies or fragments thereof when transfected into host cells for antibody production.

Another embodiment of the invention includes a method of diagnosing diseases or conditions in which an antibody prepared as described herein is utilized to detect the level of Ang-2 in a patient sample. In one embodiment, the patient sample is blood or blood serum. In further embodiments, methods for the identification of risk factors, diagnosis of disease, and staging of disease is presented which involves the identification of the overexpression of Ang-2 using anti-Ang-2 antibodies.

Another embodiment of the invention includes a method for diagnosing a condition associated with the expression of Ang-2 in a cell by contacting the serum or a cell with an anti-Ang-2 antibody, and thereafter detecting the presence of Ang-2. Selected conditions include angiogenesis-related diseases including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

In another embodiment, the invention includes an assay kit for detecting Angiopoietin-2 and Angiopoietin family members in mammalian tissues, cells, or body fluids to screen for angiogenesis-related diseases. The kit includes an antibody that binds to Angiopoietin-2 and a means for indicating the reaction of the antibody with Angiopoietin-2, if present. In one embodiment, the antibody that binds Ang-2 is labeled. In another embodiment the antibody is an unlabeled primary antibody and the kit further includes a means for detecting the primary antibody. In one embodiment, the means includes a labeled second antibody that is an anti-immunoglobulin. In other embodiments, the antibody is labeled with a marker selected from the group consisting of a fluorochrome, an enzyme, a radionuclide and a radiopaque material.

Yet another embodiment includes methods for treating diseases or conditions associated with the expression of Ang-2 in a patient, by administering to the patient an effective amount of an antibody of the invention. The antibody of the invention can be administered alone, or can be administered in combination with chemotherapies, biological/immunological therapies, radiation therapies, hormonal therapies, or surgery. For example, a monoclonal, oligoclonal or polyclonal mixture of Ang-2 antibodies that block angiogenesis can be administered in combination with a drug shown to inhibit tumor cell proliferation directly. The method can be performed in vivo and the patient, in some embodiments, is a human patient. In one embodiment, the method concerns the treatment of angiogenesis-related diseases including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

In another embodiment, the invention provides an article of manufacture including a container. The container includes a composition containing an antibody of the invention, and a package insert or label indicating that the composition can be used to treat angiogenesis-related diseases characterized by the overexpression of Ang-2.

In some embodiments, the anti-Ang-2 antibody is administered to a patient, followed by administration of a clearing agent to remove excess circulating antibody from the blood.

Yet another embodiment is the use of an antibody of the invention in the preparation of a medicament for the treatment of diseases such as angiogenesis-related diseases. In one embodiment, the angiogenesis-related diseases include carcinoma, such as breast, ovarian, stomach, endometrial, salivary gland, lung, kidney, colon, colorectum, esophageal, thyroid, pancreatic, prostate and bladder cancer. In another embodiment, the angiogenesis-related diseases include, but are not limited to, neoplastic diseases, such as, melanoma, small cell lung cancer, non-small cell lung cancer, glioma, hepatocellular (liver) carcinoma, sarcoma, head and neck cancers, mesothelioma, biliary (cholangiocarcinoma), small bowel adenocarcinoma, pediatric malignancies and glioblastoma. In other embodiments, angiogenesis-related disease include, but are not limited to non-neoplastic diseases, such as psoriasis, arthritis (rheumatoid, osteo, and the like), macular degeneration, restenosis, and others.

Ang-2 is an important "on-switch" of angiogenesis. Accordingly, antagonizing this molecule is expected to inhibit pathophysiological procedures, and thereby act as a potent therapy for various angiogenesis-dependent diseases. Besides solid tumors and their metastases, hematological malignancies, such as leukemias, lymphomas and multiple myeloma, are also angiogenesis-dependent. Excessive vascular growth contributes to numerous non-neoplastic disorders. These non-neoplastic angiogenesis-dependent diseases include: atherosclerosis, hemangioma, hemangioendothelioma, angiofibroma, vascular malformations (e.g. Hereditary Hemorrhagic Teleangiectasia (HHT), or Osler-Weber syndrome), warts, pyogenic granulomas, excessive hair growth, Kaposi's sarcoma, scar keloids, allergic edema, psoriasis, dysfunctional uterine bleeding, follicular cysts, ovarian hyperstimulation, endometriosis, respiratory distress, ascites, peritoneal sclerosis in dialysis patients, adhesion formation result from abdominal surgery, obesity, rheumatoid arthritis, synovitis, osteomyelitis, pannus growth, osteophyte, hemophilic joints, inflammatory and infectious processes (e.g. hepatitis, pneumonia, glomerulonephritis), asthma, nasal polyps, liver regeneration, pulmonary hypertension, retinopathy of prematurity, diabetic retinopathy, age-related macular degeneration, leukomalacia, neovascular glaucoma, corneal graft neovascularization, trachoma, thyroiditis, thyroid enlargement, and lymphoproliferative disorders.

In other embodiments, the invention provides methods of using antibodies of the invention in combination with other agents, such as anti-angiogenic or anti-inflammatory agents to treat diseases and/or conditions in a mammal. In one embodiment, methods of the invention comprise the combination of anti-Ang-2 antibodies with antagonists of the biological activity of Colony Stimulating Factor 1 (CSF1) and/or CSF1 receptor (CSF1R) useful to treat disease.

In other embodiments, the invention provides methods of treatment of cancer in a patient. More specifically the methods of the invention may comprise administration of an antagonist of the biological activity of Angiopoietin-2, and/or Tie-2, in combination with a chemotherapeutic agent; a pharmaceutical composition comprising an antagonist of the biological activity of Angiopoietin-2, and/or Tie-2, and a chemotherapeutic agent; a combination product comprising an antagonist of the biological activity of Angiopoietin-2, and/or Tie-2, and a chemotherapeutic agent for use in a method of treatment of a patient; a kit comprising an antagonist of the biological activity of Angiopoietin-2, and/ or Tie-2, and a chemotherapeutic agent; to the use of an antagonist of the biological activity of Angiopoietin-2, and/or Tie-2, and a chemotherapeutic agent in the manufacture of a medicament for use in the production of an anti-cancer effect in a patient. Such combinations are also useful for the treatment of other diseases associated with the activity of Angiopoietin-2, and/or Tie-2.

BRIEF DESCRIPTION OF THE FIGURES

FIG. 12*a* shows the Arthritic score mean (+/−standard error of the mean) against Days from disease onset (i.e. Days of treatment). Closed squares represent PBS vehicle treated animals (n=15), Open triangles represent human IgG isotype control treated animals (n=15), closed circles represent 3.19.3 10 mg/kg treated animals (n=15) and open squares represent Prednisolone 3 mg/kg treated animals (n=10).

FIG. 12*b* shows that no significant changes in mean body weight (g) were observed between each treatment group throughout time course of collagen induced arthritis, suggesting the 3.19.3 therapy was well tolerated. FIG. 12*b* shows Body weight in grams against Days from disease onset (i.e. Days of treatment). Closed squares represent PBS vehicle treated animals (n=15), Open triangles represent human IgG isotype control treated animals (n=15), closed circles represent 3.19.3 10 mg/kg treated animals (n=15) and open squares represent Prednisolone 3 mg/kg treated animals (n=10).

FIG. 13A-D Anti-Ang-2 antibodies inhibit retinal angiogenesis. FIG. 13 represents alterations in angiogenesis of murine retinas in control pups (a) and in pups treated with 0.3 mg/kg MEDI1/5 (b), 1.0 mg/kg MEDI1/5 (c), and 10 mg/kg MEDI1/5 (d). These panels demonstrate that murine retinal angiogenesis is inhibited in a dose-dependent fashion with MEDI1/5 anti-Ang-2 antibodies, as compared to animals treated with control antibodies.

FIG. 14 represents results demonstrating the inhibition of FGF2 mediated angiogenesis in mice by the administration of the anti-Ang-2 antibody, MEDI1/5.

Briefly, Matrigel™ was mixed with FGF2 and implanted subcutaneously into athymic nude mice. MEDI1/5 was dosed intraperitoneally at 1, 10 or 20 mg/kg, on days 1, 4 and 8 of implant. On day 11 post-implant, mice were intravenously dosed with FITC-dextran and Matrigel™ plugs were harvested. Plugs were quantitated for FITC-Dextran content (a) all three doses of MEDI1/5 resulted in significant reduction in angiogenesis (*p<0.05). Plugs were also prepared hematoxylin and eosin staining (b) which showed a lower level of vascularization as compared to the control FGF2 treated sample.

Figure 15A:
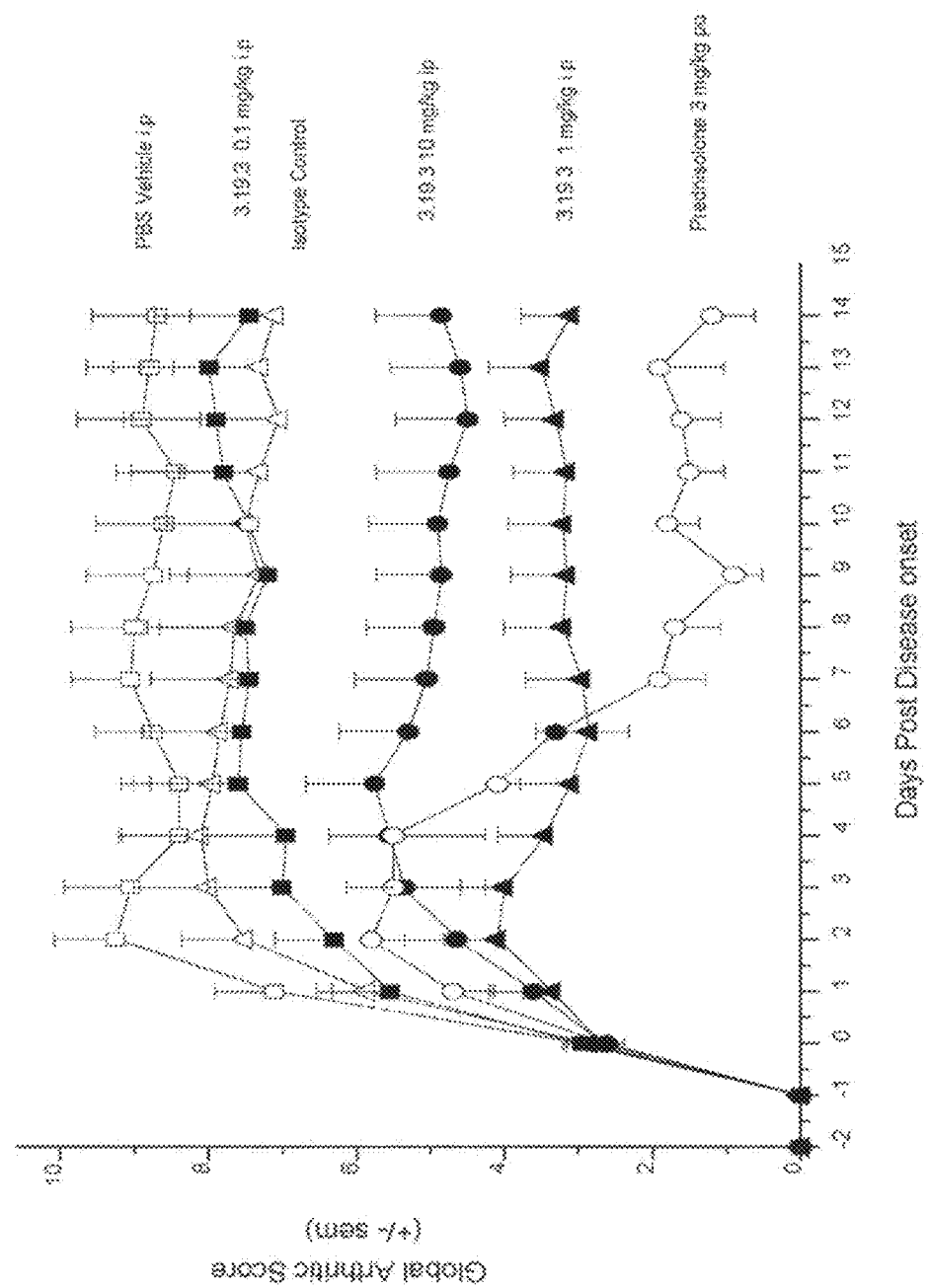

FIG. 15A-H Anti-Ang-2 antibodies inhibit arthritis disease progression. FIG. 15A represents the global arthritic score of arthritis-induced animals treated with various agents including the anti-Ang-2 antibody, 3.19.3 and Prednisolone (open squares=PBS, open triangles=isotype control, closed squares=0.1 mg/kg 3.19.3, closed triangles=1 mg/kg 3.19.3, closed circles=10 mg/kg 3.19.3 and open circles=prednisolone). Dose-dependent reductions in clinical signs of disease progression (arthritic score) and were observed. There was a significant reduction at doses of 1 and 10 mg/kg of 3.19.3. Area under the curve (AUC) for clinical disease progression was calculated for each animal from disease onset and presented in FIG. 15B. FIGS. 15C-H further demonstrate the ameliorative effect of treatment with the anti-Ang-2 antibody 3.19.3. Histolopathological evaluation of CIA model showed evidence of a dose-dependent anti-arthritic effect following administration of 3.19.3 on all parameters evaluated including synovial hyperplasmia (FIG. 15 C), synovitis (FIG. 15 D), pannus (FIG. 15 E), synovial fibrosis (FIG. 15F), and periostitis (FIG. 15G). Histologically, there were no significant differences between the isotype control-treated group and the PBS vehicle group (FIGS. 15C-G). Further, investigation into the microvessel density using CD31 staining showed a significant reduction in the presence of microvessels in the synovium at doses of 1 and 10 mg/kg as well as with prednisolone. There was no effect with 0.1 mg/kg 3.19.3 treatment (FIG. 15 H).

Figure 16C:
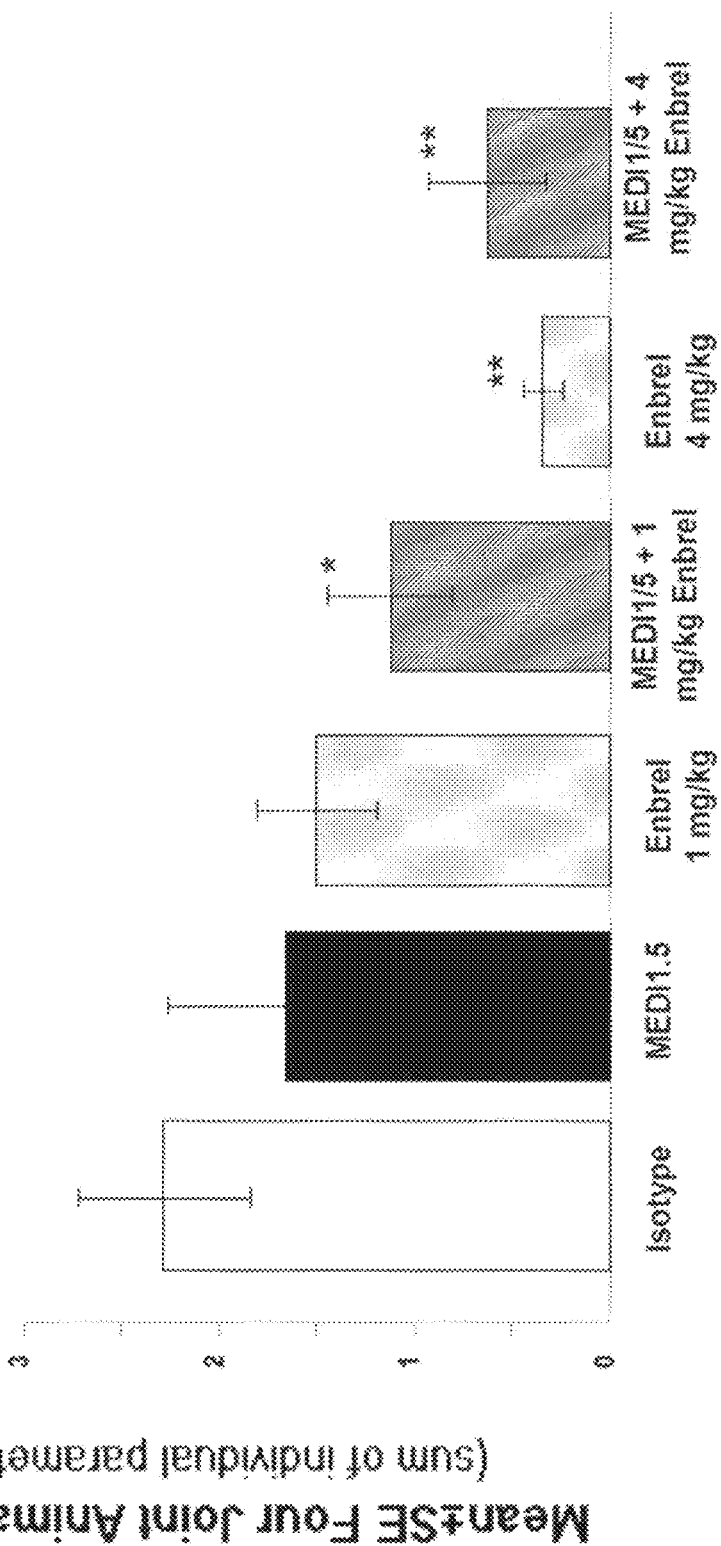
Figure 16D:
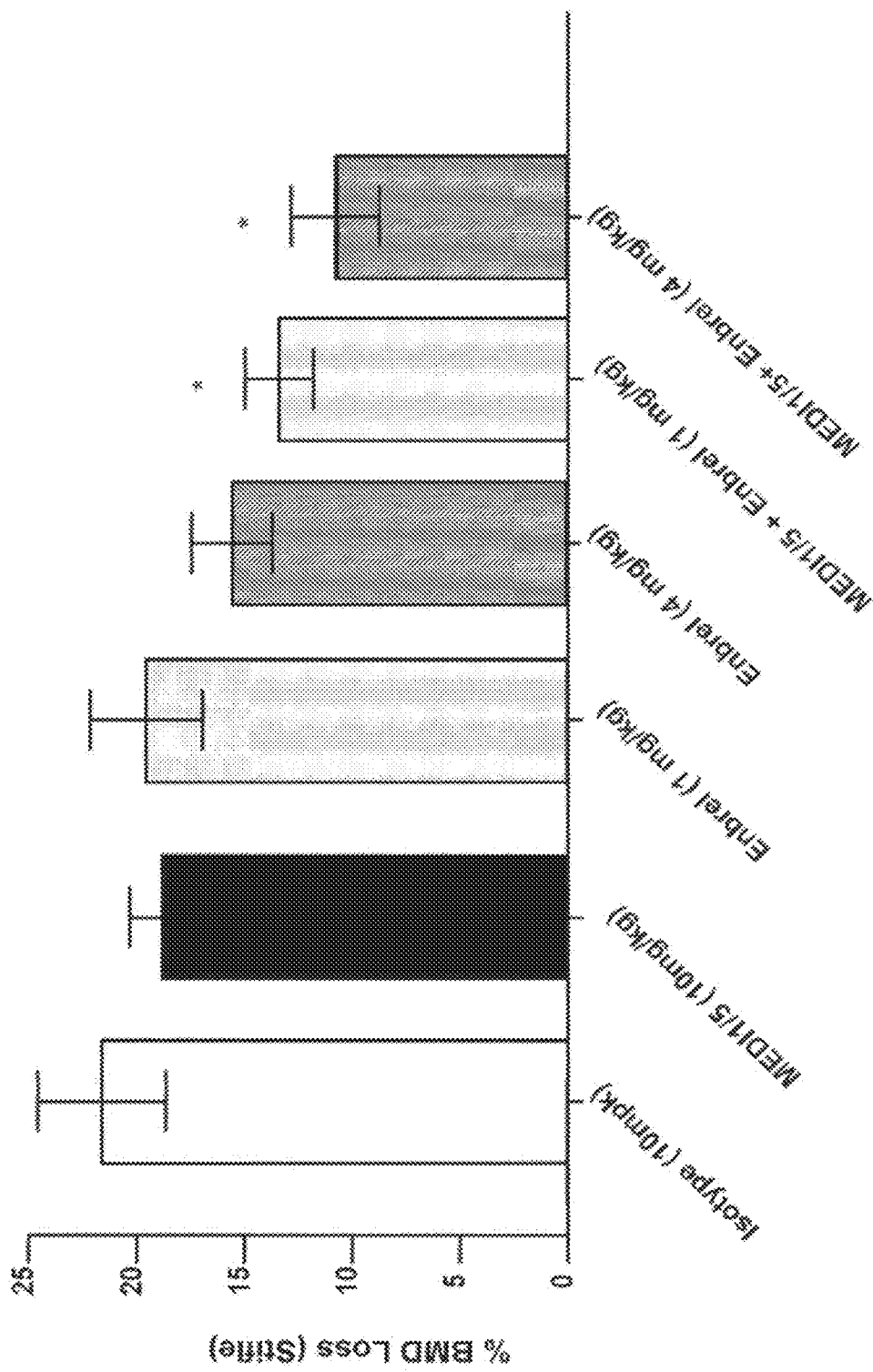

FIG. 16A-D Combinations of Anti-Ang-2 and Anti-TNFα agents demonstrate efficacy in prophylactic treatment of arthritis. FIGS. 16A+B represent the arthritic score of arthritis-induced animals prophylactically treated with a combination of MEDI1/5+etanercept (closed circles=isotype control, closed diamond 10 mg/kg MEDI1/5, open diamond=1 mg/kg etanercept, grey diamond=combination of 10 mg/kg MEDI1/5 with 1 mg/kg etanercept, open square=4 mg/kg enbrel, grey square=combination of 10 mg/kg MEDI1/5 with 4 mg/kg etanercept). A reduction was observed with either etanercept or MEDI1/5 treatment. There was a further reduction in clinical score when MEDI1/5 was administered in combination with the lower dose of etanercept. Histological assessment of synovitis and joint destruction (FIG. 16C) supported the clinical score results as did the protection from loss of bone mineral density (FIG. 16D).

FIG. 17 Combinations of Anti-Ang-2 and Anti-TNFα agents demonstrate efficacy in therapeutic treatment of arthritis When administered in a therapeutic approach following the onset of clinical disease, modest reductions in clinical signs of disease progression (arthritic score) were observed with MEDI1/5 treatment, while both doses of etanercept tested had no effect on disease progression. A more dramatic inhibition of progression of disease when MEDI1/5 (10 mg/kg) was administered in combination with the higher dose of etanercept (4 mg/kg) (FIG. 17 (closed circles=isotype control, closed diamond=MEDI1/5, open diamond=1 mg/kg etanercept, grey diamond=combination of MEDI1/5 with 1 mg/kg etanercept, open square=4 mg/kg etanercept, grey square=combination of MEDI1/5 with 4 mg/kg etanercept).

DETAILED DESCRIPTION

The inventors have found that certain modifications could be made to a particular Ang-2 antibody, which renders the antibody more stable under certain conditions. In particular, by altering residue 49 of the light chain much less aggregation occurred. In addition, when residue 37 of the heavy chain was changed, much less aggregation occurred.

Accordingly, in one embodiment the invention is directed to Ang-2 antibodies having one or more improved characteristics over control antibody 3.19.3. Such characteristics include increased stability, decreased aggregation and increased production efficiency. In one embodiment, the antibodies of the invention efficiently inhibit Ang-2 and/or Ang-1 signaling through the Tie2 receptor to modulate processes such as angiogenesis and tumor growth.

Embodiments of the invention described herein relate to monoclonal antibodies specific for Ang-2, which may be derived from the antibody 3.19.3 and which exhibit increased stability and/or production efficiencies. In some embodiments, the antibodies bind to Ang-2 and inhibit the binding of Ang-2 to its receptor, Tie2. Other embodiments of the invention include fully human anti-Ang-2 antibodies, and antibody preparations that are therapeutically useful. Such anti-Ang-2 antibody preparations have desirable therapeutic properties, including strong binding affinity for Ang-2, the ability to neutralize Ang-2 in vitro, and the ability to inhibit Ang-2-induced angiogenesis in vivo. Antibodies of the invention comprise the ability to specifically bind Ang-2 and inhibit tumor angiogenesis and reduce tumor growth. Mechanisms by which this can be achieved can include and are not limited to either inhibition of binding of Ang-2 to its receptor Tie2, inhibition of Ang-2 induced Tie2 signaling, or increased clearance of Ang-2, therein reducing the effective concentration of Ang-2.

In other embodiments, the antibodies may bind to both Ang-2 and Ang-1 and/or modulate one or more functional activities of both Ang-1 and Ang-2.

One aspect of the invention provides stabilized antibodies which comprise a substitution of an amino acid at position 49 (as compared to the light chain variable amino acid sequence of Ang-2 antibody 3.19.3, see SEQ ID No.1) as defined by the Kabat numbering system (Kabat et al., *Sequences of Proteins of Immunological Interest*, Fifth Edition, NIH Publication 91-3242, Bethesda Md. (1991), vols. 1-3.). In one embodiment, the amino acid substitution at position 49 may be any amino acid. In a specific embodiment, the amino acid substitution at position 49 is selected from the group consisting of Asp, Thr, Asn, and Ala.

In another embodiment, antibodies of the invention further comprises a substitution of Val substitution at position 37 of the heavy chain (as compared to the heavy chain variable amino acid sequence of Ang-2 antibody 3.19.3, see, SEQ ID No. 2) as defined by the EU numbering system ((Kabat et al., *Sequences of Proteins of Immunological Interest*, Fifth Edition, NIH Publication 91-3242, Bethesda Md. (1991), vols. 1-3.).

In one embodiment, the antibodies of the invention exhibit enhanced stability as compared to antibody 3.19.3. In another embodiment, the antibodies of the invention exhibit enhanced production yields as compared to 3.19.3.

In another embodiment, the antibodies of the invention may comprise variable light chain acid sequences selected from the group consisting of MEDI1 (SEQ ID No.:3), MEDI2 (SEQ ID No.:4), MEDI3 (SEQ ID No.:5), MEDI6 (SEQ ID NO:8), and MEDI4 (SEQ ID No.:6). In another embodiment, the antibodies of the invention may comprise the heavy chain variable sequence of MEDI5 (SEQ ID No.:7). In another embodiment, the antibodies of the invention may comprise variable light chain sequences selected from the group consisting of MEDI1 (SEQ ID No.:3), MEDI2 (SEQ ID No.:4). MEDI3 (SEQ ID No.:5), MEDI6 (SEQ ID NO:8), and MEDI4 (SEQ ID No.:6) and further comprise the heavy chain variable sequence of MEDI5 (SEQ ID No.:7). As used herein, an antibody of the invention comprising a light chain and a heavy chain may be referred to as a MEDIX/MEDIY wherein X represents the light chain sequence and Y represents the heavy chain sequence.

In another embodiment, the antibodies of the invention may comprise variable light chain acid sequences selected from the group consisting of MEDI1 (SEQ ID No.:3). MEDI2 (SEQ ID No.:4), MEDI3 (SEQ ID No.:5), MEDI6 (SEQ ID NO:8), and MEDI4 (SEQ ID No.:6), but having a different amino acid substitution at position 49. In another embodiment, the antibodies of the invention may further comprise the heavy chain variable sequence of MEDI5 (SEQ ID No.:7). In another embodiment, the antibodies of the invention may comprise variable light chain sequences selected from the group consisting of MEDI1 (SEQ ID No.:3), MEDI2 (SEQ ID No.:4), MEDI3 (SEQ ID No.:5), MEDI6 (SEQ ID NO:8), and MEDI4 (SEQ ID No.:6), but having a different amino acid substitution at position 49, and further comprise the heavy chain variable sequence of MEDI5 (SEQ ID No.:7).

Modulation of Unpaired Cysteine Residues:

Disulfide bond formation in proteins is a complex process, which is determined by the redox potential of the environment and specialized thiol-disulfide exchanging enzymes (Creighton, Methods Enzymol. 107, 305-329, 1984; Houee-Levin, Methods Enzymol. 353, 35-44, 2002). In general, cysteine residues in proteins (for example, antibodies specific for Ang-2) are either engaged in cysteine-cysteine disulfide bonds or sterically protected from the disulfide bond formation when they are a part of folded protein region. When a cysteine residue does not have a pair in protein structure and is not sterically protected by folding, it can form a disulfide bond with a free cysteine from solution in a process known as disulfide shuffling. In another process known as disulfide scrambling, free cysteines may also interfere with naturally occurring disulfide bonds (such as those present in antibody structures) and lead to low binding, low biological activity and/or low stability.

Modulation of Glycosylation Sites:

It has been shown that glycosylation in the variable region can have a negative effect on antibody binding affinity, likely due to steric hindrance (Co, M. S., et al., Mol. Immunol. (1993) 30:1361-1367). The heterogeneity of the glycosylation process may also lead to a number of antibody species with altered binding properties. As such, it is desirable to remove or alter the interfering glycosylation site to ensure a consistent antigen binding profile. One method to remove potential or observed glycosylation sites is site-directed mutagenesis to substitute at least one potential glycosylation site (such as an asparagine, threonine or serine amino acid) with another amino acid that cannot serve as a glycosylation site. Accordingly, in one embodiment, the antibodies of the invention comprise substituted amino acids that do not serve as glycosylation sites. In one embodiment, the glycosylation site to be modified occurs in the variable region. In another embodiment, the glycosylation site to be modified occurs in a complementary determining region (CDR) of an antibody. In another embodiment, the glycosylation site to be modified is the $2^{nd}$ light chain CDR. In other embodiments, the sequences surrounding the glycosylation site are modified. In another embodiment, the glycosylation site to be modified occurs in the constant region. In another embodiment, the antibodies of the invention comprise at least one, at least two, at least three, at least four or more modified glycosylation sites.

In some embodiments, antibodies of the invention comprise a light chain which is engineered to remove at least one O-glycosylation site. In some embodiments, antibodies of the invention comprise a light chain selected from the group consisting of MEDI1 (SEQ ID No.:3), MEDI2 (SEQ ID No.:4), MEDI3 (SEQ ID No.:5), and MEDI4 (SEQ ID No.:6) wherein said light chain further comprises an amino acid substitution at Kabat position 59, wherein said amino acid is not proline. In a specific embodiment, antibodies of the invention comprise a light chain having the sequence corresponding to MEDI6 (SEQ ID NO:8).

The amino acid sequences of selected antibody heavy and light chains can be compared to germline heavy and light chain amino acid sequences. In cases where certain framework residues of the selected VL and/or VH chains differ from the germline configuration (e.g., as a result of somatic mutation of the immunoglobulin genes used to prepare the phage library), it may be desirable to "backmutate" the altered framework residues of the selected antibodies to the germline configuration (i.e., change the framework amino acid sequences of the selected antibodies so that they are the same as the germline framework amino acid sequences). Such "backmutation" (or "germlining") of framework residues can be accomplished by standard molecular biology methods for introducing specific mutations (e.g., site-directed mutagenesis; PCR-mediated mutagenesis, and the like). In one embodiment, the variable light and/or heavy chain framework residues are backmutated. In another embodiment, the variable heavy chain of an antibody of the invention is backmutated. In another embodiment, the variable heavy chain of an antibody of the invention comprises at least one, at least two, at least three, at least four or more backmutations. In a specific embodiment, the variable heavy chain of an antibody of the invention comprises a backmutation of the glycine residue occupying position 37. In another specific embodiment, the variable heavy chain of an antibody of the invention comprises a backmutation of position 37 corresponding to a glycine to valine substitution.

Modulation of the Fc Region

The invention also provides antibodies with altered Fc regions (also referred to herein as "variant Fc regions"). Accordingly, in one embodiment of the invention, antibodies of the invention comprise a variant Fc region (i.e., Fc regions that have been altered as discussed below). Antibodies of the invention comprising a variant Fc region are also referred to here as "Fc variant protein(s)."

In the description of variant Fc regions, it is understood that the Fc regions of the antibodies of the invention comprise the numbering scheme according to the EU index as in Kabat et al. (1991, NIH Publication 91-3242, National Technical Information Service, Springfield, Va.).

It is known that variants of the Fc region (e.g., amino acid substitutions and/or additions and/or deletions) enhance or diminish effector function (see Presta et al., 2002, *Biochem Soc Trans* 30:487-490; U.S. Pat. Nos. 5,624,821, 5,885,573 and PCT publication Nos. WO 00/42072, WO 99/58572 and WO 04/029207). Accordingly, in one embodiment, the antibodies of the invention comprise variant Fc regions. In one embodiment, the variant Fc regions of antibodies exhibit a similar level of inducing effector function as compared to the native Fc. In another embodiment, the variant Fc region exhibits a higher induction of effector function as compared to the native Fc. In another embodiment, the variant Fc region exhibits lower induction of effector function as compared to the native Fc. In another embodiment, the variant Fc region exhibits higher induction of ADCC as compared to the native Fc. In another embodiment, the variant Fc region exhibits lower induction of ADCC as compared to the native Fc. In another embodiment, the variant Fc region exhibits higher induction of CDC as compared to the native Fc. In another embodiment, the variant Fc region exhibits lower induction of CDC as compared to the native Fc. Specific embodiments of variant Fc regions are detailed infra.

It is also known in the art that the glycosylation of the Fc region can be modified to increase or decrease effector function (see for examples, Umana et al, 1999, Nat. Biotechnol 17:176-180; Davies et al., 2001, Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland). Accordingly, in one embodiment the Fc regions of antibodies of the invention comprise altered glycosylation of amino acid residues. In another embodiment, the altered glycosylation of the amino acid residues results in lowered effector function. In another embodiment, the altered glycosylation of the amino acid residues results in increased effector function. In a specific embodiment, the Fc region has reduced fucosylation. In another embodiment, the Fc region is afucosylated (see for examples, U.S. Patent Application Publication No. 2005/0226867).

Recent research suggests that the addition of sialic acid to the oligosaccharides on IgG molecules enhances their anti-inflammatory activity and alter their cytotoxicity (Keneko et al., Science 313, 670-673(2006), Scallon et al., Mol. Immuno. 2007 March; 44(7): 1524-34). Thus, the efficacy of antibody therapeutics may be optimized by selection of a glycoform that is best suited to the intended application. The two oligosaccharide chains interposed between the two CH2 domains of antibodies are involved in the binding of the Fc region to its receptors. The studies referenced above demonstrate that IgG molecules with increased sialylation have anti-inflammatory properties whereas IgG molecules with reduced sialylation have increased immunostimulatory properties. Therefore, an antibody therapeutic can be "tailor-made" with an appropriate sialylation profile for a particular application. Methods for modulating the sialylation state of antibodies are presented in WO2007/005786 entitled "Methods And Compositions With Enhanced Therapeutic Activity", and WO2007/117505 entitled "Polypeptides With Enhanced Anti-Inflammatory And Decreased Cytotoxic Properties And Related Methods" each of which are incorporated by reference in their entireties for all purposes.

In one embodiment, the Fc regions of antibodies of the invention comprise an altered sialylation profile compared to a reference unaltered Fc region. In one embodiment, the Fc regions of antibodies of the invention comprise an increased sialylation profile compared to a reference unaltered Fc region. In some embodiments the Fc regions of antibodies of the invention comprise an increase in sialylation of about 5%, about 10%, about 15%, about 20%, about 25%, about 30%, about 35%, about 40%, about 45%, about 50%, about 60%, about 65%, about 70%, about 80%, about 85%, about 90%, about 95%, about 100%, about 125%, about 150% or more as compared to a reference unaltered Fc region. In some embodiments the Fc regions of antibodies of the invention comprise an increase in sialylation of about 2 fold, about 3 fold, about 4 fold, about 5 fold, about 10 fold, about 20 fold, about 50 fold or more as compared to an unaltered reference Fc region.

In another embodiment, the Fc regions of antibodies of the invention comprise a decreased sialylation profile compared to a reference unaltered Fc region. In some embodiments, the Fc regions of antibodies of the invention comprise a decrease in sialylation of about 5%, about 10%, about 15%, about 20%, about 25%, about 30%, about 35%, about 40%, about 45%, about 50%, about 60%, about 65%, about 70%, about 80%, about 85%, about 90%, about 95%, about 100%, about 125%, about 150% or more as compared to a reference unaltered Fc region. In some embodiments the Fc regions of antibodies of the invention comprise a decrease in sialylation of about 2 fold, about 3 fold, about 4 fold, about 5 fold, about 10 fold, about 20 fold, about 50 fold or more as compared to an unaltered reference Fc region.

It is also known in the art that the Fc region can be modified to increase the half-lives of proteins. The increase in half-life allows for the reduction in amount of drug given to a patient as well as reducing the frequency of administration. Accordingly, antibodies of the invention with increased half-lives may be generated by modifying (for example, substituting, deleting, or adding) amino acid residues identified as involved in the interaction between the Fc and the FcRn receptor (see, for examples, PCT publication Nos. 97/34631 and 02/060919 each of which are incorporated by reference in their entireties). In addition, the half-life of antibodies of the invention may be increase by conjugation to PEG or Albumin by techniques widely utilized in the art. In some embodiments the Fc regions of antibodies of the invention comprise an increase in half-life of about 5%, about 10%, about 15%, about 20%, about 25%, about 30%, about 35%, about 40%, about 45%, about 50%, about 60%, about 65%, about 70%, about 80%, about 85%, about 90%, about 95%, about 100%, about 125%, about 150% or more as compared to a reference unaltered Fc region. In some embodiments the Fc regions of antibodies of the invention comprise an increase in half-life of about 2 fold, about 3 fold, about 4 fold, about 5 fold, about 10 fold, about 20 fold, about 50 fold or more as compared to an unaltered reference Fc region.

The present invention encompasses Fc variant proteins which have altered binding properties for an Fc ligand (e.g., an Fc receptor, C1q) relative to a comparable molecule (e.g., a protein having the same amino acid sequence except having a wild type Fc region). Examples of binding properties include but are not limited to, binding specificity, equilibrium dissociation constant ($K_D$), dissociation and association rates ($k_{off}$ and $k_{on}$ respectively), binding affinity and/or avidity. It is generally understood that a binding molecule (e.g., a Fc variant protein such as an antibody) with a low $K_D$ may be more desirable to a binding molecule with a high $K_D$. However, in some instances the value of the $k_{on}$ or $k_{off}$ may be more relevant than the value of the $K_D$. One skilled in the art can determine which kinetic parameter is most important for a given antibody application.

The affinities and binding properties of an Fc region for its ligand may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immunoabsorbent assay (ELISA), or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In one embodiment, the Fc variant protein has enhanced binding to one or more Fc ligand relative to a comparable molecule. In another embodiment, the Fc variant protein has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than that of a comparable molecule. In a specific embodiment, the Fc variant protein has enhanced binding to an Fc receptor. In another specific embodiment, the Fc variant protein has enhanced binding to the Fc receptor FcγRIIA. In a further specific embodiment, the Fc variant protein has enhanced biding to the Fe receptor FcγRIIB. In still another specific embodiment, the Fc variant protein has enhanced binding to the Fc receptor FcRn. In yet another specific embodiment, the Fc variant protein has enhanced binding to C1q relative to a comparable molecule.

The serum half-life of proteins comprising Fc regions may be increased by increasing the binding affinity of the Fc region for FcRn. In one embodiment, the Fc variant protein has enhanced serum half life relative to comparable molecule.

The ability of any particular Fc variant protein to mediate lysis of the target cell by ADCC can be assayed. To assess ADCC activity an Fc variant protein of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, J Exp Med 166:1351-1361; Wilkinson et al., 2001, J Immunol Methods 258:183-191; Patel et al., 1995 J Immunol Methods 184:29-38. ADCC activity of the Fc variant protein of interest may also be assessed in vivo, e.g., in an animal model such as that disclosed in Clynes et al., 1998, *Proc. Nat. Acad. Sci. USA* 95:652-656.

In one embodiment, an Fe variant protein has enhanced ADCC activity relative to a comparable molecule. In a specific embodiment, an Fc variant protein has ADCC activity that is at least 2 fold, or at least 3 fold, or at least 5 fold or at least 10 fold or at least 50 fold or at least 100 fold greater than that of a comparable molecule. In another specific embodiment, an Fc variant protein has enhanced binding to the Fc receptor FcγRIIIA and has enhanced ADCC activity relative to a comparable molecule. In other embodiments, the Fc variant protein has both enhanced ADCC activity and enhanced serum half life relative to a comparable molecule.

In one embodiment, an Fc variant protein has reduced ADCC activity relative to a comparable molecule. In a specific embodiment, an Fc variant protein has ADCC activity that is at least 2 fold, or at least 3 fold, or at least 5 fold or at least 10 fold or at least 50 fold or at least 100 fold lower than that of a comparable molecule. In another specific embodiment, an Fc variant protein has reduced binding to the Fc receptor FcγRIIIA and has reduced ADCC activity relative to a comparable molecule. In other embodiments, the Fc variant protein has both reduced ADCC activity and enhanced serum half life relative to a comparable molecule.

In one embodiment, an Fc variant protein has enhanced CDC activity relative to a comparable molecule. In a specific embodiment, an Fc variant protein has CDC activity that is at least 2 fold, or at least 3 fold, or at least 5 fold or at least 10 fold or at least 50 fold or at least 100 fold greater than that of a comparable molecule. In other embodiments, the Fc variant protein has both enhanced CDC activity and enhanced serum half life relative to a comparable molecule.

In one embodiment, the Fc variant protein has reduced binding to one or more Fc ligand relative to a comparable molecule. In another embodiment, the Fc variant protein has an affinity for an Fc ligand that is at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold lower than that of a comparable molecule. In a specific embodiment, the Fc variant protein has reduced binding to an Fc receptor. In another specific embodiment, the Fc variant protein has reduced binding to the Fc receptor FcγRIIIA. In a further specific embodiment, an Fc variant described herein has an affinity for the Fc receptor FcγRIIIA that is at least about 5 fold lower than that of a comparable molecule, wherein said Fc variant has an affinity for the Fc receptor FcγRIIB that is within about 2 fold of that of a comparable molecule. In still another specific embodiment, the Fc variant protein has reduced binding to the Fe receptor FcRn. In yet another specific embodiment, the Fe variant protein has reduced binding to C1q relative to a comparable molecule.

In one embodiment, the present invention provides Fc variants, wherein the Fc region comprises a non naturally occurring amino acid residue at one or more positions selected from the group consisting of 234, 235, 236, 237, 238, 239, 240, 241, 243, 244, 245, 247, 251, 252, 254, 255, 256, 262, 263, 264, 265, 266, 267, 268, 269, 279, 280, 284, 292, 296, 297, 298, 299, 305, 313, 316, 325, 326, 327, 328, 329, 330, 331, 332, 333, 334, 339, 341, 343, 370, 373, 378, 392, 416, 419, 421, 440 and 443 as numbered by the EU index as set forth in Kabat. Optionally, the Fc region may comprise a non naturally occurring amino acid residue at additional and/or alternative positions known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752; WO 04/074455: WO 04/099249; WO 04/063351; WO 05/070963; WO 05/040217, WO 05/092925 and WO 06/020114).

In a specific embodiment, the present invention provides an Fc variant, wherein the Fc region comprises at least one non naturally occurring amino acid residue selected from the group consisting of 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235F, 236E, 239D, 239E, 239N, 239Q, 239F, 239T, 239H, 239Y, 240I, 240A, 240T, 240M, 241W, 241 L, 241Y, 241E, 241 R, 243W, 243L 243Y, 243R, 243Q, 244H, 245A, 247L, 247V, 247G, 251F, 252Y, 254T, 255L, 256E, 256M, 262I, 262A, 262T, 262E, 263I, 263A, 263T, 263M, 264L, 264I, 264W, 264T, 264R, 264F, 264M, 264Y, 264E, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 269G, 297S, 297D, 297E, 298H, 298I, 298T, 298F, 299I, 299L, 299A, 299S, 299V, 299H, 299F, 299E, 305I, 313F, 316D, 325Q, 325L, 325I, 325D, 325E, 325A, 325T, 325V, 325H, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 339T, 370E, 370N, 378D, 392T, 396L, 416G, 419H, 421K, 440Y and 434W as numbered by the EU index as set forth in Kabat. Optionally, the Fc region may comprise additional and/or alternative non naturally occurring amino acid residues known to one skilled in the art (see, e.g., U.S. Pat. Nos. 5,624,821; 6,277,375; 6,737,056; PCT Patent Publications WO 01/58957; WO 02/06919; WO 04/016750; WO 04/029207; WO 04/035752 and WO 05/040217).

Antibody Affinity

In one embodiment of the invention there is provided an antibody that binds to Angiopoietin-1 and prevents Angiopoietin-1 binding to Tie-2. Yet another embodiment of the invention is a monoclonal antibody that binds to Angiopoietin-1 and/or Angiopoietin-2 and inhibits Angiopoietin-1 and/or Angiopoietin-2 induced Tie-2 phosphorylation. In one embodiment, the antibody binds Angiopoietin-1 and/or Angiopoietin-2 with a $K_d$ of less than 1 nanomolar (nM). In other embodiments, the antibody binds with a $K_d$ less than 500 picomolar (pM). In other embodiments, the antibody binds with a $K_d$ less than 100 picomolar (pM). In yet other embodiments, the antibody binds with a $K_d$ less than 30 picomolar (pM). In further embodiments, the antibody binds with a $K_d$ of less than 20 pM. In yet further embodiments, the antibody binds with a $K_d$ of less than 10 or 5 pM.

Antibodies of the invention may have a high binding affinity Ang-1 and/or Ang-2. For example, an antibody described herein may have an association rate constant or $k_{on}$ rate (antibody (Ab)+antigen→Ab-Ag) of at least $2\times10^5$ $M^{-1}s^{-1}$, at least $5\times10^5$ $M^{-1}s^{-1}$, at least $10^6$ $M^{-1}s^{-1}$, at least $5\times10^6$ $M^{-1}s^{-1}$, at least $10^7$ $M^{-1}s^{-1}$, at least $5\times10^7$ $M^{-1}s^{-1}$, or at least $10^8$ $M^{-1}s^{-1}$.

In another embodiment, an antibody may have a $k_{off}$ rate (Ab-Ag→Ab+Ag) of less than $5\times10^{-1}$ $s^{-1}$, less than $10^{-1}$ $s^{-1}$, less than $5\times10^{-2}$ $s^{-1}$, less than $10^{-2}$ $s^{-1}$, less than $5\times10^{-3}$ $s^{-1}$, less than $10^{-3}$ $s^{-1}$, less than $5\times10^{-4}$ $s^{-1}$, or less than $10^4$ $s^{-1}$, In a another embodiment, an antibody of the invention has a $k_{off}$ of less than $5\times10^{-5}$ $s^{-1}$, less than $10^{-5}$ $s^{-1}$, less than $5\times10^{-6}$ $s^{-1}$, less than $10^{-6}$ $s^{-1}$, less than $5\times10^{-7}$ $s^{-1}$, less than $10^{-7}$ $s^{-1}$, less than $5\times10^{-8}$ $s^{-1}$, less than $10^{-8}$ $s^{-1}$, less than $5\times10^{-9}$ $s^{-1}$, less than $10^{-9}$ $s^{-1}$, or less than $10^{-10}$ $s^{-1}$.

In another embodiment, an antibody may have an affinity constant or $K_a$ ($k_{on}/k_{off}$) of at least $10^2$ $M^{-1}$, at least $5\times10^2$ $M^{-1}$, at least $10^3$ $M^{-1}$, at least $5\times10^3$ $M^{-1}$, at least $10^4$ $M^{-1}$, at least $5\times10^4$ $M^{-1}$, at least $10^5$ $M^{-1}$, at least $5\times10^5$ $M^{-1}$, at least $10^6$ $M^{-1}$, at least $5\times10^6$ $M^{-1}$, at least $10^7$ $M^{-1}$, at least $5\times10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{11}$ $M^{-1}$, at least $10^{12}$ $M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$. In yet another embodiment, an antibody may have a dissociation constant or $K_d$ ($k_{off}/k_{on}$) of less than $5\times10^{-2}$ M, less than $10^{-2}$ M, less than $5\times10^{-3}$ M, less than $10^{-3}$ M, less than $5\times10^{-4}$ M, less than $10^{-4}$ M, less than $5\times10^{-5}$ M, less than $10^{-5}$ M, less than $5\times10^{-6}$ M, less than $10^{-6}$ M, less than $5\times10^{-7}$ M, less than $10^{-7}$ M, less than $5\times10^{-8}$ M, less than $10^{-8}$ M, less than $5\times10^{-9}$ M, less than $10^{-9}$ M, less than $5\times10^{-10}$ M, less than $10^{-10}$ M, less than $5\times10^{-11}$ M, less than $10^{-11}$ M, less than $5\times10^{-12}$ M, less than $10^{-12}$ M, less than $5\times10^{-13}$ M, less than $10^{-13}$ M, less than $5\times10^{-14}$ M, less than $10^{-14}$ M, less than $5\times10^{-15}$ M, or less than $10^{-15}$ M.

An antibody used in accordance with a method described herein may have a dissociation constant ($K_d$) of less than 3000 pM, less than 2500 pM, less than 2000 pM, less than 1500 pM, less than 1000 pM, less than 750 pM, less than 500 pM, less than 250 pM, less than 200 pM, less than 150 pM, less than 100 pM, less than 75 pM as assessed using a method described herein or known to one of skill in the art (e.g., a BIAcore assay, ELISA) (Biacore International AB, Uppsala, Sweden). In a specific embodiment, an antibody used in accordance with a method described herein may have a dissociation constant ($K_d$) of between 25 to 3400 pM, 25 to 3000 pM, 25 to 2500 pM, 25 to 2000 pM, 25 to 1500 pM, 25 to 1000 pM, 25 to 750 pM, 25 to 500 pM, 25 to 250 pM, 25 to 100 pM, 25 to 75 pM, or 25 to 50 pM as assessed using a method described herein or known to one of skill in the art (e.g., a BIAcore assay, ELISA). In another embodiment, an antibody used in accordance with a method described herein may have a dissociation constant ($K_d$) of 500 pM, 100 pM, 75 pM or 50 pM as assessed using a method described herein or known to one of skill in the art (e.g., a BIAcore assay, ELISA).

One embodiment of the invention includes an antibody that binds to and neutralizes Ang-2, but does not bind to Ang-1. In another embodiment, the antibody binds to both Ang-2 and Ang-1, but only neutralizes Ang-2. In another embodiment, the antibody binds to both Ang-2 and Ang-1, and neutralizes binding of both Ang-1 and Ang-2 to Tie2.

In one embodiment, antibodies of the invention preferentially bind Ang-2 over Ang-1. In some embodiments, antibodies of the invention bind Ang-2 over Ang-1 in a ratio of at least 2:1, at least 3:1, at least 4:1, at least 5:1, at least 6:1, at least 7:1, at least 8:1, at least 9:1, at least 10:1, at least 15:1, at least 20:1, at least 25:1, at least 50:1, at least 100:1, at least 250:1, at least 500:1, at least 1000:1 or at least 10,000:1 or higher.

In one embodiment, antibodies of the invention preferentially bind Ang-1 over Ang-2. In some embodiments, antibodies of the invention bind Ang-1 over Ang-2 in a ratio of at least 2:1, at least 3:1, at least 4:1, at least 5:1, at least 6:1, at least 7:1, at least 8:1, at least 9:1, at least 10:1, at least 15:1, at least 20:1, at least 25:1, at least 50:1, at least 100:1, at least 250:1, at least 500:1, at least 1000:1 or at least 10,000:1 or higher.

Embodiments of the invention also include isolated binding fragments of anti-Ang-2 antibodies. In one embodiment, the binding fragments are derived from fully human anti-Ang-2 antibodies. Exemplary fragments include Fv, Fab' or other well know antibody fragments, as described in more detail below. Embodiments of the invention also include cells that express fully human antibodies against Ang-2. Examples of cells include hybridomas, or recombinantly created cells, such as Chinese hamster ovary (CHO) cells, variants of CHO cells (for example DG44), 293 cells and NS0 cells that produce antibodies against Ang-2. Additional information about variants of CHO cells can be found in Andersen and Reilly (2004) Current Opinion in Biotechnology 15, 456-462 which is incorporated herein in its entirety by reference.

Preparation of Antibodies

Nucleic Acids Encoding Antibodies of the Invention

The invention also encompasses isolated nucleic acid molecules encoding antibodies of the invention. In another embodiment, the antibody is derived from the fully human monoclonal antibody 3.19.3. In one embodiment there is provided an antibody which binds to the same epitope or epitopes as fully human monoclonal antibody 3.19.3.

In one embodiment, the isolated nucleic acid encodes an antibody variable light chain corresponding to an amino acid sequence selected from the group consisting of MEDI1 (SEQ ID No.:3), MEDI2 (SEQ ID No.:4), MEDI3 (SEQ ID No.:5), MEDI6 (SEQ ID NO:8), and MEDI4 (SEQ ID No.:6). In another embodiment, the isolated nucleic acid encodes an antibody further comprising a variable heavy chain corresponding to the amino acid sequence MEDI5 (SEQ ID NO:7). In a specific embodiment, the nucleic acids of the invention encode an antibody comprising a variable light chain corresponding to an amino acid sequence selected from the group consisting of MEDI1 (SEQ ID No.:3), MEDI2 (SEQ ID No.:4), MEDI3 (SEQ ID No.:5), MEDI6 (SEQ ID NO:8), and MEDI4 (SEQ ID No.:6); and further comprises a variable heavy chain further comprising the amino acid sequence MEDI5 (SEQ ID No.: 7).

Recombinant Expression Systems

Recombinant expression of an antibody of the invention requires construction of an expression vector containing a polynucleotide that encodes the antibody of the invention. Once a polynucleotide encoding the antibody of the invention has been obtained, the vector for the production of the antibody may be produced by recombinant DNA technology using techniques well-known in the art (e.g., U.S. Pat. No. 6,331,415, which is incorporated herein by reference in its entirety). Thus, methods for preparing a protein by expressing a polynucleotide containing an encoding nucleotide sequence are described herein. The antibodies of the invention can be produced in many different expression systems. In one embodiment, the antibodies of the invention are produced and secreted by mammalian cells. In another embodiment, the antibodies of the invention are produced and secreted in human cells. In a specific embodiment, the antibodies of the invention are produced in cells of the 293F, CHO, or NS0 cell line.

Methods which are known to those skilled in the art can be used to construct expression vectors containing protein coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule operably linked to a promoter.

Once the expression vector is transferred to a host cell by conventional techniques, the transfected cells are then cultured by conventional techniques to produce an antibody. Thus, the invention includes host cells containing a polynucleotide encoding a protein of the invention operably linked to a heterologous promoter.

A variety of host-expression vector systems may be utilized to express antibodies of the invention or portions thereof as described in U.S. Pat. No. 5,807,715. For example, mammalian cells such as Chinese hamster ovary cells (CHO), in conjunction with a vector such as the major intermediate early gene promoter element from human cytomegalovirus is an effective expression system for antibodies (Foecking et al., *Gene*, 45:101 (1986); and Cockett et al., *Bio/Technology*, 8:2 (1990)). In addition, a host cell strain may be chosen which modulates the expression of inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the protein of the invention. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293F, 293T, 3T3, W138, BT483, Hs578T, HTB2, BT2O and T47D, NS0, CRL7O3O and HsS78Bst cells.

In bacterial systems, a number of expression vectors may be advantageously selected depending upon the use intended for the protein molecule being expressed. For example, when a large quantity of such an antibody is to be produced, for the generation of pharmaceutical compositions comprising an antibody of the invention, vectors which direct the expression of high levels of fusion protein products that are readily purified may be desirable. Such vectors include, but are not limited to, the *E. coli* expression vector pUR278 (Ruther et al., *EMBO*, 12:1791 (1983)), in which the coding sequence may be ligated individually into the vector in frame with the lac Z coding region so that a fusion protein is produced; pIN vectors (Inouye & Inouye, 1985, *Nucleic Acids Res.* 13:3101-3109 (1985); Van Heeke & Schuster, 1989, *J. Biol. Chem.*, 24:5503-5509 (1989)); and the like. pGEX vectors may also be used to express foreign polypeptides as fusion proteins with glutathione-S-transferase (GST). In general, such fusion proteins are soluble and can easily be purified from lysed cells by adsorption and binding to glutathione-agarose affinity matrix followed by elution in the presence of free glutathione. The pGEX vectors are designed to introduce a thrombin and/or factor Xa protease cleavage sites into the expressed polypeptide so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The protein coding sequence may be cloned individually into non-essential regions (for example, the polyhedrin gene) of the virus and placed under control of an AcNPV promoter (for example, the polyhedrin promoter).

In mammalian host cells, a number of virus based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vive recombination. Insertion into a non-essential region of the viral genome (e.g., region E1 or E3) will result in a recombinant virus that is viable and capable of expressing the antibody molecule in infected hosts (e.g., see, Logan & Shenk, *Proc. Natl. Acad. Sci. USA*, 81:355-359 (1984)). Specific initiation signals may also be required for efficient translation of inserted antibody coding sequences. These signals include the ATG initiation codon and adjacent sequences. Furthermore, the initiation codon should generally be in frame with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., *Methods in Enzymol.*, 153:51-544(1987)).

Stable expression can be used for long-term, high-yield production of recombinant proteins. For example, cell lines which stably express the protein molecule may be generated. Host cells can be transformed with an appropriately engineered vector comprising expression control elements (e.g., promoter, enhancer, transcription terminators, polyadenylation sites, etc.), and a selectable marker gene. Following the introduction of the foreign DNA, cells may be allowed to grow for 1-2 days in an enriched media, and then are switched to a selective media. The selectable marker in the recombinant plasmid confers resistance to the selection and allows cells that stably integrated the plasmid into their chromosomes to grow and form foci which in turn can be cloned and expanded into cell lines. Plasmids that encode an antibody of the invention can be used to introduce the gene/cDNA into any cell line suitable for production in culture.

A number of selection systems may be used, including, but not limited to, the herpes simplex virus thymidine kinase (Wigler et al., Cell, 11:223 (1977)), hypoxanthineguanine phosphoribosyltransferase (Szybalska & Szybalski, Proc. Natl. Acad. Sci. USA, 48:202 (1992)), and adenine phosphoribosyltransferase (Lowy et al., Cell, 22:8-17 (1980)) genes can be employed in tk-, hgprt- or aprT-cells, respectively. Also, antimetabolite resistance can be used as the basis of selection for the following genes: dhfr, which confers resistance to methotrexate (Wigler et al., Natl. Acad. Sci. USA, 77:357 (1980); O'Hare et al., Proc. Natl. Acad. Sci. USA, 78:1527 (1981)); gpt, which confers resistance to mycophenolic acid (Mulligan & Berg, Proc. Natl. Acad. Sci. USA, 78:2072 (1981)); neo, which confers resistance to the aminoglycoside G-418 (Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIB TECH 11(5):155-215 (1993)); and hygro, which confers resistance to hygromycin (Santerre et al., Gene, 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds.), Current Protocols in Human Genetics, John Wiley & Sons, NY (1994); Colberre-Garapin et al., 1981, J. Mol. Biol., 150:1, which are incorporated by reference herein in their entireties.

Once an antibody of the invention has been produced by recombinant expression, it may be purified by any method known in the art for purification of an immunoglobulin molecule, for example, by chromatography (e.g., ion exchange, affinity, particularly by affinity for the specific antigens Protein A or Protein G, and sizing column chromatography), centrifugation, differential solubility, or by any other standard technique for the purification of proteins. Further, the proteins of the present invention or fragments thereof may be fused to heterologous polypeptide sequences described herein or otherwise known in the art to facilitate purification.

Scalable Production of Antibodies

In an effort to obtain large quantities, antibodies of the invention may be produced by a scalable process (hereinafter referred to as "scalable process of the invention"). In some embodiments, antibodies may be produced by a scalable process of the invention in the research laboratory that may be scaled up to produce the antibodies of the invention in analytical scale bioreactors (for example, but not limited to 5 L, 10 L, 15 L, 30 L, or 50 L bioreactors). In other embodiments, the antibodies may be produced by a scalable process of the invention in the research laboratory that may be scaled up to produce the antibodies of the invention in production scale bioreactors (for example, but not limited to 75 L, 100 L, 150 L, 300 L, or 500 L). In some embodiments, the scalable process of the invention results in little or no reduction in production efficiency as compared to the production process performed in the research laboratory. In other embodiments, the scalable process of the invention produces antibodies at production efficiency of about 10 mg/L, about 20 m/L, about 30 mg/L, about 50 mg/L, about 75 mg/L, about 100 mg/L, about 125 mg/L, about 150 mg/L, about 175 mg/L, about 200 mg/L, about 250 mg/L, or about 300 mg/L or higher.

In other embodiments, the scalable process of the invention produces antibodies at production efficiency of at least about 10 mg/L, at least about 20 m/L, at least about 30 mg/L, at least about 50 mg/L, at least about 75 mg/L, at least about 100 mg/L, at least about 125 mg/L, at least about 150 mg/L, at least about 175 mg/L, at least about 200 mg/L, at least about 250 mg/L, or at least about 300 mg/L or higher.

In other embodiments, the scalable process of the invention produces antibodies at production efficiency from about 10 mg/L to about 300 mg/L, from about 10 mg/L to about 250 mg/L, from about 10 mg/L to about 200 mg/L, from about 10 mg/L to about 175 mg/L, from about 10 mg/L to about 150 mg/L, from about 10 mg/L to about 100 mg/L, from about 20 mg/L to about 300 mg/L, from about 20 mg/L to about 250 mg/L, from about 20 mg/L to about 200 mg/L, from 20 mg/L to about 175 mg/L, from about 20 mg/L to about 150 mg/L, from about 20 mg/L to about 125 mg/L, from about 20 mg/L to about 100 mg/L, from about 30 mg/L to about 300 mg/L, from about 30 mg/L to about 250 mg/L, from about 30 mg/L to about 200 mg/L, from about 30 mg/L to about 175 mg/L, from about 30 mg/L to about 150 mg/L, from about 30 mg/L to about 125 mg/L, from about 30 mg/L to about 100 mg/L, from about 50 mg/L to about 300 mg/L, from about 50 mg/L to about 250 mg/L, from about 50 mg/L to about 200 mg/L, from 50 mg/L to about 175 mg/L, from about 50 mg/L to about 150 mg/L, from about 50 mg/L to about 125 mg/L, or from about 50 mg/L, to about 100 mg/L.

In one embodiment, the antibodies of the invention exhibit increased stability and/or enhanced production efficiency. In one embodiment, the antibodies of the invention exhibit a production efficiency at least 2 times, at least 3 times, at least 4 times, at least 5 time, at least 6 times, at least 7 times, at least 8 times, at least 10 times or that exhibited by antibody 3.19.3.

Antibody Purification and Isolation

When using recombinant techniques, the antibodies of the invention can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Carter et al., Bio/Technology, 10:163-167 (1992) describe a procedure for isolating antibodies which are secreted into the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, ion exchange chromatography, gel electrophoresis, dialysis, and/or affinity chromatography either alone or in combination with other purification steps. The suitability of protein A as an affinity ligand depends on the species and isotype of any immunoglobulin Fc that is present in the antibody. Protein A can be used to purify antibodies that are based on human γ1, γ2, or γ4 heavy chains (Lindmark et al., J. Immunol. Methods, 62:1-13 (1983)). Protein G is recommended for all mouse isotypes and for human γ3 (Guss et al., EMBO J., 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein of the invention comprises a CH3 domain, the Bakerbond ABX resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibodies of interest and contaminants may be subjected to low pH hydrophobic interaction chromatography using an elution buffer at a pH between about 2.5-4.5, and performed at low salt concentrations (e.g., from about 0-0.25 M salt).

Recombinant protein isolation and purification can be accomplished by many art-accepted techniques exploiting the physical characteristics of the protein of interest, such as size, charge, hydrophobicity, affinity, etc. In one embodiment, the proteins of the invention are subjected to isolation/purification methods known in the art such as size exclusion chromatography, ion-exchange chromatography, and affinity chromatography. In another embodiment, the proteins of the invention are purified through protein A affinity chromatography. In another embodiment, the proteins of the invention are purified through affinity chromatography exploiting one or more binding specificities within the protein.

To ensure the stability of the antibodies of the invention, suitable assays have been developed. In one embodiment, the stability of proteins of the invention is characterized by known techniques in the art. In other embodiments, the stability of the proteins of the invention can be assessed by aggregation and/or fragmentation rate or profile. To determine the level of aggregation or fragmentation, many techniques may be used. In one embodiment, the aggregation and/or fragmentation profile may be assessed by the use of analytical ultracentrifugation (AUC), size-exclusion chromatography (SEC), high-performance size-exclusion chromatography (HPSEC), melting temperature ($T_m$), polyacrylamide gel electrophoresis (PAGE), capillary gel electrophoresis (CGE), light scattering (SLS), Fourier Transform Infrared Spectroscopy (FTIR), circular dichroism (CD), urea-induced protein unfolding techniques, intrinsic tryptophan fluorescence, differential scanning calorimetry, or 1-anilino-8-naphthalenesulfonic acid (ANS) protein binding techniques. In another embodiment, the stability of proteins of the invention is characterized by polyacrylamide gel electrophoresis (PAGE) analysis. In another embodiment, the stability of the proteins of the invention is characterized by size exclusion chromatography (SEC) profile analysis.

Another measure of stability is the relative resistance to protease degradation exhibited by a protein. In one embodiment, the stability of the proteins of the invention is characterized by a protease resistance assay. In one embodiment, the protease utilized in the protease resistance assay is a serine protease, threonine protease, cysteine protease, aspartic acid protease, metalloprotease, or a glutamic acid protease. In one embodiment, the proteins of the invention are subjected to a protease resistance assay in which the protease is trypsin, chymotrypsin, cathepsin B, D, L, or G, pepsin, papain, elastase, HIV-1 protease, chymosin, renin, plasmepsin, plasmin, carboxypeptidase E, caspase 1-10, or calpain. In another embodiment, proteins of the invention exhibit a low level of protease degradation. In some embodiments, the antibodies of the invention exhibit protease resistance in which at least 70%, at least 75%, at least 80%, at least 85%, at least 90%, at least 95% or more of the protein remains undigested after incubation with the protease under standard conditions for the protease selected.

The invention also provides methods of testing the binding of antibodies of the invention. The binding specificities of an antibody can be assessed by many different art accepted techniques such as phage display and other ELISA based technologies. In one embodiment, the binding specificities of the antibodies of the invention may be tested by any well known technique in the art. In another embodiment, the antibodies of the invention may be analyzed by any of the techniques presented in the specification. In another embodiment, the binding specificities for antibodies of the invention may be tested by an ELISA based assay.

Methods of Monitoring the Stability and Aggregation of Antibody Formulations

There are various methods available for assessing the stability of protein formulations based on the physical and chemical structures of the proteins as well as on their biological activities. For example, to study denaturation of proteins, methods such as charge-transfer absorption, thermal analysis, fluorescence spectroscopy, circular dichroism, NMR, rCGE (reducing capillary gel electrophoresis) and HPSEC (high performance size exclusion chromatography), are available (See, for example, Wang et al., 1988, J. of Parenteral Science & Technology 42(Suppl):S4-S26).

The rCGE and HPSEC are the most common and simplest methods to assess the formation of protein aggregates, protein degradation, and protein fragmentation. Accordingly, the stability of the liquid formulations of the present invention may be assessed by these methods.

The liquid formulations of the present invention comprise an antibody of the invention and exhibit low to undetectable levels of aggregation as measured by HPSEC or rCGE, that is, no more than 5%, no more than 4%, no more than 3%, no more than 2%, no more than 1%, or no more than 0.5% aggregate by weight protein, and low to undetectable levels of fragmentation, that is, 80% or higher, 85% or higher, 90% or higher, 95% or higher, 98% or higher, or 99% or higher, or 99.5% or higher of the total peak area in the peak(s) representing intact antibodies. Antibody formulations often comprise antibodies at a concentration of about 1-100 mg/ml along with an appropriate excipient. These antibody formulations may be analyzed for aggregation levels at 1, 2, 3, 4, 5, 6, 7, 14, 21, 28, 35, or 45 days or more after formulation. Also, in stability studies, antibody formulations are often incubated at 2-4° C., 10-15° C., 22-27° C., 30-37° C., or 40-42° C. to assess aggregation rates. In the case of SDS-PAGE, the density or the radioactivity of each band stained or labeled with radioisotope can be measured and the % density or % radioactivity of the band representing non-degraded antibodies of the invention can be obtained.

In one embodiment, the antibodies of the invention exhibit a lowered aggregation rate than antibody 3.19.3. In one embodiment, the antibodies of the invention exhibit an aggregation rate that is at least 10%, at least 20%, at least 30%, at least 40%, at least 50%, at least 60%, at least 70%, at least 80%, at least 90% or at least 95% lower than the aggregation rate exhibited by antibody 3.19.3 assessed under similar experimental conditions. In another embodiment, the antibodies of the invention exhibit an aggregation rate of at least 25%, at least 20%, at least 15%, at least 10%, at least 5%, at least 2%, at least 1%, or at least 0.5% as measured by the experimental conditions outlined in Example 2.

The stability of the liquid formulations of the present invention can be also assessed by any assays which measure the biological activity of the antibodies in the formulation. The biological activities of antibodies include, but are not limited to, antigen-binding activity, complement-activation activity, Fc-receptor binding activity, receptor/ligand neutralizing activity, receptor agonism or antagonism and so forth. Antigen-binding activity of the antibodies can be measured by any method known to those skilled in the art, including but not limited to ELISA, radioimmunoassay, Western blot, and the like (Also see Harlow et al., Antibodies: A Laboratory Manual, (Cold Spring Harbor Laboratory Press, 2nd ed. 1988) (incorporated by reference herein in its entirety). The purity of the liquid antibody formulations of the invention may be measured by any method well-known to one of skill in the art such as, e.g., HPSEC. The sterility of the liquid antibody formulations may be assessed as follows: sterile soybean-casein digest medium and fluid thioglycollate medium are inoculated with a test liquid antibody formulation by filtering the liquid formulation through a sterile filter having a nominal porosity of 0.45 µm. When using the Sterisure™ or Steritest™ method, each filter device is aseptically filled with approximately 100 ml of sterile soybean-casein digest medium or fluid thioglycollate medium. When using the conventional method, the challenged filter is aseptically transferred to 100 ml of sterile soybean-casein digest medium or fluid thioglycollate medium. The media are incubated at appropriate temperatures and observed three times over a 14 day period for evidence of bacterial or fungal growth.

Methods of Using Antibodies

In addition, embodiments of the invention include methods of using these antibodies for treating diseases. Anti-Ang-2 antibodies are useful for preventing Ang-2 mediated Tie2 signal transduction, thereby inhibiting angiogenesis. The mechanism of action of this inhibition may include inhibition of Ang-2/Ang-1 from binding to the receptor Tie2; inhibition of Ang-2/Ang-1 induced Tie2 signaling; Ang-2/Ang1 mediated phosphorylation of Tie-2; or enhanced clearance of Ang-2 therein lowering the effective concentration of Ang-2 for binding to Tie-2. In another embodiment, the antibodies of the invention may act through reducing circulating Ang-2/Ang-1 levels.

Diseases that are treatable through this inhibition mechanism include, but are not limited to, neoplastic diseases, such as, melanoma, small cell lung cancer, non-small cell lung cancer, glioma, hepatocellular (liver) carcinoma, glioblastoma, and cancers and tumors of the thyroid, stomach, prostate, breast, ovary, bladder, lung, uterus, kidney, colon, and pancreas, salivary gland, and colorectal.

Other embodiments of the invention include diagnostic assays for specifically determining the quantity of Ang-2 in a biological sample. The assay kit can include anti-Ang-2 antibodies along with the necessary labels for detecting such antibodies. These diagnostic assays are useful to screen for angiogenesis-related diseases including, but not limited to, neoplastic diseases, such as, melanoma, small cell lung cancer, non-small cell lung cancer, glioma, hepatocellular (liver) carcinoma, glioblastoma, and carcinoma of the thyroid, stomach, prostate, breast, ovary, bladder, lung, uterus, kidney, colon, and pancreas, salivary gland, and colorectum.

According to another aspect of the invention there is provided an antagonist of the biological activity of Angiopoietin-1 and Angiopoietin-2 wherein the antagonist binds to Angiopoietin-1 and Angiopoietin-2.

According to another aspect of the invention there is provided an antagonist of the biological activity of Angiopoietin-1 and Angiopoietin-2 wherein the antagonist is not a compound.

In one embodiment there is provided an antagonist of the biological activity of Angiopoietin-1 and Angiopoietin-2 wherein the Angiopoietin-1 antagonist activity and the Angiopoietin-2 antagonist activity is comprised within one molecule. In an alternative embodiment there is provided an antagonist wherein the Angiopoietin-1 antagonist activity and the Angiopoietin-2 antagonist activity is comprised within more than one molecule.

In one embodiment there is provided an antagonist of the biological activity of Angiopoietin-1 and Angiopoietin-2 wherein the antagonist may bind to:

I. the Tie-2 receptor,
II. Angiopoietin-1 and/or Angiopoietin-2;
III. Tie-2 receptor-Angiopoietin-1 complex; or
IV. Tie-2 receptor-Angiopoietin-2 complex,
V. or any combination of these.

In one embodiment the antagonist of the biological activity of Angiopoietin-1 and Angiopoietin-2 may bind to Angiopoietin-1 and/or Angiopoietin-2 and/or Tie-2 and thereby prevent Angiopoietin-1 and Angiopoietin-2 mediated Tie-2 signal transduction, thereby inhibiting angiogenesis. The mechanism of action of this inhibition may include;

I. binding of the antagonist to Angiopoietin-1 and inhibiting the binding of Angiopoietin-1 to its receptor, Tie-2, and/or II. binding of the antagonist to Angiopoietin-2 and inhibit the binding of Angiopoietin-2 to its receptor, Tie-2, and/or III. enhancing the clearance of Angiopoietin-1 and/or Angiopoietin-2 therein lowering the effective concentration of Angiopoietin-1 and/or Angiopoietin-2 available for binding to Tie-2, IV. or any combination of these, sufficient to antagonize the biological activity of Angiopoietin-1 and Angiopoietin-2.

Without wishing to be bound by theoretical considerations, mechanisms by which antagonism of the biological activity of Angiopoietin-1 and/or Angiopoietin-2 can be achieved include, but are not limited to, inhibition of binding of Angiopoietin-1 and/or Angiopoietin-2 to the receptor Tie-2, inhibition of Angiopoietin-1 and/or Angiopoietin-2 induced Tie-2 signaling, reduced Angiopoietin-1 and/or Angiopoietin-2 mediated Tie-2 phosphorylation or increased clearance of Angiopoietin-1 and/or Angiopoietin-2, therein reducing the effective concentration of Angiopoietin-1 and/or Angiopoietin-2.

According to another aspect of the invention there is provided a method of antagonizing the biological activity of Angiopoietin-1 and Angiopoietin-2 comprising administering an antagonist as described hereinabove. The method may include selecting an animal in need of treatment for disease-related angiogenesis, and administering to said animal a therapeutically effective dose of an antagonist of the biological activity of Angiopoietin-1 and Angiopoietin-2.

According to another aspect of the invention there is provided a method of antagonizing the biological activity of Angiopoietin-1 and Angiopoietin-2 comprising administering an antibody as described hereinabove. The method may include selecting a subject in need of treatment for disease-related angiogenesis, and administering to said subject a therapeutically effective dose of an antibody which antagonizes the biological activity of Angiopoietin-1 and Angiopoietin-2.

According to another aspect there is provided a method of treating disease-related angiogenesis in a mammal comprising administering a therapeutically effective amount of an antagonist of the biological activity of Angiopoietin-1 and Angiopoietin-2. The method may include selecting a subject in need of treatment for disease-related angiogenesis, and administering to said subject a therapeutically effective dose of an antagonist of the biological activity of Angiopoietin-1 and Angiopoietin-2.

According to another aspect there is provided a method of treating disease-related angiogenesis in a subject comprising administering a therapeutically effective amount of an antibody which antagonizes the biological activity of Angiopoietin-1 and Angiopoietin-2. The method may include selecting a subject in need of treatment for disease-related angiogenesis, and administering to said subject a therapeutically effective dose of an antibody which antagonizes the biological activity of Angiopoietin-1 and Angiopoietin-2. The antibody can be administered alone, or can be administered in combination with additional antibodies or chemotherapies, biological therapies/immunotherapies, radiation therapies, hormonal therapies, or surgery.

According to another aspect there is provided a method of treating cancer in a mammal comprising administering a therapeutically effective amount of an antagonist of the biological activity of Angiopoietin-1 and Angiopoietin-2. The method may include selecting an animal in need of treatment for cancer, and administering to said animal a therapeutically effective dose of an antagonist which antagonizes the biological activity of Angiopoietin-1 and Angiopoietin-2. The antagonist can be administered alone, or can be administered in combination with additional antibodies or chemotherapies, biological therapies/immunotherapies, radiation therapies, hormonal therapies, or surgery.

According to another aspect of the invention there is provided the use of an antibody of the invention for the manufacture of a medicament for the treatment of disease-related angiogenesis.

According to another aspect of the invention there is provided the use of an antibody which antagonizes the biological activity of Angiopoietin-1 and Angiopoietin-2 for the manufacture of a medicament for the treatment of disease-related angiogenesis.

In one embodiment the present invention is particularly suitable for use in antagonizing Angiopoietin-1 or Angiopoietin-2, in patients with a tumor which is dependent alone, or in part, on a Tie-2 receptor.

The invention also provides methods of using antibodies to ameliorate, treat, or prevent cancer or symptoms thereof. In one embodiment, methods of the invention are useful in the treatment of cancers of the head, neck, eye, mouth, throat, esophagus, chest, skin, bone, lung, colon, rectum, colorectal, stomach, spleen, kidney, skeletal muscle, subcutaneous tissue, metastatic melanoma, endometrial, prostate, breast, ovaries, testicles, thyroid, blood, lymph nodes, kidney, liver, pancreas, brain, or central nervous system. Examples of cancers that can be prevented, managed, treated or ameliorated in accordance with the methods of the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as but not limited to, glioma, astrocytoma, brain stem glioma, ependymoma, oligodendroglioma, non-glial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer, adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypemephroma, fibrosarcoma, transitional cell cancer (renal pelvis and/or ureter); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., inc., United States of America). It is also contemplated that cancers caused by aberrations in apoptosis can also be treated by the methods and compositions of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

The invention also provides methods of using antibodies to deplete a cell population. In one embodiment, methods of the invention are useful in the depletion of the following cell types: eosinophil, basophil, neutrophil, T cell, B cell, mast cell, monocytes, endothelial cell and tumor cell. Tumor cells may be cells derived from any of the cancer disorders described herein.

The antibodies of the invention and compositions comprising the same are useful for many purposes, for example, as therapeutics against a wide range of chronic and acute diseases and disorders including, but not limited to, autoimmune and/or inflammatory disorders, which include Sjogren's syndrome, rheumatoid arthritis, lupus psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation, sepsis, rheumatoid arthritis, peritonitis, Crohn's disease, reperfusion injury, septicemia, endotoxic shock, cystic fibrosis, endocarditis, psoriasis, arthritis (e.g., psoriatic arthritis), anaphylactic shock, organ ischemia, reperfusion injury, spinal cord injury and allograft rejection. Other Examples of autoimmune and/or inflammatory disorders include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, Sjogren's syndrome, psoriasis, atherosclerosis, diabetic and other retinopathies, retrolental fibroplasia, age-related macular degeneration, neovascular glaucoma, hemangiomas, thyroid hyperplasias (including Grave's disease), corneal and other tissue transplantation, and chronic inflammation, sepsis, rheumatoid arthritis, peritonitis, Crohn's disease, reperfusion injury, septicemia, endotoxic shock, cystic fibrosis, endocarditis, psoriasis, arthritis (e.g., psoriatic arthritis), anaphylactic shock, organ ischemia, reperfusion injury, spinal cord injury and allograft rejection. autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erythematosus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjogren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

In one embodiment disease-related angiogenesis may be bone and joint disease: for example, but not limited to arthritis associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathics including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic complications: vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies; pain and connective tissue remodelling of musculoskeletal disorders due to injury [for example sports injury] or disease: for example arthitides (for example rheumatoid arthritis, osteoarthritis, gout or crystal arthropathy), other joint disease (such as intervertebral disc degeneration or temporomandibular joint degeneration), bone remodelling disease (such as osteoporosis, Paget's disease or osteonecrosis), polychondritis, scleroderma, reactive arthritis, polymyalgia, mixed connective tissue disorder, spondyloarthropathies or periodontal disease (such as periodontitis).

In one embodiment disease-related angiogenesis may be selected from one of the inflammatory arthritis group of diseases including seronegative arthritis, seropositive arthritis, arthritis related to other arthropathies, ostcoarthritis or systemic lupus erythematosus (SLE). In another embodiment disease-related angiogenesis may be rheumatoid arthritis, seronegative spondyloarthropathy, arthritis related to other arthropathies or SLE. In one embodiment the seronegative spondyloarthropathy is selected from ankylosing spondylitis, psoriatic arthritis, reactive arthritis or inflammatory bowel disorder-related arthropathies. In a specific embodiment disease-related angiogenesis is rheumatoid arthritis. In another specific embodiment disease-related angiogenesis is osteoarthritis.

In some embodiments, methods of the invention can be used to reduce or inhibit disease-related angiogenesis. In some embodiments, methods of the invention comprise a reduction or inhibition of disease-related angiogenesis by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the original disease-related angiogenesis. In other embodiments, methods of the invention comprise a reduction or inhibition of disease-related angiogenesis by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the disease-related angiogenesis prior to treatment. In some embodiments, reduction in angiogenesis may be measured by the methods presented herein in the Examples, or by other methods known in the art. In specific embodiments, reduction of angiogensis may be measured by staining of biopsy samples, or by FITC-dextran accumulation in a tissue.

In some embodiments, methods of the invention can be used to reduce or inhibit angiogenesis mediated by angiogenic factors. Such factors include, but are not limited to FGF, FGF2, VEGF (and various isoforms thereof), PDGF, TGF-β, endoglin, MCP-1, and ephrins. In some embodiments, methods of the invention comprise a reduction or inhibition of angiogenesis mediated by angiogenic factors by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the level of angiogenesis mediated in the absence of treatment. In a specific embodiment, methods of the invention reduce angiogenesis induced by at least one or more angiogenic factor selected from the group consisting of FGF, FGF2, VEGF (and various isoforms thereof), PDGF, TGF-β, endoglin, MCP-1, and ephrins.

In a specific embodiment, methods of the invention can be used to reduce or inhibit FGF2-mediated angiogenesis. In some embodiments, methods of the invention comprise a reduction or inhibition of FGF2-mediated angiogenesis by at least 5%, at least 10%, at least 15%, at least 20%, at least 25%, at least 30%, at least 35% at least 40%, at least 45%, at least 50%, at least 55%, at least 60%, at least 65%, at least 70%, at least 75%, at least 80%, at least 85%, at least 90%, or at least 95% of the level of a control FGF2-mediated angiogenesis sample.

In some embodiments, methods of the invention can be used to reduce or inhibit symptoms associated with disease-related angiogenesis. In some embodiments, methods of the invention comprise a reduction or inhibition of symptoms associated with disease-related angiogenesis by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the original symptoms associated with disease-related angiogenesis. In other embodiments, methods of the invention comprise a reduction or inhibition of disease-related angiogenesis by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the symptoms associated with disease-related angiogenesis prior to treatment. Such symptoms include swelling, inflammation, fever, pain, edema, pleural effusions, anemia, malaise, morning stiffness, lows of weight, poor circulation, numbness in the limbs, and the like.

In other embodiments, methods of the invention can be used to maintain disease-related angiogenesis. In some embodiments, methods of the invention can be used to prevent disease-related angiogenesis.

The compositions and methods of the invention can be used with one or more conventional therapies that are used to prevent, manage or treat the above diseases.

In one embodiment, the invention provides a method of preventing development of cancer from a pre-cancerous state in an animal. The pre-cancerous state may be dysplasia, hyperplasia or cancer in sin (cancer in place).

In another embodiment, the invention provides a method of treating, preventing, ameliorating or managing symptoms of cancer in an animal. Symptoms of cancer may vary greatly depending on the nature of the cancer and state of progression. Symptoms associated with some cancer types may include; Bladder cancer: blood in the urine, pain or burning upon urination; frequent urination; or cloudy urine; Bone cancer: pain in the bone or swelling around the affected site; fractures in bones; weakness, fatigue; weight loss; repeated infections; nausea, vomiting, constipation, problems with urination; weakness or numbness in the legs; bumps and bruises that persist; Brain cancer: dizziness; drowsiness; abnormal eye movements or changes in vision; weakness, loss of feeling in arms or legs or difficulties in walking; fits or convulsions; changes in personality, memory or speech; headaches that tend to be worse in the morning and ease during the day, that may be accompanied by nausea or vomiting; Breast cancer: a lump or thickening of the breast; discharge from the nipple; change in the skin of the breast; a feeling of heat; or enlarged lymph nodes under the arm; Colorectal cancer: rectal bleeding (red blood in stools or black stools); abdominal cramps; constipation alternating with diarrhea; weight loss; loss of appetite; weakness; pallid complexion; Kidney cancer: blood in urine; dull ache or pain in the back or side; lump in kidney area, sometimes accompanied by high blood pressure or abnormality in red blood cell count; Leukemia: weakness, paleness; fever and flu-like symptoms; bruising and prolonged bleeding; enlarged lymph nodes, spleen, liver; pain in bones and joints; frequent infections; weight loss; night sweats; Lung cancer: wheezing, persistent cough for months; blood-streaked sputum; persistent ache in chest; congestion in lungs; enlarged lymph nodes in the neck; Melanoma: change in mole or other bump on the skin, including bleeding or change in size, shape, color, or texture; Non-Hodgkin's lymphoma: painless swelling in the lymph nodes in the neck, underarm, or groin; persistent fever; feeling of fatigue; unexplained weight loss; itchy skin and rashes; small lumps in skin; bone pain; swelling in the abdomen; liver or spleen enlargement; Oral cancer: a lump in the mouth, ulceration of the lip, tongue or inside of the mouth that does not heal within a couple of weeks; dentures that no longer fit well; oral pain, bleeding, foul breath, loose teeth, and changes in speech; Ovarian cancer: abdominal swelling; in rare cases, abnormal vaginal bleeding; digestive discomfort; Pancreatic cancer: upper abdominal pain and unexplained weight loss; pain near the center of the back; intolerance of fatty foods; yellowing of the skin; abdominal masses; enlargement of liver and spleen; Prostate cancer: urination difficulties due to blockage of the urethra; bladder retains urine, creating frequent feelings of urgency to urinate, especially at night; bladder not emptying completely; burning or painful urination; bloody urine; tenderness over the bladder; and dull ache in the pelvis or back; Stomach cancer: indigestion or heartburn; discomfort or pain in the abdomen; nausea and vomiting; diarrhea or constipation; bloating after meals; loss of appetite; weakness and fatigue; bleeding—vomiting blood or blood in the stool; Uterine cancer: abnormal vaginal bleeding, a watery bloody discharge in postmenopausal women; a painful urination; pain during intercourse; pain in pelvic area.

In another embodiment, the invention provides a method of promoting tumor regression of a cancer. In one embodiment, the method involves regression of the tumor by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% of the original tumor size. In a specific embodiment, the method comprises the elimination of the tumor by inhibition of angiogenesis.

Cell proliferation rates may be assayed by many means known in the art such as thymidine incorporation. DNA content, or cell counts. In another embodiment, the invention provides a method of inhibiting tumor cell proliferation. In one embodiment the method comprises a reduction of tumor cell proliferation. In another embodiment, the method comprises a reduction of tumor cell proliferation by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% of the original tumor cell proliferation rate.

In another embodiment the invention provides a method of depleting malignant tumor cells. In some embodiments, the method comprises depleting tumor cells resident in the primary tumor. In other embodiments, the method comprises depleting tumor cells in circulation. In other embodiments, the method comprises depleting tumor cells in a secondary site.

In another embodiment, the invention provides a method of inhibiting angiogenesis of a cancer tumor. In some embodiments, the method comprises inhibition of angiogenesis of a primary tumor site. In other embodiments, the method comprises inhibition of angiogenesis of a secondary tumor site.

The present invention provides methods of preventing, treating, managing or ameliorating an inflammatory disorder or an autoimmune disorder or one or more symptoms thereof in a subject, said methods comprising administering to said subject an antibody of the invention. In some embodiments, the present invention provides methods of preventing, treating, managing or ameliorating an inflammatory disorder or an autoimmune disorder associated with inflammation or one or more symptoms thereof in a subject, said methods comprising administering to said subject an antibody of the invention and one or more TNFα antagonists. In further embodiments, at least one of the TNF-α antagonists is a soluble TNF-α receptor such as etanercept (ENBREL™; Immunex) or a fragment, derivative or analog thereof, or an antibody that immunospecifically binds to TNF-α such as infliximab (REMICADE™; Centocor) or adalimumab (HU-MIRAL™; Abbott) a derivative, analog or antigen-binding fragment thereof. In specific embodiments the methods of the invention are performed prophylactically or therapeutically.

In some embodiments, the present invention provides methods of preventing, treating, managing or ameliorating at least one symptom associated with an inflammatory or autoimmune disorder. Such symptoms may include anemia, swelling, inflammation, edema, rash, swelling in the joints, bone synovial hyperplasia, synovitis, synovial fibrosis, periostitis, or bone mineral density (loss). In some embodiments, the present invention provides methods of treating or managing at least one symptom in an individual associated with an inflammatory or autoimmune disorder wherein said method results in a reduction, of at least 10%, at least 20%, at least 30%, at least 40%, at least 50%, at least 60%, at least 70%, at least 80%, at least 90%, or more over the severity of at least one symptom in an individual in the absence of treatment.

Combinations

The anti-angiogenic treatment defined herein may be applied as a sole therapy or may involve, in addition to the compounds of the invention, conventional surgery or radiotherapy or chemotherapy. Such chemotherapy may include one or more of the following categories of anti tumor agents:

(i) cytostatic agents such as antioestrogens (for example tamoxifen, toremifene, raloxifene, droloxifene and iodoxyfene), estrogen receptor down-regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5' reductase such as finasteride;

(ii) agents which inhibit cancer cell invasion (for example metalloproteinase inhibitors like marimastat and inhibitors of urokinase plasminogen activator receptor function);

(iii) inhibitors of growth factor function, for example such inhibitors include growth factor antibodies, growth factor receptor antibodies (for example the anti-ErbB2 antibody trastuzumab [Herceptin™] and the anti-ErbB1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N (3-chloro 4-fluorophenyl) 7-methoxy 6 (3-morpholinopropoxy)quinazolin 4-amine (gefitinib, AZD1839), N (3-ethynylphenyl) 6,7 bis(2-methoxyethoxy)quinazolin 4-amine (eriotinib, OSI 774) and 6-acrylamido N (3-chloro 4-fluorophenyl) 7 (3-morpholinopropoxy)quinazolin 4-amine (CI 1033)), for example inhibitors of the platelet derived growth factor family and for example inhibitors of the hepatocyte growth factor family;

(iv) antiangiogenic agents such as those which inhibit the effects of vascular endothelial growth factor, (for example the anti vascular endothelial cell growth factor antibody bevacizumab (Avastin®), anti-vascular endothelial growth factor receptor antibodies such anti-KDR antibodies and anti-flt1 antibodies, compounds such as those disclosed in International Patent Applications WO 97/22596, WO 97/30035, WO 97/3285, WO 98/13354, WO00/47212 and WO01/32651) and compounds that work by other mechanisms (for example linomide, inhibitors of integrin αvβ3 function and angiostatin);

(v) vascular damaging agents such as Combretastatin A4 and compounds disclosed in International Patent Applications WO 99/02166, WO 00/40529, WO 00/41669, WO 01/92224, WO 02/04434 and WO 02/08213;

(vi) antisense therapies, for example those which are directed to the targets listed above, such as ISIS 2503, an anti-ras antisense;

(vii) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (viii) immunotherapy approaches, including for example ex vivo and in vivo approaches to increase the immunogenicity of patient tumor cells, such as transfection with cytokines such as interleukin-2, interleukin-4 or granulocyte macrophage colony stimulating factor, approaches to decrease T cell anergy, approaches using transfected immune cells such as cytokine transfected dendritic cells, approaches using cytokine transfected tumor cell lines and approaches using anti idiotypic antibodies.

In one embodiment of the invention the anti-angiogenic treatments of the invention are combined with agents which inhibit the effects of vascular endothelial growth factor (VEGF), (for example the anti-vascular endothelial cell growth factor antibody bevacizumab (Avastin®), anti-vascular endothelial growth factor receptor antibodies such anti-KDR antibodies and anti-flt1 antibodies, compounds such as those disclosed in International Patent Applications WO 97/22596, WO 97/30035, WO 97/3285, WO 98/13354, WO00/47212 and WO01/32651) and compounds that work by other mechanisms (for example linomide, inhibitors of integrin avb3 function and angiostatin); In another embodiment of the invention the anti-angiogenic treatments of the invention are combined agents which inhibit the tyrosine kinase activity of the vascular endothelial growth factor receptor, KDR (for example AZD2171 or AZD6474). Additional details on AZD2171 may be found in Wedge et al (2005) Cancer Research. 65(10):4389-400. Additional details on AZD6474 may be found in Ryan & Wedge (2005) British Journal of Cancer. 92 Suppl 1:S6-13. Both publications are herein incorporated by reference in their entireties. In another embodiment of the invention the fully human antibodies 3.19.3, 3.3.2 or 5.88.3 are combined alone or in combination with Avastin®, AZD2171 or AZD6474.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically active agent within its approved dosage range.

Combinations of Ang2 Antagonists and Chemotherapy Agents

We have found that certain combinations of an antagonist of the biological activity of Angiopoietin-2 (including, but not limited to monoclonal antibody 3.19.3) and a chemotherapeutic agent produces significantly better effects on tumors as compared to use of the antagonist of the biological activity of Angiopoietin-2 or a chemotherapeutic agent used alone.

Accordingly, embodiments of the present invention provide methods of production of an anti-cancer effect in a patient, which comprises administering to said patient a therapeutically effective amount of an antagonist of the biological activity Angiopoietin-2, and/or Tie-2, before, after or simultaneously with an effective amount of a chemotherapeutic agent. In some embodiments, the method comprises selecting a patient in need of an anti-cancer effect, and administering to the patient a therapeutically effective dose of a combination of an antagonist of the biological activity of Angiopoietin-2, and/or Tie-2, and a chemotherapeutic agent.

In other embodiments, methods of the invention comprise the production of an antiangiogenic and/or vascular permeability reducing effect in a patient which comprises administering to said patient an effective amount of an antagonist of the biological activity of Angiopoietin-2, and/or Tie-2, before, after or simultaneously with an effective amount of a chemotherapeutic agent. In some embodiments, the method comprises selecting a patient in need an antiangiogenic and/or vascular permeability reducing effect, and administering to the patient a therapeutically effective dose of a combination of an antagonist of the biological activity of Angiopoietin-2, and/or Tie-2, and a chemotherapeutic agent.

In other embodiments, the invention provides a method for the treatment of disease-related angiogenesis in a patient which comprises administering to said patient an effective amount of an antagonist of the biological activity of Angiopoietin-2, and/or Tie-2, before, after or simultaneously with an effective amount of a chemotherapeutic agent. In some embodiments, the method comprises selecting a patient in need of treatment of disease-related angiogenesis, and administering to the patient a therapeutically effective dose of a combination of an antagonist of the biological activity of Angiopoietin-2, and/or Tie-2, and a chemotherapeutic agent.

In other embodiments, the invention provides a method of antagonizing the biological activity of Angiopoietin-2, and/or Tie-2 in a patient, which comprises administering to said patient in need thereof an effective amount of an antagonist of the biological activity Angiopoietin-2, and/or Tie-2, before, after or simultaneously with an effective amount of a chemotherapeutic agent.

According to a further aspect of the present invention there is provided a method of treatment comprising the administration of an effective amount of an antagonist of the biological activity of Angiopoietin-2, and/or Tie-2, or a pharmaceutically acceptable salt thereof, optionally together with a pharmaceutically acceptable excipient or carrier, and the simultaneous, sequential or separate administration of an effective amount of a chemotherapeutic agent or a pharmaceutically acceptable salt thereof, wherein the latter may optionally be administered together with a pharmaceutically acceptable excipient or carrier, to a patient in need of such therapeutic treatment.

In one embodiment the antagonist of the biological activity of Angiopoietin-2 is an antibody. In further embodiments, the antagonist of Angiopoietin-2 is a monoclonal antibody. In yet further embodiments, the antagonist of Angiopoietin-2 is a fully human monoclonal antibody. In some embodiments the fully human monoclonal antibody is selected from any one of: 3.31.2, or 5.16.3, or 5.86.1, or 5.88.3, or 3.3.2, or 5.103.1, or 5.101.1, or 3.19.3, or 5.28.1, or 5.78.3, MEDI1/5, MEDI2/5, MEDI3/5, MEDI6/5, or MEDI4/5. In further embodiments, the fully human monoclonal antibody binds to the same epitope as any one of fully human monoclonal antibody: 3.31.2, 5.16.3, 5.86.1, 5.88.3, 3.3.2, 5.103.1, 5.101.1, 3.19.3, 5.28.1, 5.78.3 which are disclosed in International Publication Number WO2006/068953 or AMG 386 (Amgen, International Publication Number WO0200330833).

In another embodiment the antagonist of the biological activity of Angiopoietin-2 is a peptibody such as the peptibody (AMG386) as disclosed in International Publication Number WO02003057134.

In another embodiment the antagonist of the biological activity of Tie-2 is an antibody. In further embodiments, the Tie-2 antibody is a monoclonal, humanized, or fully human antibody.

In one embodiment a chemotherapeutic agent comprises alkylating agents (for example cisplatin, carboplatin, oxaliplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, gemeitabine, capecitabine, methotrexate, pemetrexed (Alimta), cytosine arabinoside and hydroxyurea, or, for example, one of the antimetabolites disclosed in European Patent Application No. 562734 such as (2S)-2-{o-fluoro-p-[N-(2,7-dimethyl-4-oxo-3,4-dihydroquinazolin-6-ylmethyl)-N-(prop-2-ynyl)amino] benzamido}-4-(tetrazol-5-yl)butyric acid); pharmaceutical combinations which comprise an alkylating agent and an antimetabolite (for example Folfox (a combination of fluorouracil (5FU), leucovorin and oxaliplatin)); antitumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); topoisomerase inhibitors (for example epipodophyllotoxins like etoposide and teniposide, irinotecan, amsacrine, topotecan and camptothecin); or proteasome inhibitors (for example bortezomib). In one embodiment there is provided a combination of the invention additionally comprising Folfox.

In another embodiment a chemotherapeutic agent comprises docetaxel, and other antimitotic agents (for example vinca alkaloids like vincristine, vinblastine, vindesine and vinorelbine and taxoids like taxol and taxotere); 5-fluorouracil, gemcitabine and other antimetabolites (for example antifolates such as fluoropyrimidines, tegafur, raltitrexed, capecitabine, methotrexate, pemetrexed (Alimta), cytosine arabinoside and hydroxyurea); irinotecan and other topoisomerase inhibitors (for example etoposide topotecan, camptothecin teniposide, and amsacrine); oxaliplatin and other alkylating or DNA binding agents (for example cisplatin, and carboplatin). In one embodiment there is provided a combination of the invention additionally comprising Folfox.

In another embodiment a chemotherapeutic agent comprises Eg5 inhibitors, for example AZD4877.

Combinations of Ang2 Antagonists and CSF1/CSFR1 Antagonists

The present invention also provides pharmaceutical combinations comprising an antagonist of the biological activity of Angiopoietin-2, and/or Tie-2, and an antagonist of the biological activity of CSF1R, and/or CSF1, and uses of such combinations.

According to one aspect of the invention there is provided a pharmaceutical combination comprising an antagonist of the biological activity of Angiopoietin-2, and/or Tie-2 and an antagonist of the biological activity of CSF1R, and/or CSF1.

In one embodiment the antagonist of the biological activity of Angiopoietin-2 is an antibody. In further embodiments, the antagonist of Angiopoietin-2 is a monoclonal antibody. In yet further embodiments, the antagonist of Angiopoietin-2 is a fully human monoclonal antibody. In some embodiments the fully human monoclonal antibody is selected from any one of; 3.31.2, or 5.16.3, or 5.86.1, or 5.88.3, or 3.3.2, or 5.103.1, or 5.101.1, or 3.19.3, or 5.28.1, or 5.78.3, MEDI1/5, MEDI2/5, MEDI3/5, MEDI6/5, or MEDI4/5. In further embodiments, the fully human monoclonal antibody binds to the same epitope as any one of fully human monoclonal antibody; 3.31.2, 5.16.3, 5.86.1, 5.88.3, 3.3.2, 5.103.1, 5.101.1, 3.19.3, 5.28.1, 5.78.3 which are disclosed in International Publication Number WO2006/068953 or AMG 386 (Amgen, International Publication Number WO200330833).

In another embodiment there is provided a pharmaceutical combination as described above, wherein the antagonist of the biological activity of Tie-2 is an antibody. In one embodiment the antagonist is a monoclonal antibody. In one embodiment the antagonist is a fully human monoclonal antibody.

In another embodiment there is provided a pharmaceutical combination as described above, wherein the antagonist of the biological activity of CSF1R is an antibody. In one embodiment the antagonist is a monoclonal antibody. In one embodiment the antagonist is a fully human monoclonal antibody.

In another embodiment there is provided a pharmaceutical combination as described above, wherein the antagonist of the biological activity of CSF1 is an antibody. In one embodiment the antagonist is a monoclonal antibody. In one embodiment the antagonist is monoclonal antibody PD-360324 (Pfizer). In one embodiment the antagonist is a fully human monoclonal antibody.

In another embodiment there is provided a pharmaceutical combination as described above, wherein the antagonist of the biological activity of CSF1R is a compound, or a pharmaceutically acceptable salt thereof. In one embodiment the antagonist is a tyrosine kinase inhibitor, or a pharmaceutically acceptable salt thereof. In one embodiment the tyrosine kinase inhibitor, or a pharmaceutically acceptable salt thereof, is selected from the compounds disclosed in International Patent Application Nos. WO2004/004985, WO2007/119046, WO2008/056148 or WO2008/090353, ABT-869 (Abbott), Sutent (Pfizer), KI-20227 (Kirin Brewery), CYC-10268 (Cytopia), YM-359445 (Astellas Pharma), PLX-647 (Phenomix Corp./Plexxikon), JNJ-27301937 (Johnson & Johnson), GW-2580 (GlaxoSmithKline) or any of the compounds disclosed in US Provisional Application Numbers US05/0131022, US05/0113566, International Patent Application Numbers WO2004/096795 WO2005/009967, WO2006/047277, WO2006/047504 or WO2003/093238.

In one embodiment the tyrosine kinase inhibitor, or a pharmaceutically acceptable salt thereof, is selected from the compounds disclosed in International Patent Application No. WO2004/004985, WO2007/119046, WO 2008/090353, WO 2008/056148, WO 2007/119046, WO 2007/071955 each of which are incorporated by reference in their entireties.

In another embodiment the antagonist of the biological activity of CSF1R is selected from any one of:
2-chloro-N-pyridin-3-yl-5-{[3-(trifluoromethyl)benzoyl]amino}benzamide;
2-chloro-N-(5-fluoropyridin-3-yl)-5-{[3-(trifluoromethyl)benzoyl]amino}benzamide;
2-chloro-N-(5-fluoropyridin-3-yl)-5-{[3-fluoro-5-(trifluoromethyl)benzoyl]amino}-benzamide;
2-methyl-N-pyridin-3-yl-5-{[3-(trifluoromethyl)benzoyl]amino}benzamide;
5-{[3-fluoro-5-(trifluoromethyl)benzoyl]amino}-2-methyl-N-pyridin-3-ylbenzamide;
2-chloro-5-[(3-cyclopropylbenzoyl)amino]-N-pyridin-3-ylbenzamide;
2-chloro-5-[(3-chlorobenzoyl)amino]-N-pyridin-3-ylbenzamide;
5-[(3-chloro-5-fluorobenzoyl)amino]-2-methyl-N-pyridin-3-ylbenzamide;
5-[(3-cyclopropyl-5-fluorobenzoyl)amino]-2-methyl-N-pyridin-3-ylbenzamide;
5-[(3-chlorobenzoyl)amino]-2-methyl-N-pyridin-3-ylbenzamide;
5-{[3-(1-cyano-1-methylethyl)benzoyl]amino}-2-methyl-N-(2-methyl-1,3-thiazol-5-yl)benzamide;
2-chloro-N-1,3-thiazol-5-yl-5-{[3-(trifluoromethyl)benzoyl]amino}benzamide;
2-chloro-5-[(3-chlorobenzoyl)amino]-N-1,3-thiazol-5-ylbenzamide;
2-chloro-5-[(3,5-dimethylbenzoyl)amino]-N-1,3-thiazol-5-ylbenzamide;
5-{[3-(1-cyano-1-methylethyl)benzoyl]amino}-2-methyl-N-1,3-thiazol-5-ylbenzamide;
2-methyl-N-(2-methyl-1,3-thiazol-5-yl)-5-{[3-(trifluoromethyl)benzoyl]amino}benzamide;
2-chloro-5-[(3-chlorobenzoyl)amino]-N-(2-methyl-1,3-thiazol-5-yl)benzamide;
2-chloro-5-[(3,5-dimethylbenzoyl)amino]-N-(2-methyl-1,3-thiazol-5-yl)benzamide;
2-chloro-N-(2-methyl-1,3-thiazol-5-yl)-5-{[3-(trifluoromethyl)benzoyl]amino}benzamide;
2-chloro-5-{[3-fluoro-5-(trifluoromethyl)benzoyl]amino}-N-(2-methyl-1,3-thiazol-5-yl)benzamide;
5-[(5-{[3-(1-cyano-1-methylethyl)benzoyl]amino}-2-methylbenzoyl)amino]-methyl-N-1,3-thiazole-2-carboxamide;
5-{[3-fluoro-5-(trifluoromethyl)benzoyl]amino}-2-methyl-N-(2-methyl-1,3-thiazol-5-yl)benzamide;
5-[(3-chloro-5-fluorobenzoyl)amino]-2-methyl-N-(2-methyl-1,3-thiazol-5-yl)benzamide;
5-[(3-cyclopropyl-5-fluorobenzoyl)amino]-2-methyl-N-(2-methyl-1,3-thiazol-5-yl)benzamide;
5-[(3-chlorobenzoyl)amino]-2-methyl-N-(2-methyl-1,3-thiazol-5-yl)benzamide;
5-[3,4-dichlorobenzoyl)amino]-2-methyl-N-(2-methyl-1,3-thiazol-5-yl)benzamide;
5-[(3-cyclopropylbenzoyl)amino]-2-methyl-N-(2-methyl-1,3-thiazol-5-yl)benzamide;
5-[(3,5-dimethylbenzoyl)amino]-2-methyl-N-(2-methyl-1,3-thiazol-5-yl)benzamide;
2-methyl-5-[(3-methylbenzoyl)amino]-N-(2-methyl-1,3-thiazol-5-yl)benzamide;
2,6-dichloro-N-(4-methyl-3-{[(2-methyl-1,3-thiazol-5-yl)amino]carbonyl}phenyl)isonicotinamide;
2-methyl-5-{[(3-methylcyclohexyl)carbonyl]amino}-N-(2-methyl-1,3-thiazol-5-yl)benzamide;
2-methyl-N-(2-methyl-1,3-thiazol-5-yl)-5-(pentanoylamino)benzamide;
2-methyl-5-[(4-methylhexanoyl)amino]-N-(2-methyl-1,3-thiazol-5-yl)benzamide;
4-[(2,4-difluorophenyl)amino]-7-ethoxy-6-(4-methylpiperazin-1-yl)quinoline-3-carboxamide;
4-[(2,3-dichlorophenyl)amino]-7-ethoxy-6-(4-methylpiperazin-1-yl)quinoline-3-carboxamide;
7-ethoxy-4-[(2-fluoro-5-methylphenyl)amino]-6-(4-isopropylpiperazin-1-yl)quinoline-3-carboxamide;
4-[(3-chloro-2-fluorophenyl)amino]-7-ethoxy-6-(4-methylpiperazin-1-yl)quinoline-3-carboxamide;
7-ethoxy-4-[(2-fluoro-5-methylphenyl)amino]-6-(4-methylpiperazin-1-yl)quinoline-3-carboxamide;
7-ethoxy-4-[(2-fluoro-4-methylphenyl)amino]-6-(4-methylpiperazin-1-yl)quinoline-3-carboxamide;
4-[(2,4-difluorophenyl)amino]-7-(2-methoxyethoxy)-6-(4-methylpiperazin-1-yl)quinoline-3-carboxamide;
4-[(2-fluoro-4-methylphenyl)amino]-7-(2-methoxyethoxy)-6-(4-methylpiperazin-1-yl)quinoline-3-carboxamide;

4-[(2-fluoro-5-methylphenyl)amino]-7-(2-methoxyethoxy)-6-(4-methylpiperazin-1-yl)quinoline-3-carboxamide;
4-[(2-fluoro-4-methylphenyl)amino]-6-(4-isopropylpiperazin-1-yl)-7-(2-methoxyethoxy)quinoline-3-carboxamide;
7-ethoxy-4-[(2-fluoro-4-methylphenyl)amino]-6-(1-methylpiperidin-4-yl)quinoline-3-carboxamide;
4-[(2,4-difluorophenyl)amino]-7-ethoxy-6-(1-methylpiperidin-4-yl)quinoline-3-carboxamide;
4-[(2,4-difluoropbenyl)amino]-7-ethoxy-6-(1-isopropylpiperidin-4-yl)quinoline-3-carboxamide;
7-ethoxy-4-[(2-fluoro-4-methylphenyl)amino]-6-(1-isopropylpiperidin-4-yl)quinoline-3-carboxamide;
4-[(2-fluoro-4-methylphenyl)amino]-7-methoxy-6-(1-methylpiperidin-4-yl)quinoline-3-carboxamide;
4-[(3-chloro-2-fluorophenyl)amino]-7-methoxy-6-(1-methylpiperidin-4-yl)quinoline-3-carboxamide;
4-[(2,4-difluorophenyl)amino]-7-methoxy-6-(1-methylpiperidin-4-yl)quinoline-3-carboxamide;
4-[(2-fluoro-4-methylphenyl)amino]-6-(1-isopropylpiperidin-4-yl)-7-methoxyquinoline-3-carboxamide;
4-[(2,4-difluorophenyl)amino]-6-(1-isopropylpiperidin-4-yl)-7-methoxyquinoline-3-carboxamide; and
4-[(3-chloro-2-fluorophenyl)amino]-6-(1-isopropylpiperidin-4-yl)-7-methoxyquinoline-3-carboxamide;
7-Ethoxy-4-[(2-fluoro-4-methyl-phenyl)amino]-6-(4-methylpiperazin-1-yl)cinnoline-3-carboxamide;
4-(2-Fluoro-4-methylphenylamino)-7-methoxy-6-(4-methylpiperazin-1-yl)cinnoline-3-carboxamide;
4-[(2,4-Difluorophenyl)amino]-7-methoxy-6-(4-methylpiperazin-1-yl)cinnoline-3-carboxamide;
6-[(3R,5S)-3,5-Dimethylpiperazin-1-yl]-4-[(2-fluoro-4-methylphenyl)amino]-7-methoxycinnoline-3-carboxamide;
4-[(2-Fluoro-4-methylphenyl)amino]-6-[4-(2-hydroxyethyl)piperazin-1-yl]-7-methoxycinnoline-3-carboxamide;
7-Ethoxy-4-[(2-fluoro-4-methylphenyl)amino]-6-[4-(2-hydroxyethyl)piperazin-1-yl]cinnoline-3-carboxamide;
4-[(3-Chloro-2-fluorophenyl)amino]-6-[(3R,5S)-3,5-dimethylpiperazin-1-yl]-7-methoxycinnoline-3-carboxamide;
4-[(2-Fluoro-4-methylphenyl)amino]-6-(1-isopropylpiperidin-4-yl)-7-methoxycinnoline-3-carboxamide hydrochloride;
4-[(2-Fluoro-4-methylphenyl)amino]-6-[1-(2-hydroxyethyl)piperidin-4-yl]-7-methoxycinnoline-3-carboxamide; and
4-[(2-Fluoro-4-methylphenyl)amino]-6-{4-[(2R)-2-hydroxypropanoyl]piperazin-1-yl}-7-methoxycinnoline-3-carboxamide
or a pharmaceutically acceptable salt thereof.

In another embodiment there is provided a pharmaceutical combination as described above, wherein the antagonist of the biological activity of CSF1 is a compound, or a pharmaceutically acceptable salt thereof.

In another embodiment there is provided a pharmaceutical combination as described above, wherein the antagonist of the biological activity of Angiopoietin-2 is a compound, or a pharmaceutically acceptable salt thereof.

In another embodiment there is provided a pharmaceutical combination as described above, wherein the antagonist of the biological activity of Tie-2 is a compound, or a pharmaceutically acceptable salt thereof. In one embodiment the antagonist is a tyrosine kinase inhibitor, or a pharmaceutically acceptable salt thereof. In one embodiment the tyrosine kinase inhibitor, or a pharmaceutically acceptable salt thereof, is selected from any of the compounds disclosed in International Patent Application Numbers WO2004/013141, WO2004/058776, WO2005/060970 or WO2005/060969, or is GW697465X (GSK), CP-547632 (Pfizer), CE-245677 (Pfizer) or CGI1631 (Cellular Genomics).

In another aspect of the present invention there is provided a pharmaceutical combination of the present invention for use as a medicament comprising an antagonist of the biological activity of Angiopoietin-2, and/or Tie-2, and an antagonist of the biological activity of CSF1R, and/or CSF1, for use simultaneously, serially or separately.

In another aspect of the present invention there is provided a method of antagonizing Angiopoietin-2 and/or Tie-2, and antagonizing CSF1R, and/or CSF1, in a patient, which comprises administering to the patient a therapeutically effective amount of a pharmaceutical combination or another composition of the present invention. In one embodiment the method additionally comprises selecting a patient in need of inhibition of Angiopoietin-2 and/or Tie-2, and inhibition of CSF1R, and/or CSF1, and administering to the patient a therapeutically effective dose of a pharmaceutical combination or another pharmaceutical composition as described herein.

In one embodiment the present invention is particularly suitable for use in antagonizing the biological activity of Angiopoietin-2, and/or Tie-2, and the biological activity of CSF1R, and/or CSF1, in patients with a tumor which is dependent alone, or in part, on Angiopoietin-2, and/or Tie-2, and CSF1R, and/or CSF1.

In one embodiment the method or use of the invention may be administered with one or more of the following agents, by way of the simultaneous, sequential or separate administration with of the antagonist of the biological activity of Angiopoietin-2, and/or Tie-2, an antagonist of cytokine function, (e.g. an agent which act on cytokine signalling pathways such as a modulator of the SOCS system), such as an alpha-, beta-, and/or gamma-interferon; modulators of insulin-like growth factor type 1 (IGF-1), its receptors and associated binding proteins; interleukins (IL) e.g. one or more of IL-1 to 33, and/or an interleukin antagonist or inhibitor such as anakinra; inhibitors of receptors of interleukin family members or inhibitors of specific subunits of such receptors; a tumor necrosis factor alpha (TNF-α) inhibitor such as an anti-TNF monoclonal antibody (for example infliximab; adalimumab, and/or CDP-870), and/or a TNF receptor antagonist e.g. an immunoglobulin molecule (such as etanercept) and/or a low-molecular-weight agent such as pentoxyfylline; a modulator of B cells, e.g. a monoclonal antibody targeting B-lymphocytes (such as CD20 (rituximab) or MRA-aIL16R) or T-lymphocytes (e.g. CTLA4-Ig, HuMax Il-15 or Abatacept); a modulator that inhibits osteoclast activity, for example an antibody to RANKL; a modulator of chemokine or chemokine receptor function such as an antagonist of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 and CXCR6 (for the C—X—C family) and $CX_3CR1$ for the C—$X_3$—C family; antiangiogenic agents such as those which inhibit the effects of vascular endothelial growth factor, [for example the anti-vascular endothelial cell growth factor antibody bevacizumab (Avastin®) and VEGF receptor tyrosine kinase inhibitors such as 4-(4-bromo-2-fluoroanilino)-6-methoxy-7-(1 methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856, WO 98/13354, WO00/47212 and WO01/32651 and compounds that work by other mechanisms (for example linomide, inhibitors of integrin αvβ3 function and angiostatin)] or colony stimulating factor 1 (CSF1) or CSF1 receptor; an inhibitor of matrix metalloproteases (MMPs), i.e., one or more of the stromelysins, the collagenases, and the gelatinases, as well as aggrecanase; especially collagenase-1 (MMP1), collagenase-2 (MMP8), collagenase-3 (MMP13), stromelysin-1 (MMP3), stromelysin-2 (MMP10), and/or stromelysin-3 (MMP11) and/or MMP9 and/or MMP12, e.g. an agent such as doxycycline; a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; N-(5-substituted)-thiophene-2-alkylsulfonamides; 2,6-di-tert-butylphenolhydrazones; methoxytetrahydropyrans such as Zeneca ZD-2138; the compound SB-210661; a pyridinyl-substituted 2-cyanonaphthalene compound such as L-739,010; a 2-cyanoquinoline compound such as L-746,530; indole and/or a quinoline compound such as MK-591, MK-886, and/or BAY×1005; a receptor antagonist for leukotrienes (LT) B4, LTC4, LTD4, and LTE4, selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY×7195; a phosphodiesterase (PDE) inhibitor such as a methylxanthanine, e.g. theophylline and/or aminophylline; and/or a selective PDE isoenzyme inhibitor e.g. a PDE4 inhibitor and/or inhibitor of the isoform PDE4D, and/or an inhibitor of PDE5; a histamine type 1 receptor antagonist such as cetirizine, loratadine, desloratadine, fexofenadine, acrivastine, terfenadine, astemizole, azelastine, levocabastine, chlorpheniramine, promethazine, cyclizine, and/or mizolastine (generally applied orally, topically or parenterally); a proton pump inhibitor (such as omeprazole) or gastroprotective histamine type 2 receptor antagonist; an antagonist of the histamine type 4 receptor, an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride, and ethylnorepinephrine hydrochloride; an anticholinergic agent, e.g. a muscarinic receptor (M1, M2, and M3) antagonist such as atropine, hyoscine, glycopyrrrolate, ipratropium bromide, tiotropium bromide, oxitropium bromide, pirenzepine, and telenzepine; a beta-adrenoceptor agonist (including beta receptor subtypes 1-4) such as isoprenaline, salbutamol, formoterol, salmeterol, terbutaline, orciprenaline, bitolterol mesylate, and/or pirbuterol, e.g. a chiral enantiomer thereof; a chromone, e.g. sodium eromoglycate and/or nedocromil sodium; a glucocorticoid, such as flunisolide, triamcinolone acetonide, beclomethasone dipropionate, budesonide, fluticasone propionate, ciclesonide, and/or mometasone furoate; an agent that modulates nuclear hormone receptors such as a PPAR; an immunoglobulin (Ig) or Ig preparation or an antagonist or antibody modulating Ig function such as anti-IgE (e.g. omalizumab); other systemic or topically-applied anti-inflammatory agent, e.g. thalidomide or a derivative thereof, a retinoid, dithranol, and/or calcipotriol; pharmaceutical combinations of aminosalicylates and sulfapyridine such as sulfasalazine, mesalazine, balsalazide, and olsalazine; and immunomodulatory agents such as the thiopurines, and corticosteroids such as budesonide; an antibacterial agent e.g. a penicillin derivative, a tetracycline, a macrolide, a beta-lactam, a fluoroquinolone, metronidazole, and/or an inhaled aminoglycoside; and/or an antiviral agent e.g. acyclovir, famciclovir, valaciclovir, ganciclovir, cidofovir; amantadine, rimantadine; ribavirin; zanamavir and/or oseltamavir; a protease inhibitor such as indinavir, nelfinavir, ritonavir, and/or saquinavir, a nucleoside reverse transcriptase inhibitor such as didanosine, lamivudine, stavudine, zalcitabine, zidovudine; a non-nucleoside reverse transcriptase inhibitor such as nevirapine, efavirenz; a cardiovascular agent such as a calcium channel blocker, beta-adrenoceptor blocker, angiotensin-converting enzyme (ACE) inhibitor, angiotensin-2 receptor antagonist; lipid lowering agent such as a statin, and/or fibrate; a modulator of blood cell morphology such as pentoxyfylline; a thrombolytic, and/or an anticoagulant e.g. a platelet aggregation inhibitor; a CNS agent such as an antidepressant (such as sertraline), anti-Parkinsonian drug (such as deprenyl, L-dopa, ropinirole, pramipexole, MAOB inhibitor such as selegine and rasagiline, comP inhibitor such as tasmar, A-2 inhibitor, dopamine reuptake inhibitor, NMDA antagonist, nicotine agonist, dopamine agonist and/or inhibitor of neuronal nitric oxide synthase), and an anti-Alzheimer's drug such as donepezil, rivastigmine, tacrine, COX-2 inhibitor, propentofylline or metrifonate; an agent for the treatment of acute and chronic pain, e.g. a centrally or peripherally-acting analgesic such as an opioid analogue or derivative, carbamazepine, phenytoin, sodium valproate, amitryptyline or other antidepressant agent, paracetamol, or non-steroidal anti-inflammatory agent; a parenterally or topically-applied (including inhaled) local anaesthetic agent such as lignocaine or an analogue thereof; an anti-osteoporosis agent e.g. a hormonal agent such as raloxifene, or a biphosphonate such as alendronate; (i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitors including VLA-4 antagonist; (vi) a cathepsin; (vii) a kinase inhibitor e.g. an inhibitor of tyrosine kinases (such as Btk, Itk, Jak3 MAP examples of inhibitors might include Gefitinib, Imatinib mesylate), a serine/threonine kinase (e.g. an inhibitor of MAP kinase such as p38, JNK, protein kinases A, B and C and IKK), or a kinase involved in cell cycle regulation (e.g. a cylin dependent kinase); (viii) a glucose-6 phosphate dehydrogenase inhibitor; (ix) a kinin-B$_1$- and/or B$_2$-receptor antagonist; (x) an anti-gout agent, e.g., colchicine; (xi) a xanthine oxidase inhibitor, e.g., allopurinol; (xii) a uricosuric agent, e.g., probenecid, sulfinpyrazone, and/or benzbromarone; (xiii) a growth hormone secretagogue; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) a tachykinin NK$_1$. and/or NK$_3$. receptor antagonist such NKP-608C, SB-233412 (talnetant), and/or D-4418; (xx) an elastase inhibitor e.g. UT-77 and/or ZD-0892; (xxi) a TNF-alpha converting enzyme inhibitor (TACE); (xxii) induced nitric oxide synthase (iNOS) inhibitor or (xxiii) a chemoattractant receptor-homologous molecule expressed on TH2 cells, (such as a CRTH2 antagonist) (xxiv) an inhibitor of a P38 (xxv) agent modulating the function of Toll-like receptors (TLR) and (xxvi) an agent modulating the activity of purinergic receptors such as P2X7; (xxvii) an inhibitor of transcription factor activation such as NFkB, API, and/or STATS; Non-steroidal anti-inflammatory agents (hereinafter NSAIDs) including non-selective cyclo-oxygenase (COX)-1/COX-2 inhibitors whether applied topically or systemically (such as piroxicam, diclofenac, propionic acids such as naproxen, flurbiprofen, fenoprofen, ketoprofen and ibuprofen, fenamates such as mefenamic acid, indomethacin, sulindac, azapropazone, pyrazolones such as phenylbutazone, salicylates such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intravenous, or intra-articular routes); methotrexate, leflunomide; hydroxychloroquine, d-penicillamine, auranofin or other parenteral or oral gold preparations; analgesics; diacerein; intra-articular therapies such as hyaluronic acid derivatives; and nutritional supplements such as glucosamine.

In some embodiments, the method or use of the invention may comprise administration of an agent that antagonizes TNF-α. Any TNF-α antagonist well-known to one of skill in the art can be used in the compositions and methods of the invention. Non-limiting examples of TNF-α antagonists include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that immunospecifically bind to TNF-α, nucleic acid molecules (e.g., antisense molecules or triple helices), organic molecules, inorganic molecules, and small molecules that blocks, reduces, inhibits or neutralizes the function, activity and/or expression of TNF-α. In various embodiments, a TNF-α antagonist reduces the function, activity and/or expression of TNF-α by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS).

Examples of antibodies that immunospecifically bind to TNF-α include, but are not limited to, infliximab (REMICADE™; Centocor), adalimumab (HUMIRA™; Abbott Laboratories), D2E7 (Abbott Laboratories/Knoll Pharmaceuticals Co., Mt. Olive, N.J.), CDP571 which is also known as HUMICADE™ and CDP-870 (both of Celltech/Pharmacia, Slough, U.K.), and TN3-19.12 (Williams et al., 1994, Proc. Natl. Acad. Sci. USA 91: 2762-2766; Thorbecke et al., 1992, Proc. Natl. Acad. Sci. USA 89:7375-7379). The present invention also encompasses the use of antibodies that immunospecifically bind to TNF-α disclosed in the following U.S. patents in the compositions and methods of the invention: U.S. Pat. Nos. 5,136,021; 5,147,638; 5,223,395; 5,231,024; 5,334,380; 5,360,716; 5,426,181; 5,436,154; 5,610,279; 5,644,034; 5,656,272; 5,658,746; 5,698,195; 5,736,138; 5,741,488; 5,808,029; 5,919,452; 5,958,412; 5,959,087; 5,968,741; 5,994,510; 6,036,978; 6,114,517; and 6,171,787; each of which are herein incorporated by reference in their entirety. Examples of soluble TNF-α receptors include, but are not limited to, sTNF-R1 (Amgen), etanercept (ENBREL™: Immunex) and its rat homolog RENBREL™, soluble inhibitors of TNF-α derived from TNTrI, TNFrII (Kohno et al., 1990, Proc. Natl. Acad. Sci. USA 87:8331-8335), and TNF-α Inh (Seckinger et al, 1990, Proc. Natl. Acad. Sci. USA 87:5188-5192).

In one embodiment, a TNF-α antagonist used in the compositions and methods of the invention is a soluble TNF-α receptor. In a specific embodiment, a TNF-α antagonist used in the compositions and methods of the invention is etanercept (ENBREL™; Immunex) or a fragment, derivative or analog thereof. In another embodiment, a TNF-α antagonist used in the compositions and methods of the invention is an antibody that immunospecifically binds to TNF-α. In a specific embodiment, a TNT-α antagonist used in the compositions and methods of the invention is infliximab (REMICADE™; Centocor) a derivative, analog or antigen-binding fragment thereof. In another specific embodiment, a TNF-α antagonist used in the compositions and methods of the invention is adalimumnab (HUMIRA™; Abbott Laboratories) a derivative, analog or antigen-binding fragment thereof.

Other TNF-α antagonists encompassed by the invention include, but are not limited to, IL-10, which is known to block TNF-α production via interferon γ-activated macrophages (Oswald et al. 1992, Proc. Natl. Acad. Sci. USA 89:8676-8680), TNFR-IgG (Ashkenazi et al., 1991, Proc. Natl. Acad. Sci. USA 88:10535-10539), the murine product TBP-1 (Scrono/Yeda), the vaccine CytoTAb (Protherics), antisense molecule 104838 (ISIS), the peptide RDP-58 (SangStat), thalidomide (Celgene), CDC-801 (Celgene), DPC-333 (Dupont), VX-745 (Vertex), AGIX-4207 (AtheroGenics), ITF-2357 (Italfarmaco), NPI-13021-31 (Nereus), SCIO-469 (Scios), TACE targeter (Immunix/AHP), CLX-120500 (Calyx), Thiazolopyrim (Dynavax), auranofin (Ridaura) (SmithKline Beecham Pharmaceuticals), quinacrine (mepacrine dichlorohydrate), tenidap (Enablex), Melanin (Large Scale Biological), and anti-p38 MAPK agents by Uriach.

Nucleic acid molecules encoding proteins, polypeptides, or peptides with TNF-α antagonist activity or proteins, polypeptides, or peptides with TNF-α antagonist activity can be administered to a subject with an inflammatory or autoimmune disease in accordance with the methods of the invention. Further, nucleic acid molecules encoding derivatives, analogs, fragments or variants of proteins, polypeptides, or peptides with TNF-α antagonist activity, or derivatives, analogs, fragments or variants of proteins, polypeptides, or peptides with TNF-α antagonist activity can be administered to a subject with an inflammatory or autoimmune disease in accordance with the methods of the invention. Such derivatives, analogs, variants and fragments retain the TNF-α antagonist activity of the full-length wild-type protein, polypeptide, or peptide.

Proteins, polypeptides, or peptides that can be used as TNF-α antagonists can be produced by any technique well-known in the art or described herein. Proteins, polypeptides or peptides with TNF-α antagonist activity can be engineered so as to increase the in vivo half-life of such proteins, polypeptides, or peptides utilizing techniques well-known in the art or described herein. Preferably, agents that are commercially available and known to function as TNF-α antagonists are used in the compositions and methods of the invention. The TNF-α antagonist activity of an agent can be determined in vitro and/or in vivo by any technique well-known to one skilled in the art.

In one embodiment the method or use of the invention may comprise administration of an antibody that is an antagonist of the biological activity of Angiopoietin-2, and/or Tie-2 as an immuno-conjugate with any one of the agents listed above.

Pharmaceutical Compositions

In another aspect, the present invention provides a composition, for example, but not limited to, a pharmaceutical composition, containing one or more antibodies of the present invention, formulated together with a pharmaceutically acceptable carrier. Such compositions may include one or a combination of, for example, but not limited to two or more different antibodies of the invention. For example, a pharmaceutical composition of the invention may comprise a combination of antibodies that bind to different epitopes on the target antigen or that have complementary activities.

Pharmaceutical compositions of the invention also can be administered in combination therapy, such as, combined with other agents. For example, the combination therapy can include an antibody of the present invention combined with at least one other therapy wherein the therapy may be surgery, immunotherapy, chemotherapy, radiation treatment, or drug therapy.

The pharmaceutical compounds of the invention may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, selected methods of preparation are vacuum drying and freeze-drying (lyophilization) that yield a powder of the active ingredient plus any additional desired ingredient from a previously sterile-filtered solution thereof.

In one embodiment the compositions of the invention are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight it is advantageous to remove even trace amounts of endotoxin. In one embodiment, endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg. In another embodiment, endotoxin and pyrogen levels in the composition are less then about 10 EU/mg, or less then about 5 EU/mg, or less then about 1 EU/mg, or less then about 0.1 EU/mg, or less then about 0.01 EU/mg, or less then about 0.001 EU/mg.

In one embodiment, the invention comprises administering a composition wherein said administration is oral, parenteral, intramuscular, intranasal, vaginal, rectal, lingual, sublingual, buccal, intrabuccal, intravenous, cutaneous, subcutaneous or transdermal.

In another embodiment the invention further comprises administering a composition in combination with other therapies, such as surgery, chemotherapy, hormonal therapy, biological therapy, immunotherapy or radiation therapy.

In another embodiment the invention comprises administering a composition comprising an antibody of the invention in combination with an antagonist of the biological activity of CSF1R, and/or CSF1, simultaneously, serially or separately.

In another embodiment, the invention comprises administering a composition comprising an antibody of the invention in combination with an antagonist of the biological activity of VEGF, and/or VEGFR, simultaneously, serially or separately.

In another embodiment, the invention comprises administering a composition comprising an antibody of the invention in combination with an antagonist of the biological activity of TNF-α, simultaneously, serially or separately.

Dosing/Administration

To prepare pharmaceutical or sterile compositions including an antibody of the invention, the antibody is mixed with a pharmaceutically acceptable carrier or excipient. Formulations of therapeutic and diagnostic agents can be prepared by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Selecting an administration regimen for a therapeutic depends on several factors, including the serum or tissue turnover rate of the entity, the level of symptoms, the immunogenicity of the entity, and the accessibility of the target cells in the biological matrix. In certain embodiments, an administration regimen maximizes the amount of therapeutic delivered to the patient consistent with an acceptable level of side effects. Accordingly, the amount of biologic delivered depends in part on the particular entity and the severity of the condition being treated. Guidance in selecting appropriate doses of antibodies, cytokines, and small molecules are available (see, e.g., Wawrzynczak (1996) Antibody Therapy, Bios Scientific Pub. Ltd, Oxfordshire, UK Kresina (ed.) (1991) Monoclonal Antibodies, Cytokines and Arthritis, Marcel Dekker, New York, N.Y.; Bach (ed.) (1993) Monoclonal Antibodies and Peptide Therapy in Autoimmune Diseases, Marcel Dekker, New York, N.Y.; Baert, et al. (2003) New Engl. J. Med. 348:601-608; Milgrom, et al. (1999) New Engl. J. Med. 341:1966-1973; Slamon. et al. (2001) New Engl. J. Med. 344:783-792; Beniaminovitz, et al. (2000) New Engl. J. Med. 342:613-619; Ghosh, et al. (2003) New Engl. J. Med. 348:24-32; Lipsky, et al. (2000) New Engl. J. Med. 343:1594-1602).

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Compositions comprising antibodies of the invention can be provided by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 µg/kg, at least 0.5 µg/kg, at least 1 µg/kg, at least 10 µg/kg, at least 100 µg/kg, at least 0.2 mg/kg, at least 1.0 mg/kg, at least 2.0 mg/kg, at least 10 mg/kg, at least 25 mg/kg, or at least 50 mg/kg (see, e.g., Yang, et al. (2003) New Engl. J. Med. 349:427-434; Herold, et al. (2002) New Engl. J. Med. 346:1692-1698; Liu, et al. (1999) J. Neurol. Neurosurg. Psych. 67:451-456; Portielji, et al. (20003) Cancer Immunol. Immunother. 52:133-144). The dose may be at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg. The doses administered to a subject may number at least 1, 2, 3, 4, 5, 6, 7, 8, 9, 10, 11, or 12, or more.

For antibodies of the invention, the dosage administered to a patient may be 0.0001 mg/kg to 100 mg/kg of the patient's body weight. The dosage may be between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight.

The dosage of the antibodies of the invention may be calculated using the patient's weight in kilograms (kg) multiplied by the dose to be administered in mg/kg. The dosage of the antibodies of the invention may be 150 µg/kg or less, 125 µg/kg or less, 100 µg/kg or less, 95 µg/kg or less, 90 µg/kg or less, 85 µg/kg or less, 80 µg/kg or less, 75 lµg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less, 5 µg/kg or less, 2.5 µg/kg or less, 2 µg/kg or less, 1.5 µg/kg or less, 1 µg/kg or less, 0.5 µg/kg or less, or 0.5 µg/kg or less of a patient's body weight.

Unit dose of the antibodies of the invention may be 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

The dosage of the antibodies of the invention may achieve a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in a subject. Alternatively, the dosage of the antibodies of the invention may achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml in the subject.

Doses of antibodies of the invention may be repeated and the administrations may be separated by at least 1 day, 2 days, 3 days, 5 days, 10 days, 15 days, 30 days, 45 days, 2 months, 75 days, 3 months, or at least 6 months.

An effective amount for a particular patient may vary depending on factors such as the condition being treated, the overall health of the patient, the method route and dose of administration and the severity of side affects (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

The route of administration may be by, e.g., topical or cutaneous application, injection or infusion by intravenous, intraperitoneal, intracerebral, intramuscular, intraocular, intraarterial, intracerebrospinal, intralesional, or by sustained release systems or an implant (see, e.g., Sidman et al. (1983) Biopolymers 22:547-556; Langer, et al. (1981) J. Biomed. Mater. Res. 15:167-277; Langer (1982) Chem. Tech. 12:98-105; Epstein, et al. (1985) Proc. Natl. Acad. Sci. USA 82:3688-3692; Hwang, et al. (1980) Proc. Natl. Acad. Sci. USA 77:4030-4034; U.S. Pat. Nos. 6,350,466 and 6,316,024).

Where necessary, the composition may also include a solubilizing agent and a local anesthetic such as lidocaine to ease pain at the site of the injection. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, an antibody, combination therapy, or a composition of the invention is administered using Alkermes AIR™ pulmonary drug delivery technology (Alkermes, Inc., Cambridge, Mass.).

A composition of the present invention may also be administered via one or more routes of administration using one or more of a variety of methods known in the art. As will be appreciated by the skilled artisan, the route and/or mode of administration will vary depending upon the desired results. Selected routes of administration for antibodies of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, a composition of the invention can be administered via a non-parenteral route, such as a topical, epidermal or mucosal route of administration, for example, intranasally, orally, vaginally, rectally, sublingually or topically.

If the antibodies of the invention are administered in a controlled release or sustained release system, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J Med. 321:574). Polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. A controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more antibodies of the invention. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

If the antibody of the invention is administered topically, it can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity, in some instances, greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, in some instances, in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the compositions comprising antibodies are administered intranasally, it can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

Methods for co-administration or treatment with a second therapeutic agent, e.g., a cytokine, steroid, chemotherapeutic agent, antibiotic, or radiation, are well known in the art (see, e.g., Hardman, et al. (eds.) (2001) Goodman and Gilman's The Pharmacological Basis of Therapeutics, 10.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%; at least 40%, or at least 50%.

Additional therapies (e.g., prophylactic or therapeutic agents), which can be administered in combination with the antibodies of the invention may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies of the invention. The two or more therapies may be administered within one same patient visit.

The antibodies of the invention and the other therapies may be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain embodiments, the antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); p 120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The invention provides protocols for the administration of pharmaceutical composition comprising antibodies of the invention alone or in combination with other therapies to a subject in need thereof. The therapies (e.g., prophylactic or therapeutic agents) of the combination therapies of the present invention can be administered concomitantly or sequentially to a subject. The therapy (e.g., prophylactic or therapeutic agents) of the combination therapies of the present invention can also be cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time and repeating this sequential administration, i.e., the cycle, in order to reduce the development of resistance to one of the therapies (e.g., agents) to avoid or reduce the side effects of one of the therapies (e.g., agents), and/or to improve, the efficacy of the therapies.

The therapies (e.g., prophylactic or therapeutic agents) of the combination therapies of the invention can be administered to a subject concurrently. The term "concurrently" is not limited to the administration of therapies (e.g., prophylactic or therapeutic agents) at exactly the same time, but rather it is meant that a pharmaceutical composition comprising antibodies of the invention are administered to a subject in a sequence and within a time interval such that the antibodies of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

Another embodiment of the invention includes an assay kit for detecting Angiopoietin-1 and/or Angiopoietin-2 in mammalian tissues, cells, or body fluids to screen for angiogenesis-related diseases. The kit includes an antibody that binds to Angiopoietin-1 and/or Angiopoietin-1 and a means for indicating the reaction of the antibody with Angiopoietin-1 and/or Angiopoietin-2, if present. The antibody may be a monoclonal antibody. In one embodiment, the antibody that binds Angiopoietin-2 is labeled. In another embodiment the antibody is an unlabeled primary antibody and the kit further includes a means for detecting the primary antibody. In one embodiment, the means includes a labeled second antibody that is an anti-immunoglobulin. In some embodiments, the antibody is labeled with a marker selected from the group consisting of a fluorochrome, an enzyme, a radionuclide and a radio-opaque material.

Incorporation by Reference

All references cited herein, including patents, patent applications, papers, text books, and the like, and the references cited therein, to the extent that they are not already, are hereby incorporated herein by reference in their entirety. In addition, the following U.S. provisional patent applications 61/023,958 filed Jan. 28, 2008, 61/100,063 filed Sep. 25, 2008, and 61/142,778 filed Jan. 6, 2009 are hereby incorporated by reference herein in their entireties for all purpose.

Equivalents

The foregoing written specification is considered to be sufficient to enable one skilled in the art to practice the invention. The foregoing description and Examples detail certain embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

Specific Embodiments:

1. An isolated antibody that binds to Ang-2, wherein said antibody comprises a variable light chain, said light chain comprising a sequence selected from the group consisting of SEQ ID No:3 (MEDI1); SEQ ID No:4 (MEDI2); SEQ ID No:5 (MEDI3); SEQ ID No:6 (MEDI4); and SEQ ID No:8 (MEDI6).
2. The antibody of embodiment 1, wherein said antibody is an IgG1 or an IgG2 isotype antibody.
3. The antibody of embodiment 1 or 2, wherein said antibody further comprises a variable heavy chain region comprising SEQ ID No:7 (MEDI5).
4. The antibody of any of embodiments 1-3, wherein said antibody, when produced, exhibits a production efficiency in a mammalian host cell equal to or greater than 2 times the production efficiency of the Ang-2 antibody 3.19.3.
5. The antibody of embodiment 4, wherein said production efficiency is equal to or greater than 3 times the production efficiency of the Ang-2 antibody 3.19.3.
6. The antibody of embodiment 4, wherein said production efficiency is equal to or greater than 5 times the production efficiency of the Ang-2 antibody 3.19.3.
7. A nucleic acid encoding the antibody of any of embodiments 1-6.
8. A vector comprising the nucleic acid of embodiment 7
9. A host cell comprising the vector of embodiment 8.
10. A pharmaceutical composition comprising the antibody of any of embodiments 1-6 and an excipient.
11. A method of preventing, treating, or managing cancer in an animal in need thereof, said method comprising administering to said animal a dose of an effective amount of the composition of embodiment 10.
12. A method of preventing metastasis of cancer in an animal in need thereof, said method comprising administering to said animal a dose of an effective amount of the composition of embodiment 10.
13. A method of preventing recurrences of cancer in an animal in need thereof, said method comprising administering to said animal a dose of an effective amount of the composition of embodiment 10.
14. A method of preventing advancement of cancer in an animal in need thereof, said method comprising administering to said animal a dose of an effective amount of the composition of embodiment 10.
15. A method of preventing development of cancer from a pre-cancerous state in an animal in need thereof, said method comprising administering to said animal an effective amount of the composition of embodiment 10.
16. A method of preventing symptoms of cancer in an animal in need thereof, said method comprising administering to said animal a dose of an effective amount of the composition of embodiment 10.
17. A method of promoting tumor regression of a cancer in an animal in need thereof, said method comprising administering to said animal a dose of an effective amount of the composition of embodiment 10.
18. A method of inhibiting tumor cell proliferation in an animal in need thereof, said method comprising administering to said animal a dose of an effective amount of the composition of embodiment 10.
19. A method of depleting malignant tumor cells in an animal in need thereof, said method comprising administering to said animal a dose of an effective amount of the composition of embodiment 10.
20. A method of inhibiting angiogenesis of a cancer tumor in an animal in need thereof, said method comprising administering to said animal a dose of an effective amount of the composition of embodiment 10.
21. The method of any of embodiments 11-20, wherein said method comprises an additional dosing to said animal of one or more other cancer therapies.
22. The method of embodiment 21, wherein said one or more other cancer therapies are chemotherapies, biological therapies/immunotherapies, radiation therapies, hormonal therapies, or surgery.

23. The method of any of embodiments 11-22, wherein said method further comprises the administration of another therapeutic agent that is not a cancer therapeutic agent.
24. The method of embodiment 23, wherein said therapeutic agent is an anti-emetic agent, anti-fungal agent, anti-parasitic agent, anti-inflammatory agent, immunomodulatory agent, anti-viral agent, or antibiotic.
25. The method of any of embodiments 21-24, wherein said chemotherapy is selected from the group consisting of 5-Flurouracil, carboplatin, and paclitaxel.
26. The method of any of embodiments 21-25, wherein said immunotherapy is the administration of bevacizumab or an antibody that competes for the same epitope as bevacizumab.
27. The method of any of embodiments 11-26, wherein said cancer or tumor is selected from the group consisting of melanoma, colon, colorectal, lung, small cell lung carcinoma, non-small cell lung carcinoma, breast, rectum, stomach, glioma, prostate, ovary, testes, thyroid, blood, kidney, liver, hepatocellular carcinoma pancreas, brain, neck, glioblastoma, endometrial cancer, and central nervous system cancer.
28. The method of any of embodiments 11-27, wherein said animal has been previously treated by administration of one or more cancer therapies but not by administration of the composition of embodiment 10.
29. The method of any embodiments 11-27, wherein said animal has been previously treated with chemotherapy alone, or in combination with one or more radiation therapies, biological/immunotherapies, hormonal therapies or surgery.
30. The method of any of embodiments 11-27, wherein said animal has been previously treated with radiation therapy alone, or in combination with one or more chemotherapies, biological therapies/immunotherapies, hormonal therapies or surgery.
31. The method of any of embodiments 11-27, wherein said animal has been previously treated with biological therapies/immunotherapies alone, or in combination with one or more chemotherapies, radiation therapy, hormonal therapies or surgery.
32. The method of any of embodiments 11-27, wherein said animal has been previously treated with hormonal therapies alone, or in combination with one or more chemotherapies, radiation therapy, biological therapies/immunotherapies or surgery.
33. The method of any of embodiments 11-27, wherein said animal has been previously treated with surgery alone, or in combination with one or more chemotherapies, radiation therapy, hormonal therapies or biological therapies/immunotherapies.
34. The method of any of embodiments 11-33, wherein said cancer is refractory to chemotherapy or radiation therapy.
35. The method of any of embodiments 11-34, wherein said administration is intravenously, subcutaneously, intratumorally, intramuscularly, parenterally, or orally.
36. The method of any of embodiments 21-35, wherein said composition and cancer therapy are administered by the same mode of administration.
37. The method of any of embodiments 21-35, wherein said composition and cancer therapy are administered by a different mode of administration.
38. The method of any of embodiments 21-35, wherein said composition and cancer therapy are administered in the same dosage form.
39. The method of any of embodiments 21-35, wherein said composition and cancer therapy are administered in different dosage forms.
40. The method of any of embodiments 21-39, wherein said cancer therapy is selected from the group consisting of radiation therapies, biological therapies/immunotherapies, hormonal therapies and surgery.
41. A method of preventing, treating, or managing disease-related angiogenesis in an animal in need thereof, said method comprising administering to said animal a dose of an effective amount of the composition of embodiment 10.
42. The method of embodiment 41, wherein the disease-related angiogenesis is associated with seronegative arthritis, seropositive arthritis, arthritis related to other arthropathies, osteoarthritis or SLE.
43. The method of embodiment 42, wherein the seropositive arthritis is rheumatoid arthritis.
44. A method of preventing recurrences of disease-related angiogenesis in an animal in need thereof, said method comprising administering to said animal a dose of an effective amount of the composition of embodiment 10.
45. A method of preventing advancement of disease-related angiogenesis in an animal in need thereof, said method comprising administering to said animal a dose of an effective amount of the composition of embodiment 10.
46. A method of treating rheumatoid arthritis in an animal in need thereof, said method comprising administering to said animal an effective amount of the composition of embodiment 10.
47. A method of preventing symptoms of disease-related angiogenesis in an animal in need thereof, said method comprising administering to said animal a dose of an effective amount of the composition of embodiment 10.
48. The method of any of embodiments 41-47, wherein said method comprises an additional dosing to said animal of one or more other anti-inflammatory therapies.
49. The method of embodiment 48, wherein said one or more other anti-inflammatory therapies are chemotherapies, biological therapies/immunotherapies, radiation therapies, hormonal therapies, or surgery.
50. The method of embodiment 49, wherein said biological therapy/immunotherapy is a TNF-α antagonist,
51. The method of embodiment 50, wherein said TNF-α is selected from etanercept (ENBREL®), adalimumab (HUMIRA®), and infliximab (REMICADE®).
52. The method of any of embodiments 41-51, wherein said method further comprises the administration of another therapeutic agent that is not an anti-inflammatory therapeutic agent.
53. The method of embodiment 52, wherein said therapeutic agent is an anti-emetic agent, anti-fungal agent, anti-parasitic agent, anti-cancer agent, immunomodulatory agent, anti-viral agent, or antibiotic.
54. The method of any of embodiments 41-53, wherein said animal has been previously treated by administration of one or more anti-inflammatory therapies but not by administration of the composition of embodiment 10.
55. The method of any of embodiments 41-53, wherein said animal has been previously treated with chemotherapy alone, or in combination with one or more radiation therapies, biological/immunotherapies, hormonal therapies or surgery.

56. The method of any of embodiments 41-53, wherein said animal has been previously treated with radiation therapy alone, or in combination with one or more chemotherapies, biological therapies/immunotherapies, hormonal therapies or surgery.

57. The method of any of embodiments 41-53, wherein said animal has been previously treated with biological therapies/immunotherapies alone, or in combination with one or more chemotherapies, radiation therapy, hormonal therapies or surgery.

58. The method of any of embodiments 41-53, wherein said animal has been previously treated with hormonal therapies alone, or in combination with one or more chemotherapies, radiation therapy, biological therapies/immunotherapies or surgery.

59. The method of any of embodiments 41-53, wherein said animal has been previously treated with surgery alone, or in combination with one or more chemotherapies, radiation therapy, hormonal therapies or biological therapies/immunotherapies.

60. A method of reducing endothelial cell proliferation in an animal, said method comprising administration of a dose of an effective amount of the composition of embodiment 10.

61. A method of inhibiting Ang-2 and/or Ang-1 binding to Tie-2 in an animal, said method comprising administration of a dose of an effective amount of the composition of embodiment 10.

62. A method of inhibiting Tie-2 phosphorylation in an animal, said method comprising administration of a dose of an effective amount of the composition of embodiment 10.

63. A method of reducing levels of circulating Ang-2 and/or Ang-1 polypeptide in an animal, said method comprising administration of a dose of an effective amount of the composition of embodiment 10.

64. A pharmaceutical composition comprising a combination of i) an antagonist of the biological activity of Angiopoietin-2 and/or Tie-2, and ii) an antagonist of the biological activity of CSF1R, and/or CSF1.

65. The composition according to embodiment 64, wherein the antagonist of Angiopoietin-2 is an antibody.

66. The composition according to embodiment 65, wherein the antagonist of Angiopoietin-2 is a fully human monoclonal antibody.

67. The composition according to embodiments 65 or 66, wherein the antibody binds to the same epitope as any one of fully human monoclonal antibodies selected from the group consisting of 3.31.2, 5.16.3, 5.86.1, 5.88.3, 3.3.2, 5.103.1, 5.101.1, 3.19.3, 5.28.1, 5.78.3, MEDI1/5, MEDI2/5, MEDI3/5, MEDI6/5, and MEDI4/5.

68. The composition according to embodiment 65, wherein the antibody is a fully human monoclonal antibody selected from the group consisting of: 33.31.2, 5.16.3, 5.86.1, 5.88.3, 3.3.2, 5.103.1, 5.101.1, 3.19.3, 5.28.1, 5.78.3, MEDI1/5, MEDI2/5, MEDI3/5, MEDI6/5, and MEDI4/5.

69. The composition according to any of embodiments 64-68, wherein the antagonist of the biological activity of CSF1R is a tyrosine kinase inhibitor.

70. The composition according to embodiment 69, wherein the antagonist of the biological activity of CSF1R is selected from any one of:

2-chloro-N-pyridin-3-yl-5-{[3-(trifluoromethyl)benzoyl]amino}benzamide;

2-chloro-N-(5-fluoropyridin-3-yl)-5-{[3-(trifluoromethyl)benzoyl]amino}benzamide;

2-chloro-N-(5-fluoropyridin-3-yl)-5-{[3-fluoro-5-(trifluoromethyl)benzoyl]amino}-benzamide;

2-methyl-N-pyridin-3-yl-5-{[3-(trifluoromethyl)benzoyl]amino}benzamide;

5-{[3-fluoro-5-(trifluoromethyl)benzoyl]amino}-2-methyl-N-pyridin-3-ylbenzamide;

2-chloro-5-[(3-cyclopropylbenzoyl)amino]-N-pyridin-3-ylbenzamide;

2-chloro-5-[(3-chlorobenzoyl)amino]-N-pyridin-3-ylbenzamide;

5-[(3-chloro-5-fluorobenzoyl)amino]-2-methyl-N-pyridin-3-ylbenzamide;

5-[(3-cyclopropyl-5-fluorobenzoyl)amino]-2-methyl-N-pyridin-3-ylbenzamide;

5-[(3-chlorobenzoyl)amino]-2-methyl-N-pyridin-3-ylbenzamide;

5-{[3-(1-cyano-1-methylethyl)benzoyl]amino}-2-methyl-N-(2-methyl-1,3-thiazol-5-yl)benzamide;

2-chloro-N-1,3-thiazol-5-yl-5-{[3-(trifluoromethyl)benzoyl]amino}benzamide;

2-chloro-5-[(3-chlorobenzoyl)amino]-N-1,3-thiazol-5-ylbenzamide;

2-chloro-5-[(3,5-dimethylbenzoyl)amino]-N-1,3-thiazol-5-ylbenzamide;

5-({[3-(1-cyano-1-methylethyl)benzoyl]amino}-2-methyl-N-1,3-thiazol-5-ylbenzamide;

2-methyl-N-(2-methyl-1,3-thiazol-5-yl)-5-{[3-(trifluoromethyl)benzoyl]amino}benzamide;

2-chloro-5-[(3-chlorobenzoyl)amino]-N-(2-methyl-1,3-thiazol-5-yl)benzamide;

2-chloro-5-[(3,5-dimethylbenzoyl)amino]-N-(2-methyl-1,3-thiazol-5-yl)benzamide;

2-chloro-N-(2-methyl-1,3-thiazol-5-yl)-5-{[3-(trifluoromethyl)benzoyl]amino}benzamide;

2-chloro-5-{[3-fluoro-5-(trifluoromethyl)benzoyl]amino}-N-(2-methyl-1,3-thiazol-5-yl)benzamide;

5-[(5-{[3-(1-cyano-1-methylethyl)benzoyl]amino}-2-methylbenzoyl)amino]-N-methyl-1,3-thiazole-2-carboxamide;

5-{[3-fluoro-5-(trifluoromethyl)benzoyl]amino}-2-methyl-N-(2-methyl-1,3-thiazol-5-yl)benzamide;

5-[(3-chloro-5-fluorobenzoyl)amino]-2-methyl-N-(2-methyl-1,3-thiazol-5-yl)benzamide;

5-[(3-cyclopropyl-5-fluorobenzoyl)amino]-2-methyl-N-(2-methyl-1,3-thiazol-5-yl)benzamide;

5-[(3-chlorobenzoyl)amino]-2-methyl-N-(2-methyl-1,3-thiazol-5-yl)benzamide;

5-[3,4-dichlorobenzoyl)amino]-2-methyl-N-(2-methyl-1,3-thiazol-5-yl)benzamide;

5-[(3-cyclopropylbenzoyl)amino]-2-methyl-N-(2-methyl-1,3-thiazol-5-yl)benzamide;

5-[(3,5-dimethylbenzoyl)amino]-2-methyl-N-(2-methyl-1,3-thiazol-5-yl)benzamide;

2-methyl-5-[(3-methylbenzoyl)amino]-N-(2-methyl-1,3-thiazol-5-yl)benzamide;

2,6-dichloro-N-(4-methyl-3-{[(2-methyl-1,3-thiazol-5-yl)amino]carbonyl}phenyl)isonicotinamide;

2-methyl-5-{[(3-methylcyclohexyl)carbonyl]amino}-N-(2-methyl-1,3-thiazol-5-yl)benzamide;

2-methyl-N-(2-methyl-1,3-thiazol-5-yl)-5-(pentanoylamino)benzamide;

2-methyl-5-[(4-methylhexanoyl)amino]-N-(2-methyl-1,3-thiazol-5-yl)benzamide;

4-[(2,4-difluorophenyl)amino]-7-ethoxy-6-(4-methylpiperazin-1-yl)quinoline-3-carboxamide;

4-[(2,3-dichlorophenyl)amino]-7-ethoxy-6-(4-methylpiperazin-1-yl)quinoline-3-carboxamide;
7-ethoxy-4-[(2-fluoro-5-methylphenyl)amino]-6-(4-isopropylpiperazin-1-yl)quinoline-3-carboxamide;
4-[(3-chloro-2-fluorophenyl)amino]-7-ethoxy-6-(4-methylpiperazin-1-yl)quinoline-3-carboxamide;
7-ethoxy-4-[(2-fluoro-5-methylphenyl)amino]-6-(4-methylpiperazin-1-yl)quinoline-3-carboxamide;
7-ethoxy-4-[(2-fluoro-4-methylphenyl)amino]-6-(4-methylpiperazin-1-yl)quinoline-3-carboxamide;
4-[(2,4-difluorophenyl)amino]-7-(2-methoxyethoxy)-6-(4-methylpiperazin-1-yl)quinoline-3-carboxamide;
4-[(2-fluoro-4-methylphenyl)amino]-7-(2-methoxyethoxy)-6-(4-methylpiperazin-1-yl)quinoline-3-carboxamide;
4-[(2-fluoro-5-methylphenyl)amino]-7-(2-methoxyethoxy)-6-(4-methylpiperazin-1-yl)quinoline-3-carboxamide;
4-[(2-fluoro-4-methylphenyl)amino]-6-(4-isopropylpiperazin-1-yl)-7-(2-methoxyethoxy)quinoline-3-carboxamide;
7-ethoxy-4-[(2-fluoro-4-methylphenyl)amino]-6-(1-methylpiperidin-4-yl)quinoline-3-carboxamide;
4-[(2,4-difluorophenyl)amino]-7-ethoxy-6-(1-methylpiperidin-4-yl)quinoline-3-carboxamide;
4-[(2,4-difluorophenyl)amino]-7-ethoxy-6-(1-isopropylpiperidin-4-yl)quinoline-3-carboxamide;
7-ethoxy-4-[(2-fluoro-4-methylphenyl)amino]-6-(1-isopropylpiperidin-4-yl)quinoline-3-carboxamide;
4-[(2-fluoro-4-methylphenyl)amino]-7-methoxy-6-(1-methylpiperidin-4-yl)quinoline-3-carboxamide;
4-[(3-chloro-2-fluorophenyl)amino]-7-methoxy-6-(1-methylpiperidin-4-yl)quinoline-3-carboxamide;
4-[(2,4-difluorophenyl)amino]-7-methoxy-6-(1-methylpiperidin-4-yl)quinoline-3-carboxamide;
4-[(2-fluoro-4-methylphenyl)amino]-6-(1-isopropylpiperidin-4-yl)-7-methoxyquinoline-3-carboxamide;
4-[(2,4-difluorophenyl)amino]-6-(1-isopropylpiperidin-4-yl)-7-methoxyquinoline-3-carboxamide; and
4-[(3-chloro-2-fluorophenyl)amino]-6-(1-isopropylpiperidin-4-yl)-7-methoxyquinoline-3-carboxamide;
7-Ethoxy-4-[(2-fluoro-4-methyl-phenyl)amino]-6-(4-methylpiperazin-1-yl)cinnoline-3-carboxamide;
4-(2-Fluoro-4-methylphenylamino)-7-methoxy-6-(4-methylpiperazin-1-yl)cinnoline-3-carboxamide;
4-[(2,4-Difluorophenyl)amino]-7-methoxy-6-(4-methylpiperazin-1-yl)cinnoline-3-carboxamide;
6-[(3R,5S)-3,5-Dimethylpiperazin-1-yl]-4-[(2-fluoro-4-methylphenyl)amino]-7-methoxycinnoline-3-carboxamide;
4-[(2-Fluoro-4-methylphenyl)amino]-6-[4-(2-hydroxyethyl)piperazin-1-yl]-7-methoxycinnoline-3-carboxamide;
7-Ethoxy-4-[(2-fluoro-4-methylphenyl)amino]-6-[4-(2-hydroxyethyl)piperazin-1-yl]cinnoline-3-carboxamide;
4-[(3-Chloro-2-fluorophenyl)amino]-6-[(3R,5S)-3,5-dimethylpiperazin-1-yl]-7-methoxycinnoline-3-carboxamide;
4-[(2-Fluoro-4-methylphenyl)amino]-6-(1-isopropylpiperidin-4-yl)-7-methoxycinnoline-3-carboxamide hydrochloride;
4-[(2-Fluoro-4-methylphenyl)amino]-6-[1-(2-hydroxyethyl)piperidin-4-yl]-7-methoxycinnoline-3-carboxamide; and
4-[(2-Fluoro-4-methylphenyl)amino]-6-{4-[(2R)-2-hydroxypropanoyl]piperazin-1-yl}-7-methoxycinnoline-3-carboxamide;
or a pharmaceutically acceptable salt thereof.

71. A pharmaceutical composition comprising a combination according to any one of embodiments 62 to 70, in association with a pharmaceutically-acceptable excipient or carrier.

72. A pharmaceutical composition according to embodiment 71, for use in the treatment of disease-related angiogenesis or inflammation.

73. A pharmaceutical composition according to embodiment 71, for use in the treatment of cancer.

74. A method of treating disease-related angiogenesis or inflammation in an animal in need thereof with a combination according to any one of embodiments 62-73.

75. A method of treating cancer in an animal in need thereof with a combination according to any one of embodiments 62-73.

76. A composition comprising an antagonist of the biological activity of Angiopoietin-2, and/or Tie-2; and a chemotherapeutic agent.

77. The composition according to embodiment 76, wherein the antagonist of Angiopoietin-2 is an antibody.

78. The composition according to embodiment 77, wherein the antagonist of Angiopoietin-2 is a fully human monoclonal antibody.

79. The composition according to any one of embodiments 77 or 78, wherein the antibody binds to the same epitope as an antibody selected from the group consisting of 3.31.2, 5.16.3, 5.86.1, 5.88.3, 3.3.2, 5.103.1, 5.101.1, 3.19.3, 5.28.1, 5.78.3, MEDI1/5, MEDI2/5, MEDI3/5, MEDI6/5, and MEDI4/5.

80. The composition according to embodiment 78, wherein the antibody is a fully human monoclonal antibody selected from the group consisting of 3.31.2, 5.16.3, 5.86.1, 5.88.3, 3.3.2, 5.103.1, 5.101.1, 3.19.3, 5.28.1, 5.78.3, MEDI1/5, MEDI2/5, MEDI3/5, MEDI6/5, and MEDI4/5.

81. The composition according to any of embodiments 76-80, wherein the chemotherapeutic agent is selected from the group consisting of docetaxel, AZD4877, vincristine, vinblastine, vindesine and vinorelbine, taxol, taxotere, 5-fluorouracil, gemcitabine, fluoropyrimidines tegafur, raltitrexed, capecitabine, methotrexate, pemetrexed, cytosine arabinoside, hydroxyurea; irinotecan, etoposide topotecan, camptothecin teniposide, amsacrine, oxaliplatin, cisplatin oxaliplatin, 5-fluorouracil, irinotecan, gemcitabine and carboplatin.

82. The composition according to any of embodiments 76 to 81 in association with a pharmaceutically acceptable excipient or carrier.

83. A method of antagonizing the biological activity of Angiopoietin-2, and/or Tie-2 comprising administering the composition according to any of embodiments 76 to 82.

84. A method of producing an anti-cancer effect in a patient comprising administering a therapeutically effective amount of a composition of any one of embodiments 76 to 82.

85. A method of reducing tumor growth in an animal comprising administering a therapeutically effective amount of a composition of any one of embodiments 76 to 82.

SEQUENCES 3.19.3 light chain
SEQ ID No.: 1
EIVLTQSPGTLSLSPGERATLSCRASQSITGSYLAWYQQKPGQAPRLLIC

GASSWATGIPDRFSGSGSGTDFTLTISRLEPEDFAVYYCQQYSSSPITFG

-continued
```
QGTRLEIKRTVAAPSVFIFPPSDEQLKSGTASVVCLLNNFYPREAKVQWK

WDNALQSGNSQESVTEQDSKDSTYSLSSTLTLSKADYEKHKVYACEVTHQ

GLSSPVTKSFNRGEC
```

The boxed residue in this sequence represents an unpaired cysteine (C49) that may be changed to any other amino acid. Examples of such changes are highlighted in the light chain sequences below.

3.19.3 heavy chain
SEQ ID No: 2
```
QVQLVESGGGVVQPGRSLRLSCAASGFTFTNYGMHW[C]RQAPGKGLEWVAV

ISHDGNNKYYVDSVKGRFTISRDNSKNTLYLQMNSLRAEDTAVYYCAREG

IDFWSGLNWFDPWGQGTLVTVSS
```

The boxed residue in this sequence represents an example of a residue that may be "backmutated" to another residue. One example of such a "backmutation" is represented in the MEDI5 heavy chain sequence.

MED11 light chain
SEQ ID No: 3
```
EIVLTQSPGTLSLSPGERATLSCRASQSITGSYLAWYQQKPGQAPRLLI[T]

GASSWATGIPDRFSGSGSGTDFTLTISRLEPEDFAVYYCQQYSSSPITFG

QGTRLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

MED12 light chain
SEQ ID No: 4
```
EIVLTQSPGTLSLSPGERATLSCRASQSITGSYLAWYQQKPGQAPRLLI[N]

GASSWATGIPDRFSGSGSGTDFTLTISRLEPEDFAVYYCQQYSSSPITFG

QGTRLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

MED13 light chain
SEQ ID No: 5
```
EIVLTQSPGTLSLSPGERATLSCRASQSITGSYLAWYQQKPGQAPRLLI[D]

GASSWATGIPDRFSGSGSGTDFTLTISRLEPEDFAVYYCQQYSSSPITFG

QGTRLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

MED14 light chain
SEQ ID No: 6
```
EIVLTQSPGTLSLSPGERATLSCRASQSITGSYLAWYQQKPGQAPRLLI[A]

GASSWATGIPDRFSGSGSGTDFTLTISRLEPEDFAVYYCQQYSSSPITFG

QGTRLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

MED15 heavy chain
SEQ ID No: 7
```
QVQLVESGGGVVQPGRSLRLSCAASGFTFTNYGMHW[V]RQAPGKGLEWVAV

ISHDGNNKYYVDSVKGRFTISRDNSKNTLYLQMNSLRAEDTAVYYCAREG

IDFWSGLNWFDPWGQGTLVTVSS
```

MED16 light chain
SEQ ID No: 8
```
EIVLTQSPGTLSLSPGERATLSCRASQSITGSYLAWYQQKPGQAPRLLI[T]

GASSWATGI[A]DRFSGSGSGTDFTLTISRLEPEDFAVYYCQQYSSSPITFG

QGTRLEIKRTVAAPSVFIFPPSDEQLKSGTASVVCLLNNFYPREAKVQWK

VDNALQSGNSQESVTEQDSKDSTYSLSSTLTLSKADYEKHKVYACEVTHQ

GLSSPVTKSFNRGEC
```

EXAMPLES

Example 1: Potency of Modified Ang-2 Antibodies

In this example, Ang-2 specific antibodies comprising the light and heavy chains of the Ang-2 antibody 3.19.3 have been modified such that amino acid substitutions for cysteine at position 49 of the light chain were introduced. The potency of the resultant antibodies was measured in an Ang-2:Tie-2 potency assay. The results are presented in Table 1 below.

TABLE 1

| Potency of modified Ang-2 antibodies | |
|---|---|
| Antibody | IC50 |
| 3.19.3 (WT) | 0.06 |
| C49A (MEDI4) SEQ ID No.: 6 | 0.03 |
| C49D (MEDI3) SEQ ID No.: 5 | 0.07 |
| C49E | 0.06 |
| C49F | 0.06 |
| C49G | 0.09 |
| C49H | 0.98 |
| C49I | 0.04 |
| C49K | 103.40 |
| C49L | 0.05 |
| C49M | 0.05 |
| C49N (MEDI2) SEQ ID No.: 4 | 0.04 |
| C49P | 0.07 |
| C49Q | 0.12 |
| C49R | 5.48 |
| C49S | 0.14 |
| C49T (MEDI1) SEQ ID No.: 3 | 0.04 |
| C49V | 0.08 |
| C49W | 1.02 |
| C49Y | 0.73 |
| Control Ab | 0.05 |

Results:

In an Ang-2:Tie-2 potency assay, various modifications of position 49 resulted in antibodies with similar potency. Exemplary antibodies include but are not limited to C49A, C49T, C49N, and C49D. Some of the modifications that included bulky, hydrophobic substitutions, such as C49W resulted in lowered potency demonstrated by an increased IC50 value. Other modifications, including various charged residues such as C49K and C49H also resulted in lowered potency demonstrated by an increased IC50 value.

Example 2: Improved Antibody Production Efficiency

In this example, Ang-2 specific antibodies comprising the light and heavy chains of the Ang-2 antibody 3.19.3 have been modified such that amino acid substitutions for cysteine at position 49 of the light chain were introduced. The relative expression of the resulting antibodies was measured. In addition, position 37 of the heavy chain of several antibodies was also modified to introduce a Val residue (MEDI5).

Materials and Methods: Vectors encoding the heavy and light chains of 3.19.3 (SEQ ID Nos. 2 and 1, respectively), as well as, heavy and light chains set forth as SEQ ID Nos. 7 and 3, respectively (in both an IgG1 and IgG2 format) were expressed in 293F cells with the following protocol: Viable cells (>95%) were diluted in Freestyle293® media (Invitrogen) at a cell density of $1.0 \times 10^6$ cells/min. The various DNA preparations were diluted in 293Fectin® (Invitrogen) and added to cells as per the manufacturers directions. On Day 6 of the transformation, the expressed antibodies were harvested by collecting the culture supernatant. Antibody levels were measured by Protein A binding prior to purification.

Results: The production efficiencies of the "MEDI1/5 IgG1" (having the heavy and light chains set forth as SEQ ID Nos. 7 and 3 in an IgG format), and "MEDI1/5 IgG2" (having the heavy and light chains set forth as SEQ ID Nos. 7 and 3 in an IgG format) antibodies were increased as compared to the production efficiency of the 3.19.3 antibody. The results are summarized in Table 2.

TABLE 2

Improved production efficiency of Ang-2 antibodies

| Antibody | 3.19.3 | MEDI1/5 IgG1 | MEDI1/5 IgG2 |
|---|---|---|---|
| Yield | 10 mg/L | 140 mg/L | 260 mg/L |
| Recovery | 0.2 g | 1.4 g | 2.7 g |

These results demonstrate that the substitution at position 49 of cysteine for threonine in the variable light chain coupled with the substitution at position 37 of glycine to valine in the light chain of an Ang-2 specific antibody leads to greatly improved production efficiencies (i.e. yield and/or recovery).

Example 3. Increased Stability of Ang-2 Antibodies

In an attempt to assess the increased stability of the cysteine substituted Ang-2 antibodies, a stability study was performed. The WT 3.19.3 antibody, as well as, MEDI1/5 in an IgG1 and IgG2 format were concentrated to 10 mg/ml in 10 mM histidine pH 6.0. Samples of the aforementioned formulations were incubated at either 25° C. or 40° C. for two weeks. As a measure of stability, the rate of aggregation (% aggregation/mth) was calculated after the two week time point. The results are presented in Table 3.

TABLE 3

Stability of Ang-2 antibodies

| Sample | % Agg/mth @ 40° C. | % Agg/mth @ 25° C. |
|---|---|---|
| WT (3.19.3) | 42.6 | 2.97 |
| MEDI1/5 IgG1 | 0.21 | 0.21 |
| MEDI1/5 IgG2 | 0.82 | 0.61 |

Figure 2A:
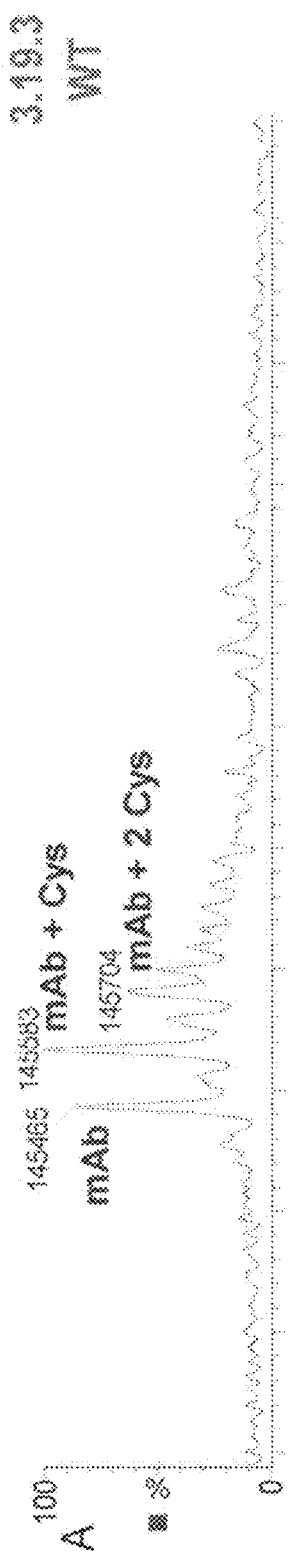
FIG. 2A-C represents a chromatograph of various preparations of Ang-2 antibodies. In (A) the 3.19.3 antibody demonstrates a heterogeneity of sizes corresponding to various adducts formed with the antibody. (B) and (C) represent the Ang-2 specific antibody MEDI1/5 in the IgG1 (B) and IgG2 (C) formats. These antibodies do not exhibit the heterogeneity in sizes displayed by the wild type 3.19.3 antibody.
Figure 2B:
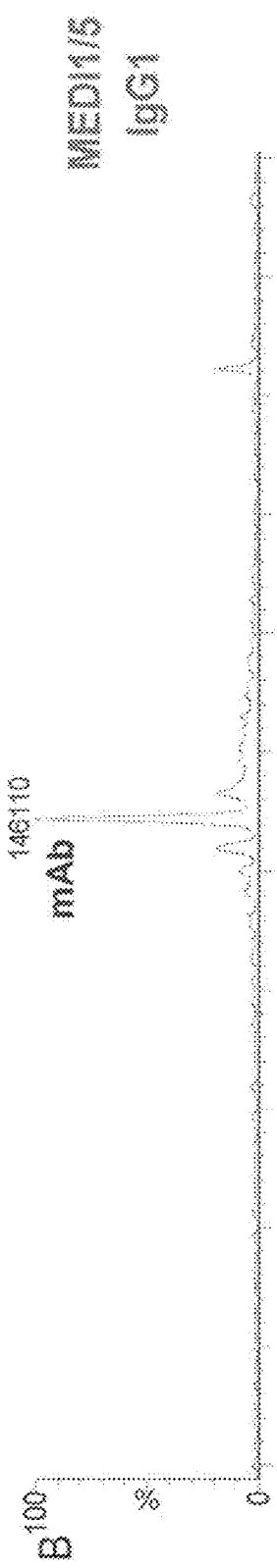
Figure 2C:
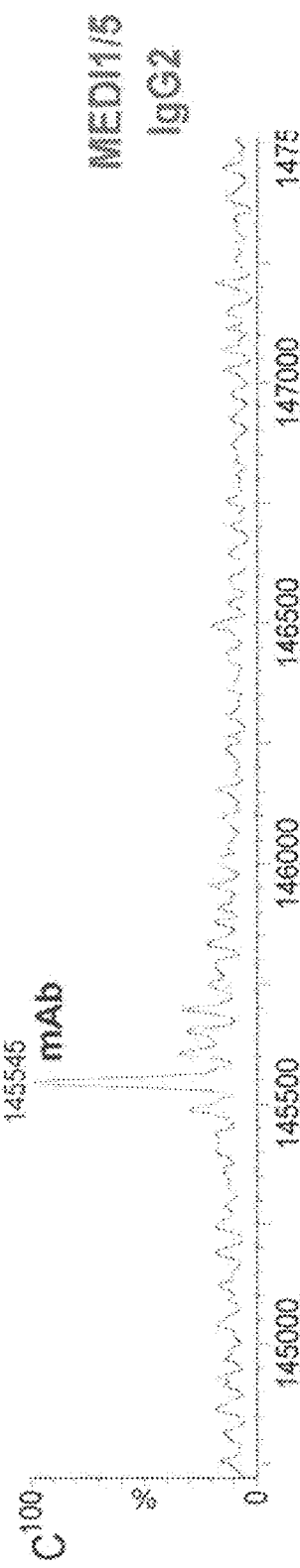

As demonstrated in Table 2, the MEDI1/IgG1 and IgG2 antibodies exhibit an enhanced stability as compared to the WT (3.19.3) antibody. Also, as demonstrated in FIG. 2, much of the heterogeneity demonstrated by the wild type antibody (3.19.3) was abolished in the MEDI1/5 antibodies in an IgG1 or IgG2 formats. The chromatograph in FIG. 2 demonstrates that replacement of C49 in the wild type antibody reduces or eliminates the multiple antibody species present in samples.

Example 4. Increased Stability of Ang-2 Antibodies

Figure 1:
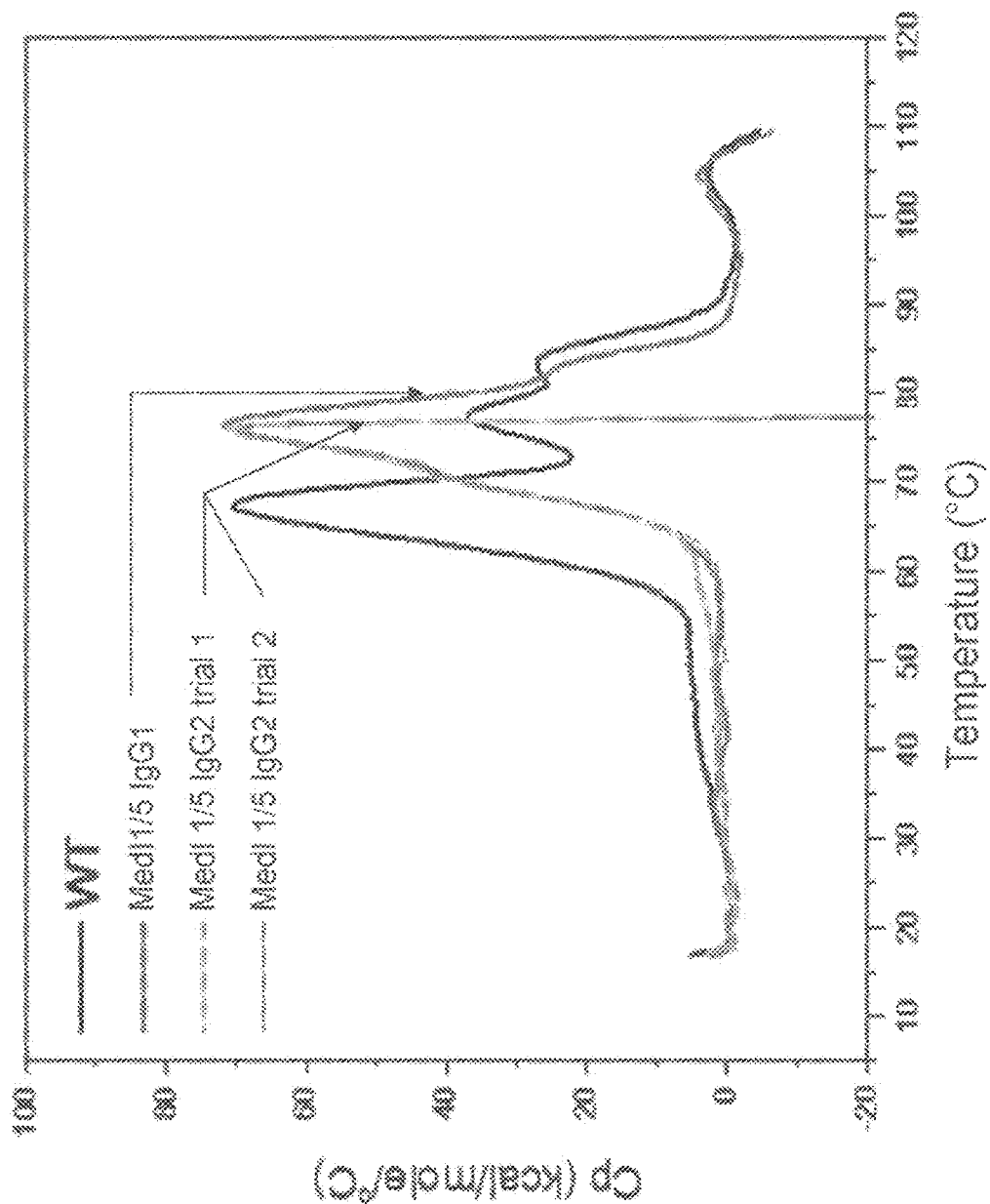
FIG. 1 represents the results from a Differential Scanning Calorimetry experiment of the wild type antibody 3.19.3 (WT) as well as antibodies comprising a VL corresponding to MEDI1 and a VH corresponding to MEDI5 in both an IgG1 and an IgG2 format. The figure depicts the relative increase of melting temperature of the two MEDI1/5 antibodies of the to WT control antibody.

In an attempt to assess the increased stability of the cysteine substituted Ang-2 antibodies, a Differential Scanning Calorimetry (DSC) analysis of WT (3.19.3) and MEDI1/5 IgG1 and IgG2 antibodies was performed. In this example, formulations of WT, MEDI1/5 IgG1, and MEDI1/5 IgG2 antibodies were prepared at 1 g/L antibody in 10 mM histidine, pH 6.0 and subjected to DSC analysis. The results are presented in FIG. 1. As presented, the WT antibody exhibits a melting temperature of about 61° C. The MEDI1/5 IgG1 antibody exhibits a higher melting temperature of about 76° C. The MEDI1/5 IgG2 also exhibits a higher melting temperature of about 76° C., however it subsequently falls out of solution, which was observed in two independent trials (trial 1 and 2).

These results suggest that MEDI1/5 antibodies exhibit increased stability over the WT (3.19.3) antibody as measured by melting temperature.

Example 5: Binding Profiles of Ang-2 Antibodies

In this example the Ang-2 antibody, 3.19.3, and a modified 3.19.3 antibody comprising a C49T (MEDI1/5) substitution were analyzed for Ang-2 binding in a competitive ELISA format assay.

Materials and Methods:

Competitive Tie-2 Fc/Ang2 ELISA: Maxisorp ELISA plates (Nunc, Rochester, N.Y.) were coated with 100 µl of 4 µg/ml Tie-2 Fc (R & D Systems, Minneapolis, Minn.) in 0.1M carbonate buffer pH 9.4 (Pierce, Rockford, Ill.) and incubated overnight at 4° C. The following day, plates were blocked for 1 hour at room temperature with 200 µl of phosphate buffered saline (PBS) (Invitrogen, Carlsbad, Calif.) containing 0.5% bovine serum albumin (BSA) (Sigma, St. Louis, Mo.) and 0.1% Tween-20 (Sigma, St. Louis, Mo.). Plates were washed 3 times with wash buffer (PBS containing 0.05% Tween-20). 50 µl of 11-point serial tertiary dilutions (30 µg/ml high concentration) of 3.19.3 or modified anti-Ang2 antibody were plated, with PBS as a negative control. For antibody capture, 50 µl of 200 ng/ml Biotin Ang2 (R & D Systems, Minneapolis, Minn.) were added and plates were incubated for 2 hours at room temperature. Plates were washed 3 times with wash buffer. Following the wash, 100 ul of 1:5000 streptavidin HRP (Pierce, Rockford, Ill.) dilution in wash buffer were added and incubated for 1 hour at room temperature. Plates were washed 3 times with wash buffer. Plates were developed by adding 100 µl of TMB peroxidase substrate (KPL, Gaithersburg, Md.) for 5 minutes. The reaction was stopped by adding 100 µl/well of 1M phosphoric acid. Optical densities were measured at 450 nm with a microplate reader (Molecular Devices, Sunnyvale, Calif.).

Results: As presented in FIG. 3, the ELISA results demonstrate that the MEDI1/5 antibody in either an IgG1 or an IgG2 format exhibit a very similar binding profile for Ang-2 as compared to the 3.19.3 antibody as measured by competition for Tie-2 in an ELISA format.

Example 6. Combination Studies

The in vivo efficacy of 3.19.3 in combination with small molecule CSF1R tyrosine kinase inhibitors has been evaluated.

Figure 4A:
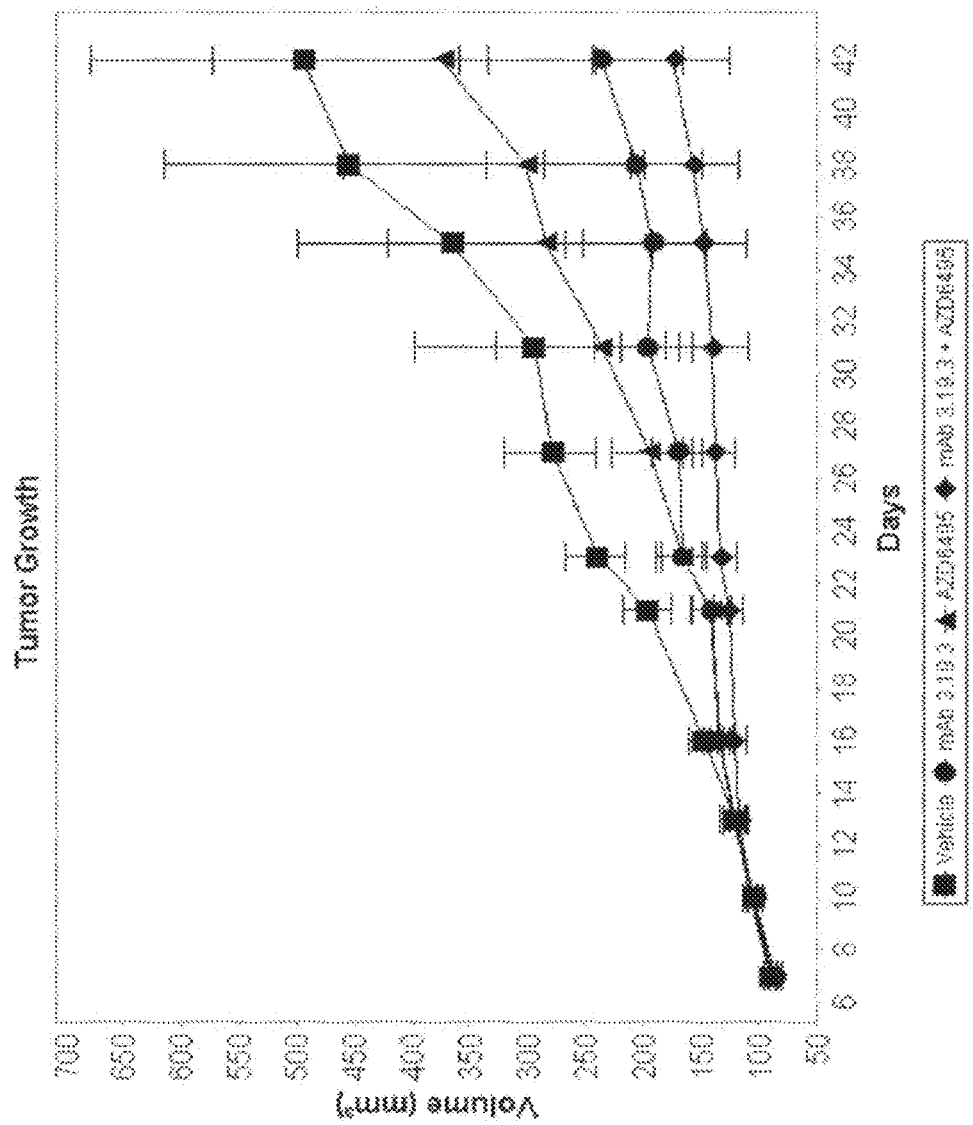
FIG. 4A demonstrates combination efficacy following treatment with mAb 3.19.3 and AZD6495 in mice bearing MCF7 xenograft tumors. The y axis shows the Tumor volume in $mm^3$, against the Days of treatment, in which the square points represent vehicle; circular points represent mAb 3.19.3; triangular points represent AZD6495; diamond points represent mAb 3.19.3 and AZD6495 combination.

Study 6.1 Determination of the Therapeutic Efficacy of mAb 3.19.3 in Combination with the CSF1R Antagonist AZD6495 in a MCF7 Breast Cancer Xenograft Model The anti-tumor activity of the anti-Angiopoietin-2 monoclonal antibody 3.19.3 in combination with the small molecule CSF1R tyrosine kinase inhibitor AZD6495 (4-[(2,4-difluorophenyl)amino]-7-ethoxy-6-(4-methylpiperazin-1-yl)quinoline-3-carboxamide) was evaluated in a xenograft model of human breast carcinoma using the MCF7 cell line (FIG. 4a).

Materials and Methods: Breast carcinoma MCF7 cells were cultured in flasks as routine until the cells reach sub-confluence. Immunodeficient 7-10 week old male NCr-nude mice were subcutaneously implanted with $8 \times 10^6$ MCF7 cells suspended 1:1 in Matrigel in the right flank. 17-B-Estradiol pellets (0.72 mg/pellet) were also implanted as standard procedure to support the growth of this ER positive (estrogen requiring) cell line.

The mice were then randomized into cohorts containing 15 mice once the tumors reached approximately 100 mm$^3$. The mice were treated by intraperitoneally (IP) injection with mAb 3.19.3 (10 mg/kg) twice per week for 3 weeks thereafter, or by oral administration of CSF1R inhibitor A(AZD6495) at (30 mg/kg) following bid dosing for 18 days. For all experiments, 0.5% HPMC was used as an oral vehicle only control. The body weights of each animal, and the dimensions of each tumor were measured twice per week. The volume of the tumor was calculated as: Volume=Length×(Width)$^2$×0.5 cm$^3$, or by bilateral Vernier caliper measurement and, taking length to be the longest diameter across the tumor and width the corresponding perpendicular, calculated using the formula $(\pi/6) \times (\text{length} \times \text{width}) \times \sqrt{(\text{length} \times \text{width})}$. Growth inhibition from the start of treatment was assessed by comparison of the differences in tumor volume between control and treated groups. The summary study design was as follows:

TABLE 4

Study design

| Group | Treatment | # Mice | Schedule | Route |
|---|---|---|---|---|
| A | Veh (0.5% HPMC) | 15 | bid x 18 d | p.o. |
| B | mAb3.19.3, 10 mg/kg | 15 | q3.5 d x 3 wk | i.p. |
| C | AZD6495, 30 mg/kg | 15 | bid x 18 d | p.o. |
| D | mAb3.19.3, 10 mg/kg + AZD6495, 30 mg/kg | 15 | q3.5 d x 3 wk bid x 18 d | i.p. p.o. |

Figure 3:
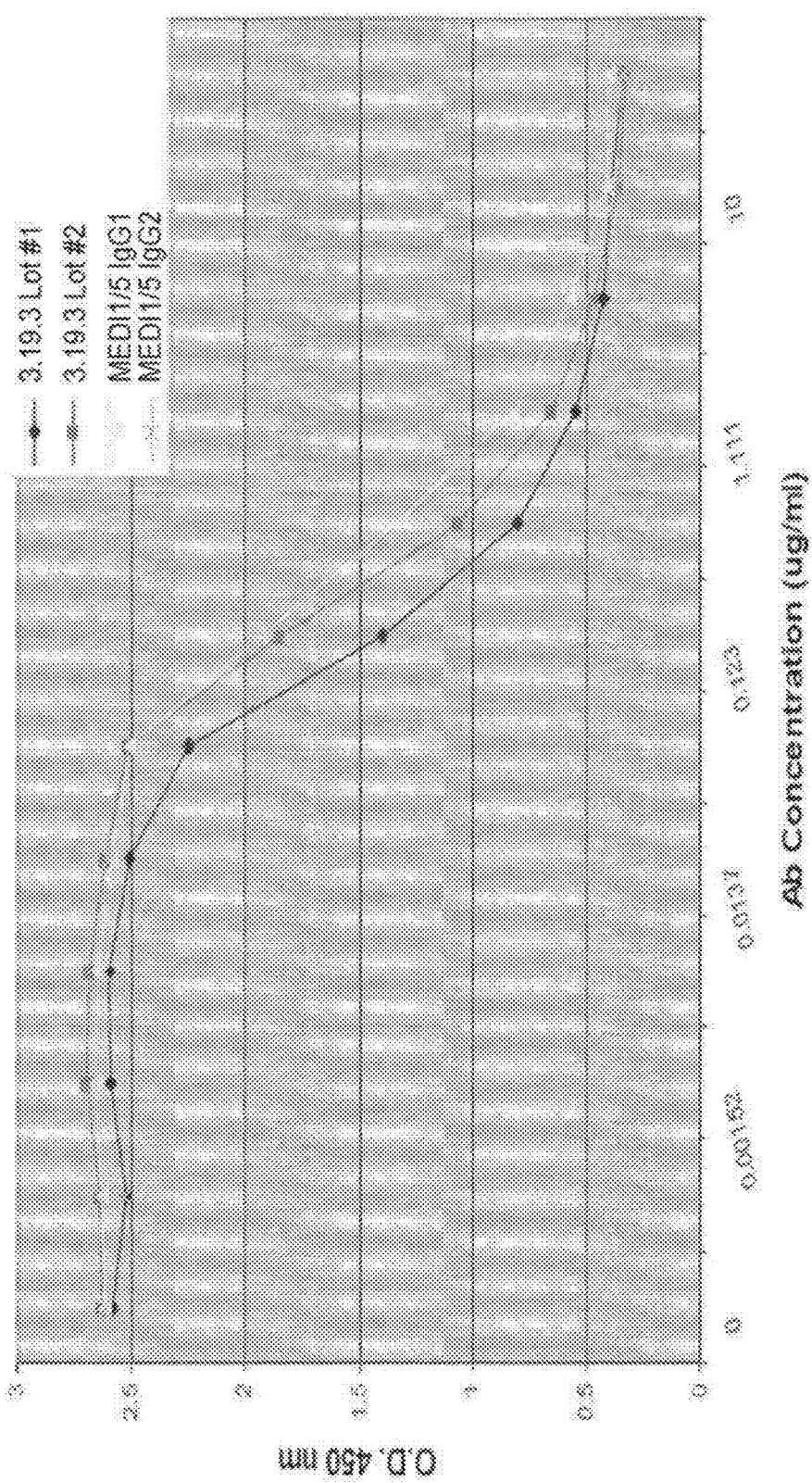
FIG. 3 represents the results from a competition ELISA based Ang-2 binding assay performed on wild type 3.19.3 antibodies as well as MEDI1/5 antibodies in an IgG1 or an IgG2 format. The figure depicts that the MEDI1/5 antibodies exhibit a similar binding profile for Ang-2 as compared to the 3.19.3 antibody as measured by a competition assay with immobilized Tie-2.

As illustrated in FIG. 4a, 3.19.3 and AZD6495 delayed the growth of the MCF7 tumors as single agents. However the combination of 3.19.3 and AZD6495 had a greater effect than the single agents alone as illustrated in FIG. 4a. The % tumor growth inhibition achieved is as follows:
  3.19.3 (10 mg/kg 2×wk)=62% inhibition; (p<0.04)
  AZD6495 (30 mg/kg bid)=32% inhibition; (p<0.42)
  Combination 3.19.3+AZD6495=81% inhibition (p<0.01)

Figure 4B:
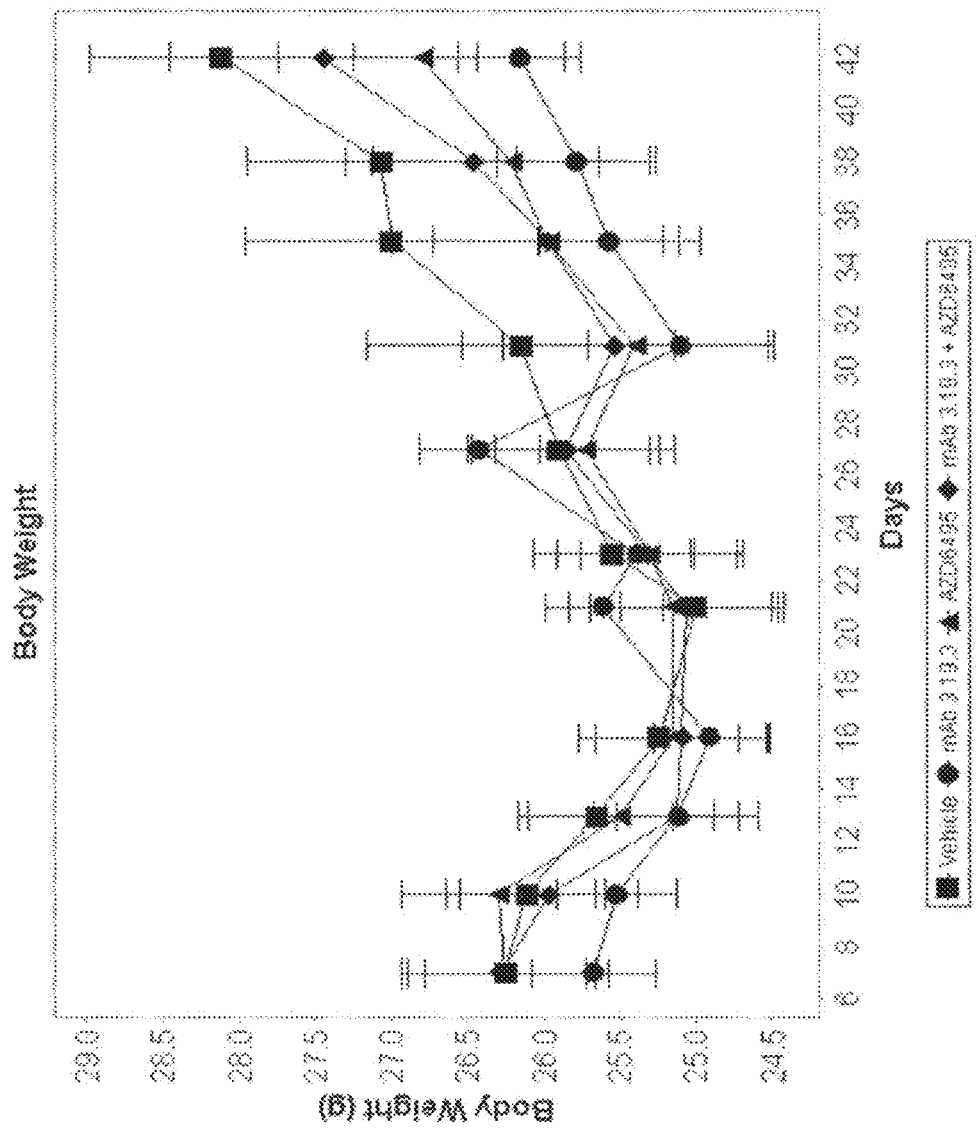
FIG. 4B demonstrates effects on host body weight changes following combination treatment with mAb 3.19.3 and AZD6495 in mice bearing MCF7 xenograft tumors. The y axis shows the Body weight in g, against the Days of treatment, in which the square points represent vehicle; circular points represent mAb 3.19.3; triangular points represent AZD6495; diamond points represent mAb 3.19.3 and AZD6495 combination.

No additional toxicity was observed with the combinations as compared to single-agent treatment alone as determined by changes in body weights (FIG. 4b). Changes in macrophage populations are being measured via F4/80 staining and Fluorescence Activated Cell Sorting and the tumor tissue analyzed via CD31+ vessel staining density to examine any effects on the tumor associated vasculature. CD31 staining density can be measured by threshold and by manual grid counting methods. The combination of 3.19.3 with CSF1R tyrosine kinase inhibitors is expected to produce a significantly greater effect on both tumor associated macrophage populations and CD31 staining blood vessels.

These results demonstrate that combination treatment with the anti-Ang2 antibody 3.19.3 and the small molecule CSF1R antagonist, AZD6495, leads to improvements in efficacy without additive toxicity in a pre-clinical model of breast cancer.

Figure 5A:
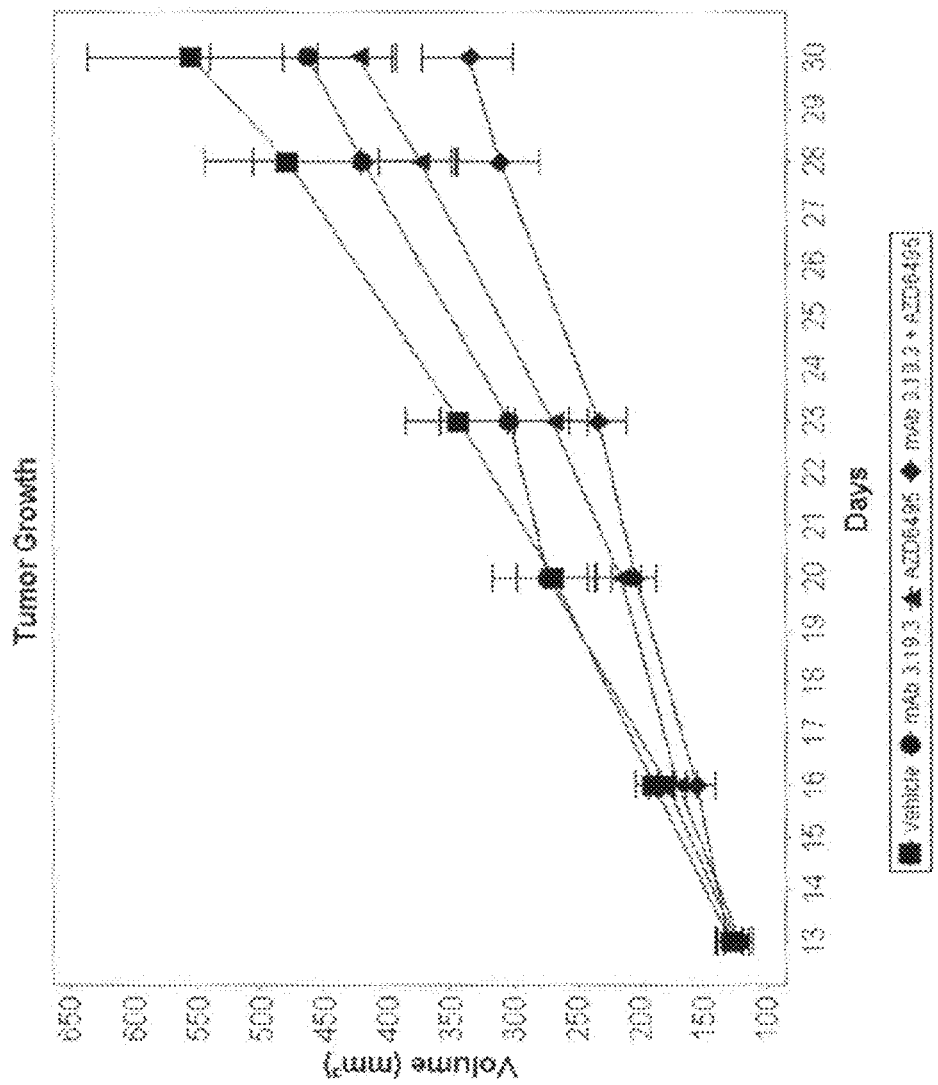
FIG. 5A demonstrates combination efficacy following treatment with mAb 3.19.3 and AZD6495 in mice bearing MDA-MB-231 xenograft tumors. The y axis shows the Tumor volume in $mm^3$, against the Days of treatment, in which the square points represent vehicle; circular points represent mAb 3.19.3; triangular points represent AZD6495; diamond points represent mAb 3.19.3 and AZD6495 combination.

Study 6.2. Determination of the Therapeutic Efficacy of mAb 3.19.3 in Combination with the CSF1R Antagonist AZD6495 in a MDA-MB-231 Orthotopic Breast Cancer Xenograft Model The anti-tumor activity of the anti-Angiopoietin-2 monoclonal antibody 3.19.3 in combination with the small molecule CSF1R tyrosine kinase inhibitor AZD6495 was evaluated in a xenograft model of human breast carcinoma using the MDA-MB-231 cell line (FIG. 5a).

Breast adenocarcinoma MDA-MB-231 cells were cultured in flasks as routine until the cells reach sub-confluence. Immunodeficient 7-10 week old female nude mice were orthotopically implanted with $8 \times 10^6$ MDA-MB-231 cells suspended 1:1 in Matrigel into the mammary fat pad. The mice were then randomized into cohorts containing 10 mice once the tumors reached approximately 100 mm$^3$. The mice were treated by intraperitoneally (IP) injection with mAb 3.19.3 (10 mg/kg) twice per week for 3 weeks thereafter, or by oral administration of AZD6495 (30 mg/kg) following bid dosing for 18 days. For all experiments, 0.5% HPMC was used as an oral vehicle only control. The body weights of each animal, and the dimensions of each tumor were measured twice per week. The volume of the tumor was calculated as: Volume=Length×(Width)$^2$×0.5 cm$^3$, or by bilateral Vernier caliper measurement and, taking length to be the longest diameter across the tumor and width the corresponding perpendicular, calculated using the formula $(\pi/6) \times (\text{length} \times \text{width}) \times \sqrt{(\text{length} \times \text{width})}$. Growth inhibition from the start of treatment was assessed by comparison of the differences in tumor volume between control and treated groups.

The summary study design was as follows;

TABLE 5

Study design

| Group | Treatment | # Mice | Schedule | Route |
|---|---|---|---|---|
| A | Veh (0.5% HPMC) | 10 | bid x 18 d | p.o. |
| B | mAb3.19.3, 10 mg/kg | 10 | q3.5 d x 3 wk | i.p. |
| C | AZD6495, 30 mg/kg | 10 | bid x 18 d | p.o. |
| D | mAb3.19.3, 10 mg/kg + AZD6495, 30 mg/kg | 10 | q3.5 d x 3 wk bid x 18 d | i.p. p.o. |

As illustrated in Figure 5a, 3.19.3 and AZD6495 delayed the growth of the MDA-MB-231 tumors as single agents. However the combination of 3.19.3 and AZD6495 had a greater effect than the single agents alone as illustrated in FIG. 5a. The % tumor growth inhibition achieved is as follows:
  3.19.3 (10 mg/kg 2×wk)=17% inhibition; (p<0.20)
  AZD6495 (30 mg/kg bid)=25% inhibition; (p<0.04)
  Combination 3.19.3+AZD6495=52% inhibition (p<0.09)

Figure 5B:
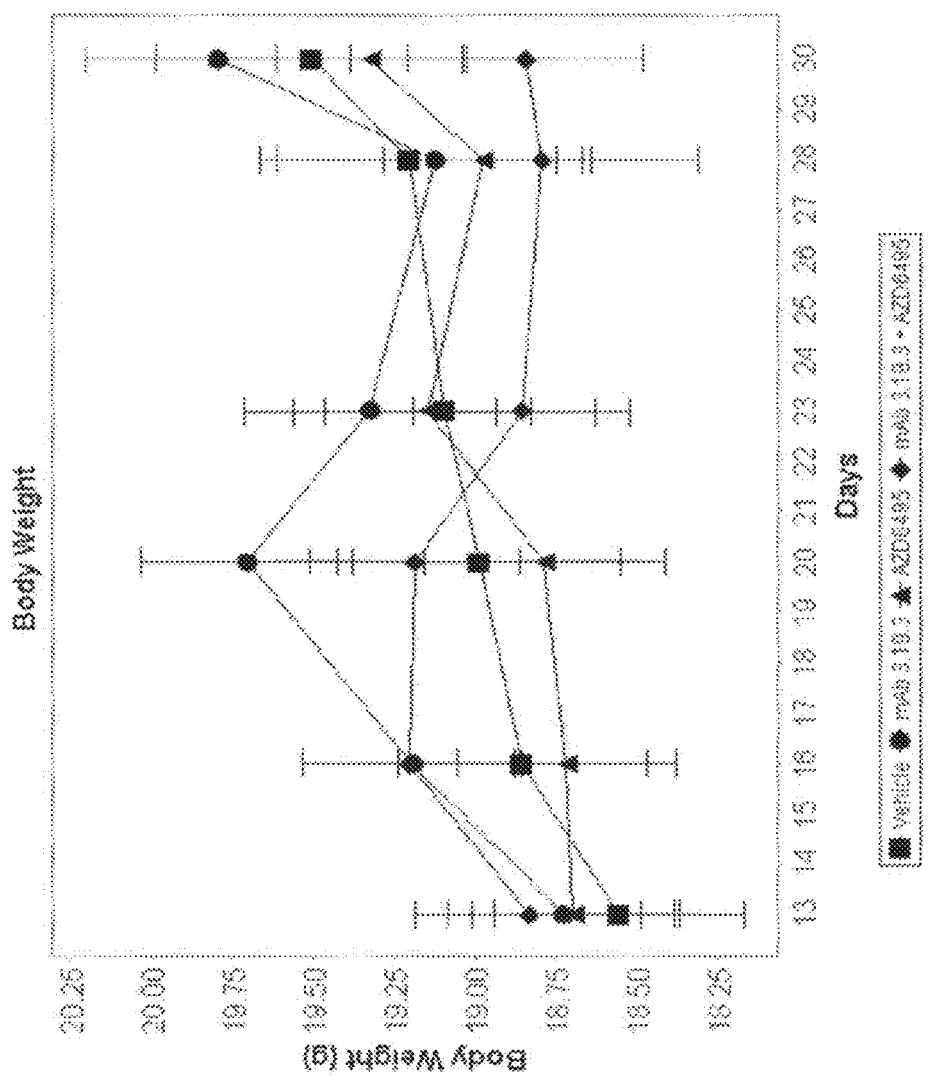
FIG. 5B Shows effects on host body weight changes following combination treatment with mAb 3.19.3 and AZD6495 in mice bearing MDA-MB-231 xenograft tumors. The y axis shows the Body weight in g, against the Days of treatment, in which the square points represent vehicle; circular points represent mAb 3.19.3; triangular points represent AZD6495; diamond points represent mAb 3.19.3 and AZD6495 combination.

No additional toxicity was observed with the combinations as compared to single-agent treatment alone as determined by changes in body weights (FIG. 5b). Changes in macrophage populations are being measured via F4/80 staining and Fluorescence Activated Cell Sorting and the tumor tissue analyzed via CD31+ vessel staining density to examine any effects on the tumor associated vasculature. CD31 staining density can be measured by threshold and by manual grid counting methods. The combination of 3.19.3 with CSF1R tyrosine kinase inhibitors is expected to produce a significantly greater effect on both tumor associated macrophage populations and CD31 staining blood vessels.

These results demonstrate that combination treatment with the anti-Ang2 antibody 3.19.3 and the small molecule CSF1R antagonist AZD6495 leads to improvements in efficacy without additive toxicity in a pre-clinical model of breast cancer.

Example 7: Combination Studies

The activity of the monoclonal antibody 3.19.3 was evaluated in combination studies with chemotherapeutic agents to determine the in vivo efficacy and tolerability in human tumor xenograft models.

Figure 6A:
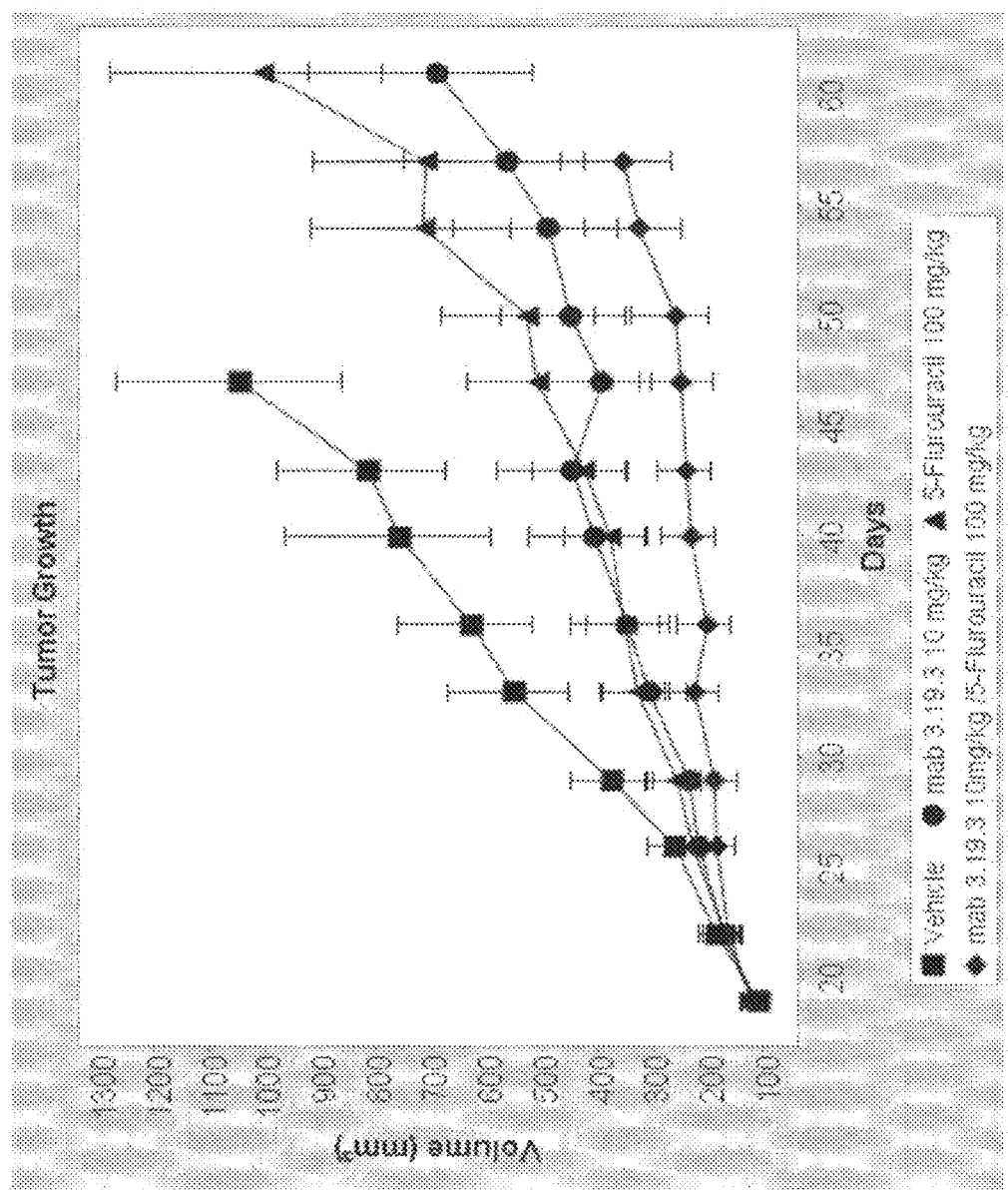
FIG. 6A Shows combination efficacy following treatment with mAb 3.19.3 and 5-flurouracil in mice bearing LoVo xenograft tumors.

Study 7.1. Determination of the Therapeutic Efficacy of Monoclonal Antibody 3.19.3 in Combination with 5-Flurouracil in LoVo Xenograft Tumors The anti-tumor activity of 3.19.3 was evaluated in combination with 5-Fluoruracil (5FU) in the LoVo xenograft model of colorectal cancer. LoVo cells were cultured in flasks as routine until the cells reached sub-confluence. Cell suspensions containing approximately 3×10E6 cells were injected subcutaneously into the flank of female Swiss nude mice. When the tumor volume reached 200 mm$^3$, the mice were randomized in treatment groups of 8-10 mice and the treatments were initiated. 3.19.3 (10 mg/kg) in saline was injected intraperitoneally, twice per week for 2 weeks and 5-Flurouracil (100 mg/kg) was administered by intraperitoneal administration following a weekly schedule. The dimensions of each tumor and body weights were measured at least twice per week. The volume of the tumor was calculated as: Volume=Length×(Width)$^2$×0.5 (cm$^3$). As illustrated in FIG. 6a, 3.19.3 and 5FU delayed the growth of the LoVo tumors as single agent. However the combination of 3.19.3 and 5FU had a greater effect than the single agents alone as illustrated in FIG. 6a. The % tumor growth inhibition achieved is as follows:

3.19.3 (10 mg/kg 2×wk)=59% inhibition; (p<0.09)
5 FU (100 mg/kg/week)=62% inhibition; (p<0.02)
Combination 3.19.3+5FU=85% inhibition (p<0.007)

Figure 6B:
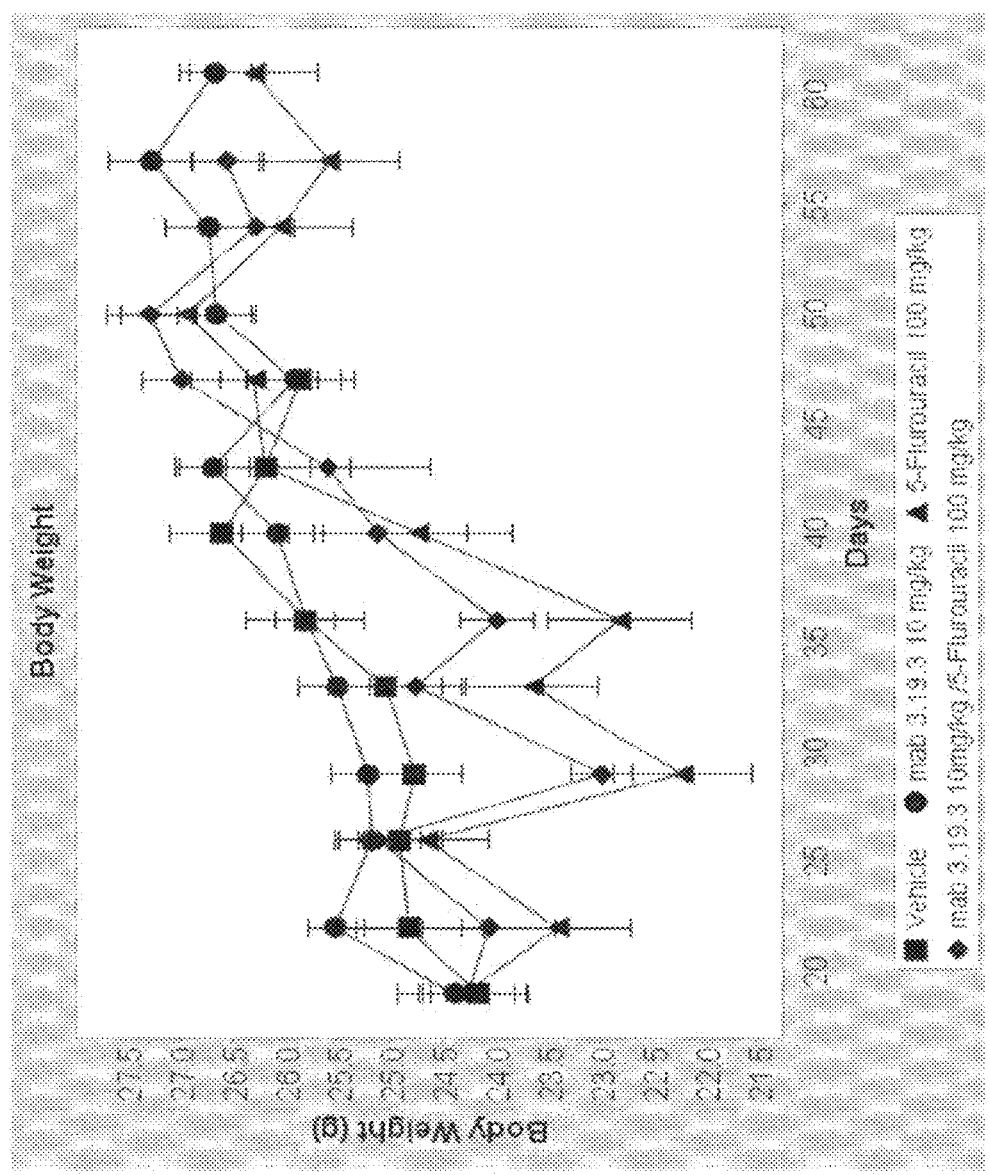
FIG. 6B Shows effects on host body weight changes following combination treatment with mAb 3.19.3 and 5-fluoruracil in mice bearing LoVo xenograft tumors.

No additional toxicity was observed with the combinations as compared to single-agent treatment alone as determined by changes in body weights (FIG. 6b). These results demonstrate that combination treatment with the anti-Ang2 antibody 3.19.3 and 5-flurouracil leads to improvements in efficacy without additive toxicity in a pre-clinical model of colon cancer, providing the basis for further clinical investigation of this combination.

Figure 7A:
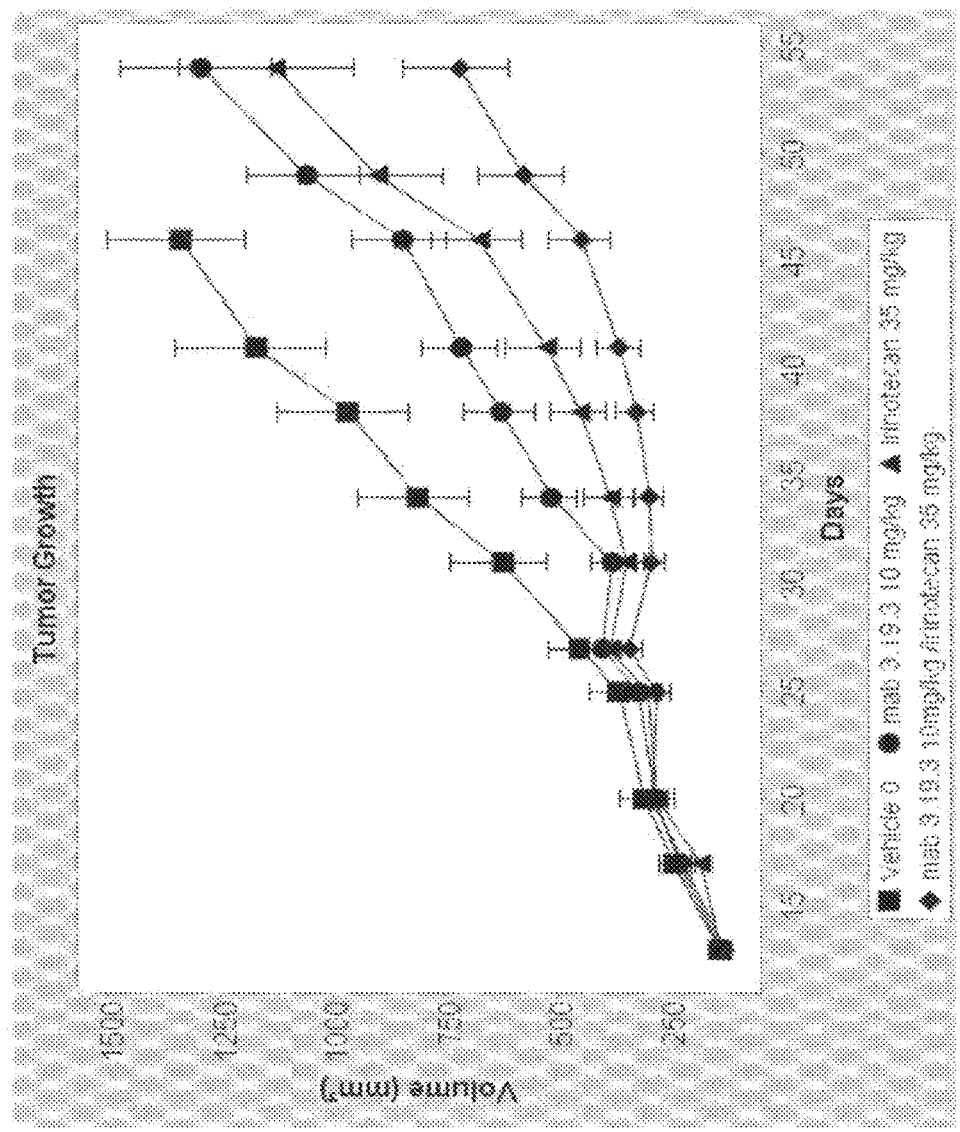
FIG. 7A Shows combination efficacy following treatment with mAb 3.19.3 and Irinotecan in mice bearing HT-29 xenograft tumors.

Study 7.2. Determination of the Therapeutic Efficacy of Monoclonal Antibody 3.19.3 in Combination with Irinotecan in HT-29 Xenograft Tumors The anti-tumor activity of 3.19.3 was evaluated in combination with Irinotecan in the HT-29 xenograft model of colorectal cancer. HT-29 cells were cultured in flasks as routine until the cells reached sub-confluence. Cell suspensions containing approximately 3×10E6 cells were injected subcutaneously into the flank of female Swiss nude mice. When the tumor volume reached 200 mm$^3$, the mice were randomized in treatment groups of 8-10 mice and the treatments were initiated. 3.19.3 (10 mg/kg) in saline was injected intraperitoneally, twice per week for 2 weeks. Irinotecan (35 mg/kg) was administered by intravenous administration following a weekly schedule. The dimensions of each tumor and body weights were measured at least twice per week. The volume of the tumor was calculated as: Volume=Length×(Width)$^2$×0.5 (cm$^3$). As illustrated in FIG. 7a, 3.19.3 and Irinotecan delayed the growth of the HT29 tumors as single agents. However the combination of 3.19.3 and Irinotecan had a greater effect than the single agents alone as illustrated in FIG. 7a. The % tumor growth inhibition achieved is as follows:

3.19.3 (10 mg/kg 2×wk)=44% inhibition; (p<0.005)
Irinotecan (35 mg/kg/week)=56% inhibition; (p<0.006)
Combination 3.19.3+Irinotecan=71% inhibition (p<0.0001)

Figure 7B:
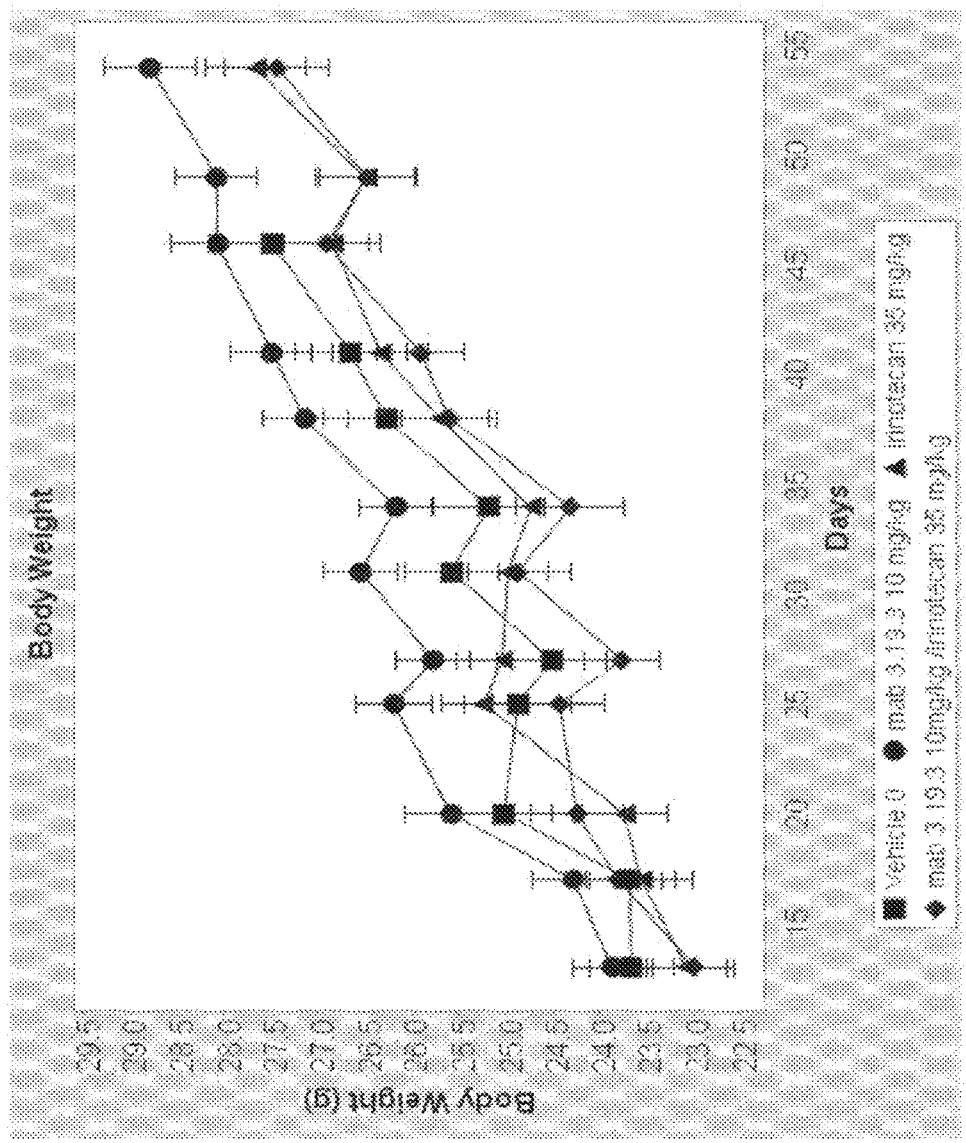
FIG. 7B Shows effects on host body weight changes following combination treatment with mAb 3.19.3 and Irinotecan in mice bearing HT29 xenograft tumors.

No additional toxicity was observed with the combinations as compared to single-agent treatment alone as determined by changes in body weights (FIG. 7b). These results demonstrate that combination treatment with anti-Ang2 antibody 3.19.3 and Irinotecan leads to improvements in efficacy without additive toxicity in a pre-clinical model of colon cancer, and providing the basis for further clinical investigation of this combination.

Figure 8A:
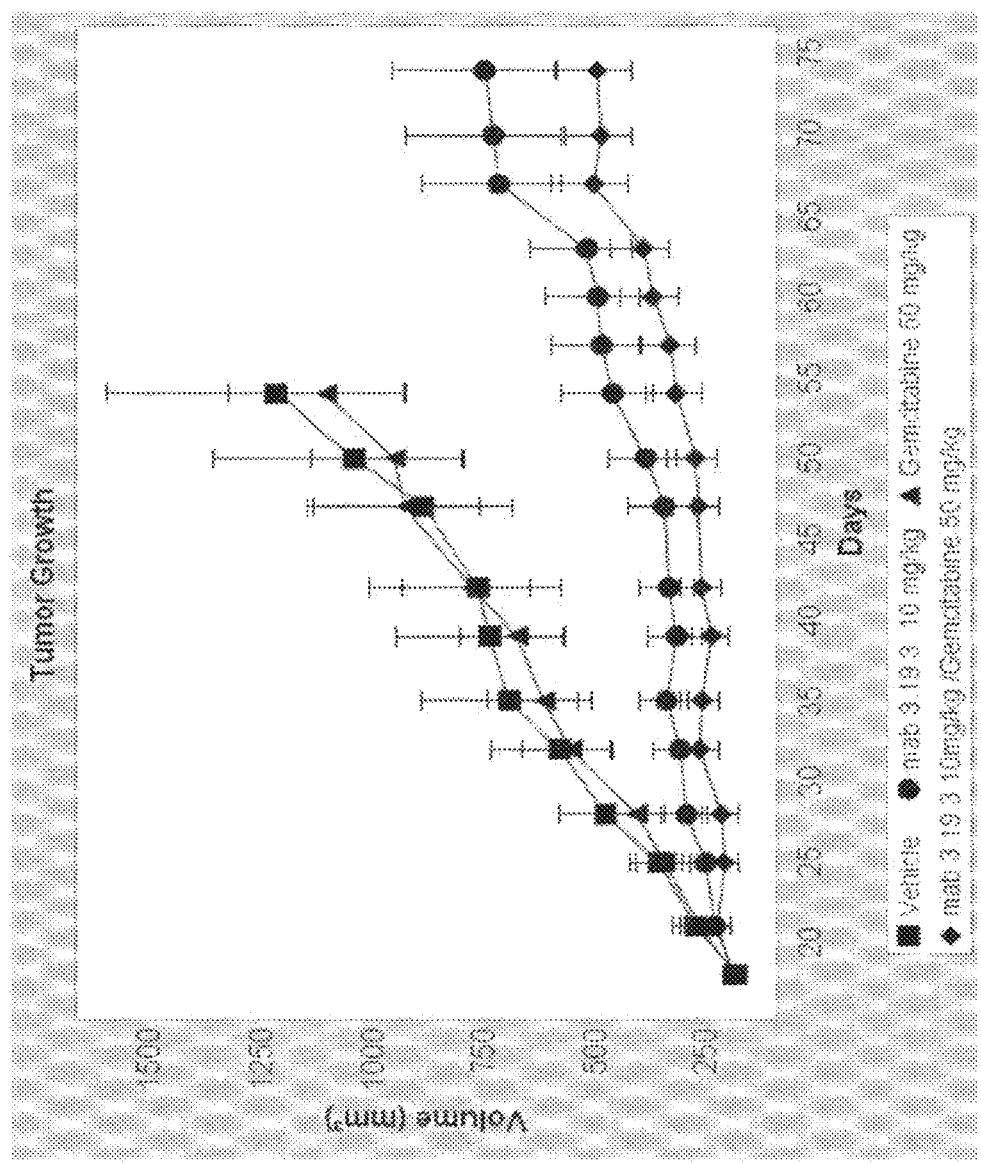
FIG. 8A Shows combination efficacy following treatment with mAb 3.19.3 and Gemcitabine in mice bearing Colo205 xenograft tumors.

Study 7.3. Determination of the Therapeutic Efficacy of Monoclonal Antibody 3.193 in Combination with Gemcitabine in Colo205 Xenograft Tumors The anti-tumor activity of 3.19.3 was evaluated in combination with Gemcitabine in the Colo205 xenograft model of colorectal cancer. Colo205 cells were cultured in flasks as routine until the cells reached sub-confluence. Cell suspensions containing approximately 3×10E6 cells were injected subcutaneously into the flank of female Swiss nude mice. When the tumor volume reached 200 mm$^3$, the mice were randomized in treatment groups of 8-10 mice and the treatments were initiated. 3.19.3 (10 mg/kg) in saline was injected intraperitoneally, twice per week for 2 weeks. Gemcitabine (50 mg/kg) was administered by intravenous administration following a q3d schedule. The dimensions of each tumor and body weights were measured at least twice per week. The volume of the tumor was calculated as: Volume=Length×(Width)$^2$×0.5 (cm$^3$). As illustrated in FIG. 8a, 3.19.3 delayed the growth of the Colo205 tumors as single agent however the Colo205 tumors were fairly refractory to Gemcitabine treatment resulting in a modest 8% tumor growth delay. However the combination of 3.19.3 and Gemcitabine had a greater effect than the single agents alone as illustrated in FIG. 8a. The % tumor growth inhibition achieved is as follows:

3.19.3 (10 mg/kg 2×wk)=74% inhibition; (p<0.001)
Gemcitabine (50 mg/kg q3d×2)=8% inhibition; (p<0.2)
Combination 3.19.3+Gemcitabine=88% inhibition (p<0.0003)

Figure 8B:
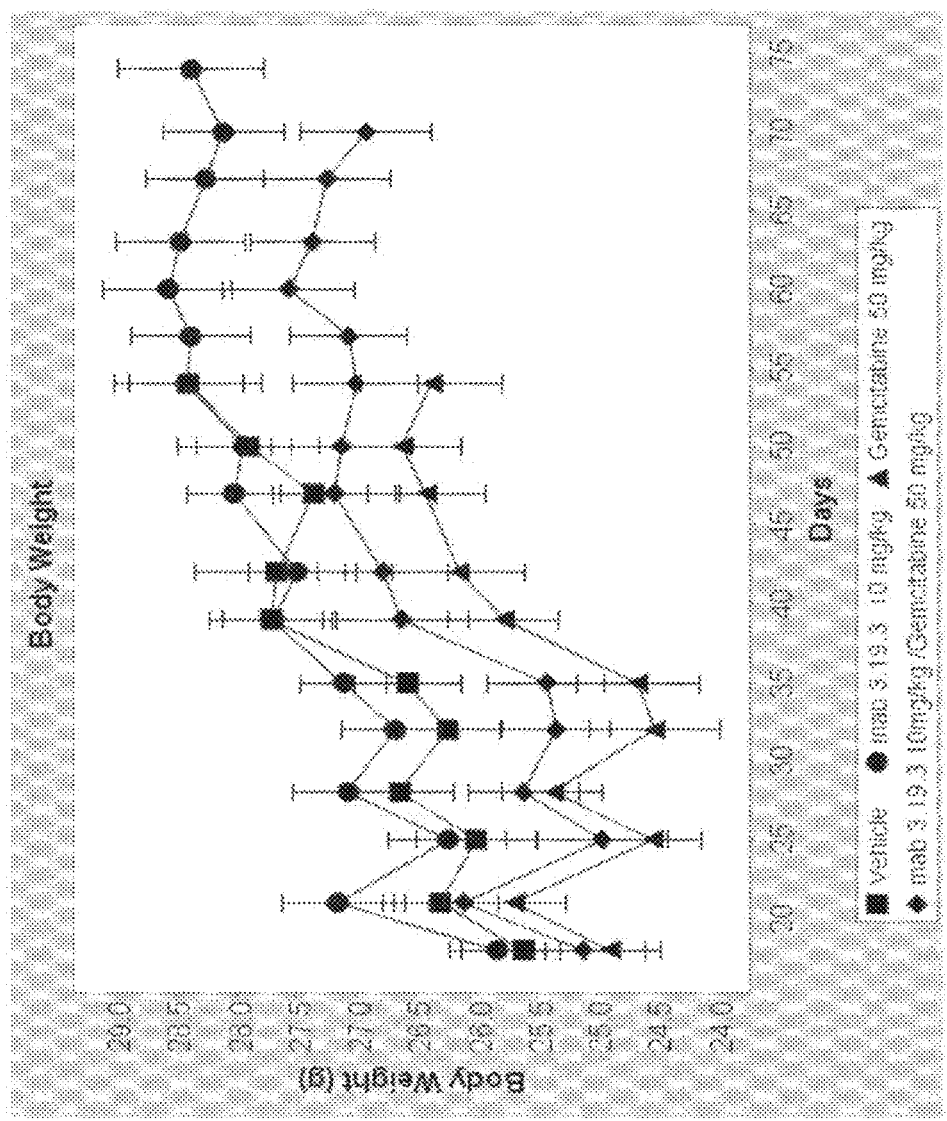
FIG. 8B Shows effects on host body weight changes following combination treatment with mAb 3.19.3 and Gemcitabine in mice bearing Colo205 xenograft tumors.

No additional toxicity was observed with the combinations as compared to single-agent treatment alone as determined by changes in body weights (FIG. 8b). These results demonstrate that combination treatment with anti-Ang2 antibody 3.19.3 and Gemcitabine leads to improvements in efficacy without additive toxicity in a pre-clinical model of colon cancer, and providing the basis for further clinical investigation of this combination.

Figure 9A:
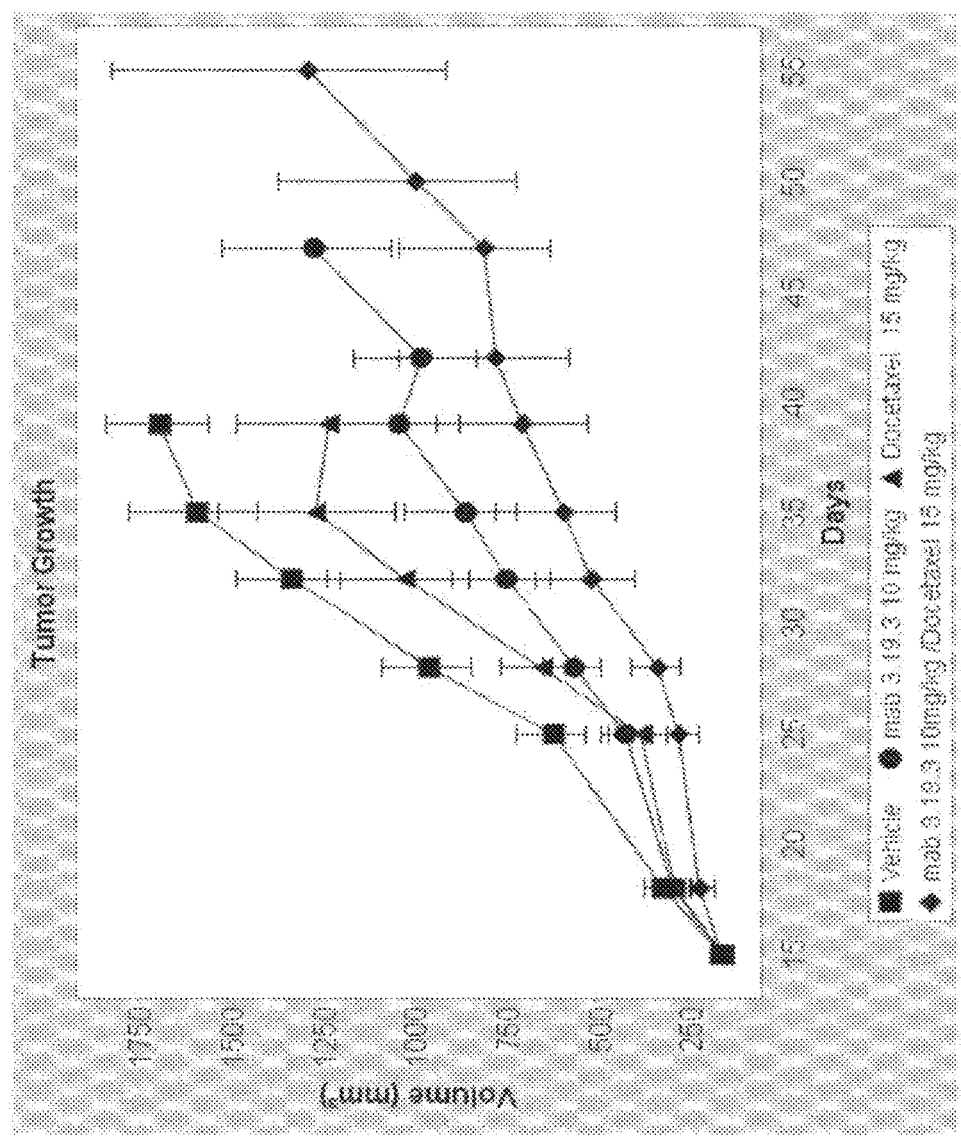
FIG. 9A Shows combination efficacy following treatment with mAb 3.19.3 and Docetaxel in mice bearing Calu6 xenograft tumors.

Study 7.4. Determination of the Therapeutic Efficacy of Monoclonal Antibody 3.19.3 in Combination with Docetaxel in Calu6 Xenograft Tumors The anti-tumor activity of 3.19.3 was evaluated in combination with Docetaxel in the Calu6 xenograft model of lung cancer. Calu6 cells were cultured in flasks as routine until the cells reached sub-confluence. Cell suspensions containing approximately 3×10E6 cells were injected subcutaneously into the flank of female Swiss nude mice. When the tumor volume reached 200 mm$^3$, the mice were randomized in treatment groups of 8-10 mice and the treatments were initiated. 3.19.3 (10 mg/kg) in saline was injected intraperitoneally, twice per week for 2 weeks. Docetaxel (15 mg/kg) was administered by intravenous administration following a weekly schedule. The dimensions of each tumor and body weights were measured at least twice per week. The volume of the tumor was calculated as: Volume=Length×(Width)$^2$×0.5 (cm$^3$). As illustrated in FIG. 9a, 3.19.3 and Docetaxel delayed the growth of the Calu6 tumors with the single agents. However the combination of 3.19.3 and Docetaxel had a greater effect than the single agents alone as illustrated in FIG. 9a. The % tumor growth inhibition achieved is as follows:

3.19.3 (10 mg/kg 2×wk)=: 20% inhibition; ($p<0.12$)
Docetaxel (15 mg/kg/week)=43% inhibition; ($p<0.0007$)
Combination 3.19.3+Docetaxel=71% inhibition ($p<0.0001$)

Figure 9B:
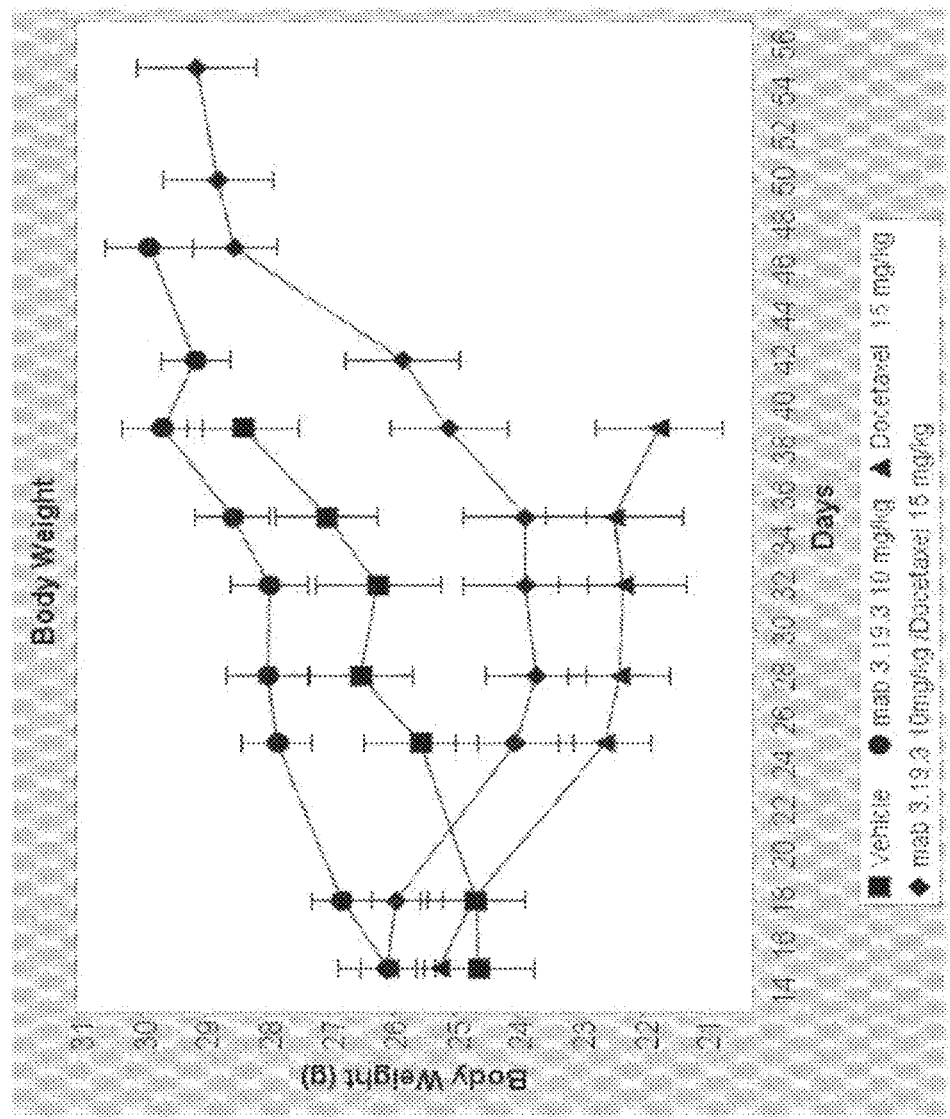
FIG. 9B Shows effects on host body weight changes following combination treatment with mAb 3.19.3 and Docetaxel in mice bearing Calu6 xenograft tumors.

No additional toxicity was observed with the combinations as compared to single-agent treatment alone as determined by changes in body weights (FIG. 9b). These results demonstrate that combination treatment with anti-Ang2 antibody 3.19.3 and Docetaxel leads to improvements in efficacy without additive toxicity in a pre-clinical model of lung cancer, and providing the basis for further clinical investigation of this combination.

Figure 10A:
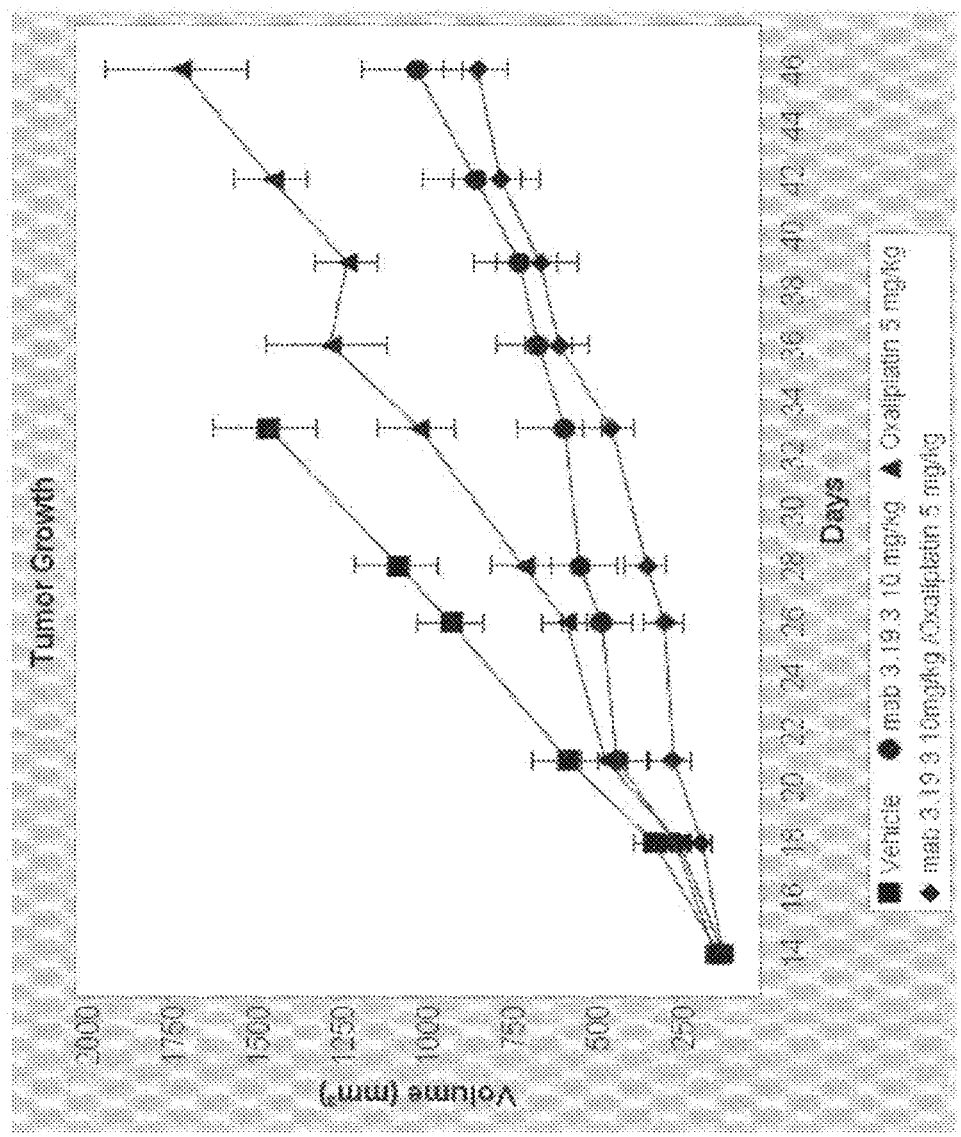
FIG. 10A Shows combination efficacy following treatment with mAb 3.19.3 and Oxaliplatin in mice bearing H460 xenograft tumors.

Study 7.5. Determination of the Therapeutic Efficacy of Monoclonal Antibody 3.19.3 in Combination with Oxaliplatin in H460 Xenograft Tumors The anti-tumor activity of 3.19.3 was evaluated in combination with Oxaliplatin in the H1460 xenograft model of lung cancer. H460 cells were cultured in flasks as routine until the cells reached sub-confluence. Cell suspensions containing approximately 3×10E6 cells were injected subcutaneously into the flank of female Swiss nude mice. When the tumor volume reached 200 mm$^3$, the mice were randomized in treatment groups of 8-10 mice and the treatments were initiated. 3.19.3 (10 mg/kg) in saline was injected intraperitoneally, twice per week for 2 weeks. Oxaliplatin (5 mg/kg) was administered by intraperitoneal administration following a weekly schedule. The dimensions of each tumor and body weights were measured at least twice per week. The volume of the tumor was calculated as: Volume=Length×(Width)$^2$×0.5 (cm$^3$). As illustrated in FIG. 10a, 3.19.3 and Oxaliplatin delayed the growth of the H460 tumors with the single agents. However the combination of 3.19.3 and Oxaliplatin had a greater effect than the single agents alone as illustrated in FIG. 10a. The % tumor growth inhibition achieved is as follows:

3.19.3 (10 mg/kg 2×wk)=67% inhibition; ($p<0.001$)
Oxaliplatin (5 mg/kg/week)=35% inhibition; ($p<0.01$)
Combination 3.19.3+Oxaliplatin=75% inhibition ($p<0.0001$)

Figure 10B:
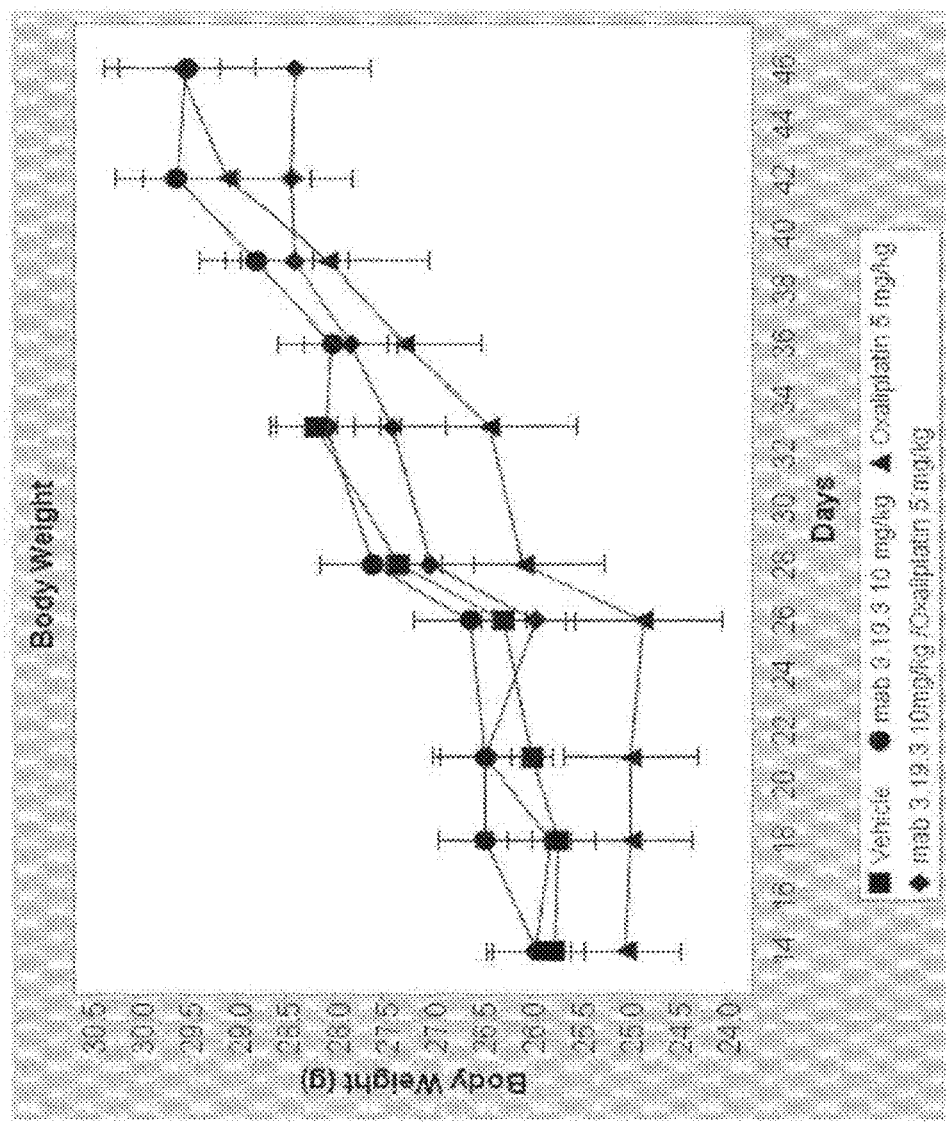
FIG. 10B Shows effects on host body weight changes following combination treatment with mAb 3.19.3 and Oxaliplatin in mice bearing H1460 xenograft tumors.

No additional toxicity was observed with the combinations as compared to single-agent treatment alone as determined by changes in body weights (FIG. 10b). These results demonstrate that combination treatment with anti-Ang2 antibody 3.19.3 and Oxaliplatin leads to improvements in efficacy without additive toxicity in a pre-clinical model of lung cancer, and providing the basis for further clinical investigation of this combination.

Figure 11A:
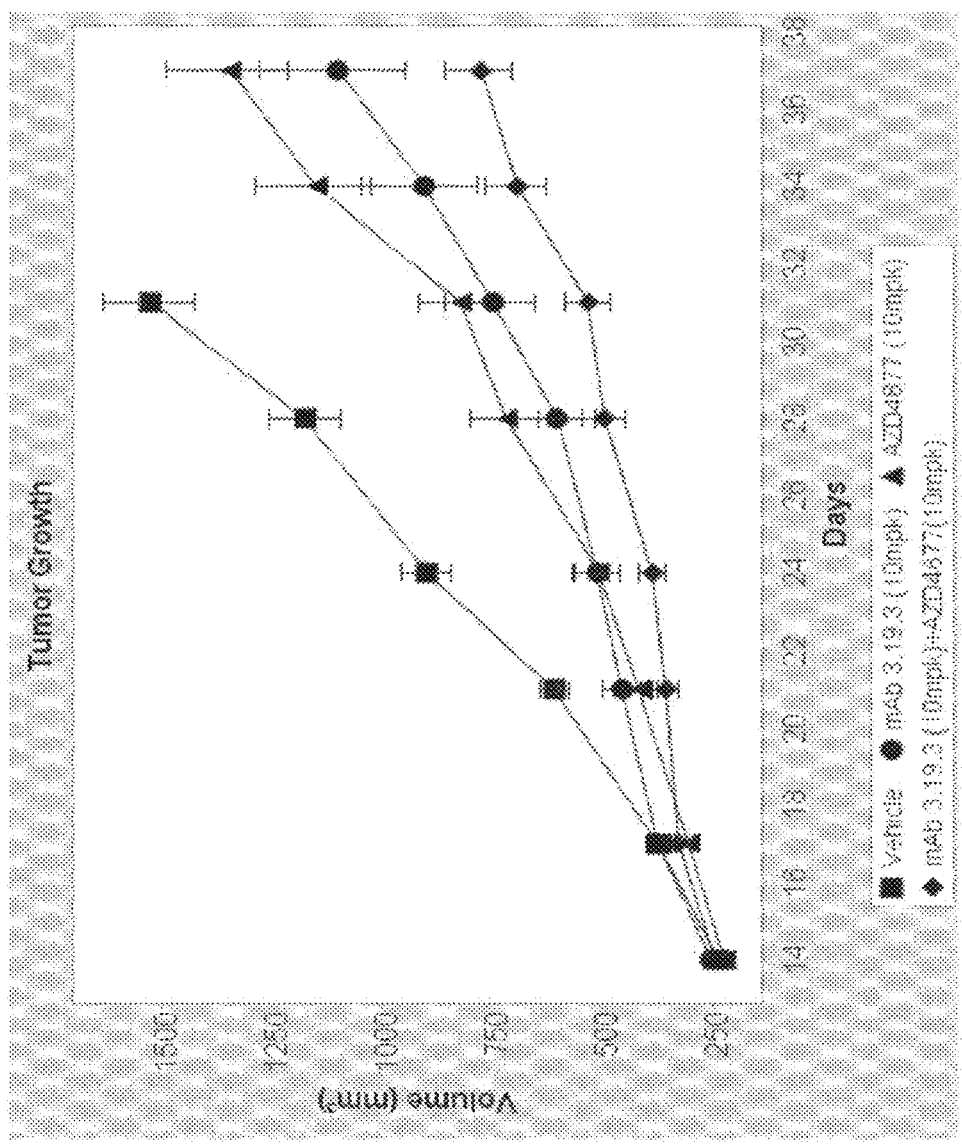
FIG. 11A Shows combination efficacy following treatment with mAb 3.19.3 and AZD4877 in mice bearing H460 xenograft tumors.

Study 7.6. Determination of the Therapeutic Efficacy of Monoclonal Antibody 3.19.3 in Combination with the Mitotic Eg5 Inhibitor AZD4877 in H460 Xenograft Tumors The anti-tumor activity of 3.19.3 was evaluated in combination with AZD4877 in the H1460 xenograft model of lung cancer. H460 cells were cultured in flasks as routine until the cells reached sub-confluence. Cell suspensions containing approximately 3×10E6 cells were injected subcutaneously into the right flank of male NCr nu/nu mice. When the tumor volume reached 200 mm$^3$, the mice were randomized in treatment groups of 8-10 mice and the treatments were initiated. 3.19.3 (10 mg/kg) in saline was injected intraperitoneally, twice per week for 2 weeks. AZD4877 (10 mg/kg) was administered by intraperitoneal administration following a q4d schedule. The dimensions of each tumor and body weights were measured at least twice per week. The volume of the tumor was calculated as: Volume=Length×(Width)$^2$×0.5 (cm$^3$). As illustrated in FIG. 11a, 3.19.3 and AZD4877 delayed the growth of the H460 tumors with the single agents. However the combination of 3.19.3 and AZD4877 had a greater effect than the single agents alone as illustrated in FIG. 11a. The % tumor growth inhibition achieved is as follows:

3.19.3 (10 mg/kg 2×wk)=64% inhibition; ($p<0.001$)
AZD4877 (10 mg/kg q4d×2)=50% inhibition; ($p<0.001$)
Combination 3.19.3+AZD4877=78% inhibition ($p<0.0001$)

Figure 11B:
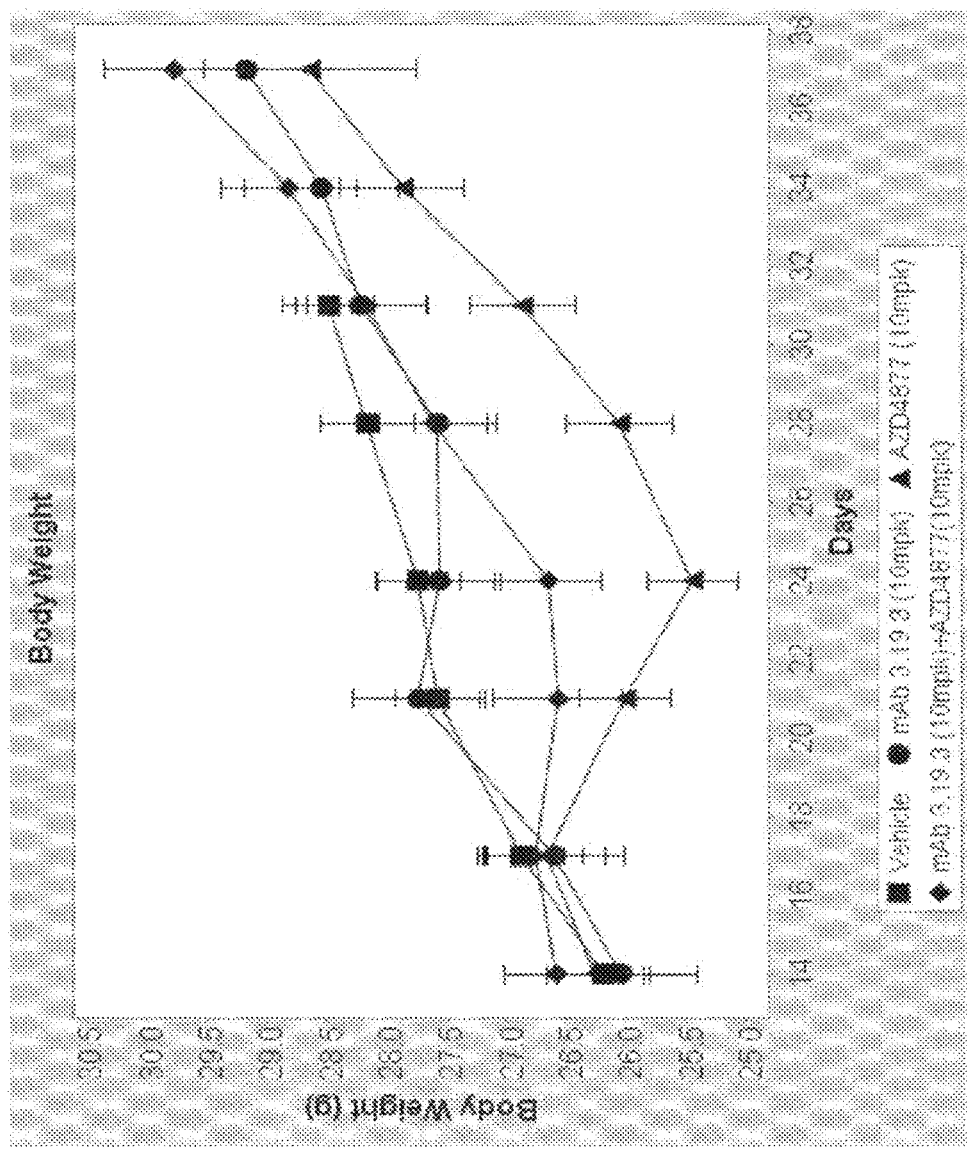
FIG. 11B Shows effects on host body weight changes following combination treatment with mAb 3.19.3 and AZD4877 in mice bearing H460 xenograft tumors.

No additional toxicity was observed with the combinations as compared to single-agent treatment alone as determined by changes in body weights (FIG. 11b). These results demonstrate that combination treatment with anti-Ang2 antibody 3.19.3 and AZD4877 leads to improvements in efficacy without additive toxicity in a pre-clinical model of lung cancer, and providing the basis for further clinical investigation of this combination.

The studies of the anti Ang-2 antibody, 3.19.3 in combination with chemotherapeutic agents included Docetaxel, 5-flurouracil, Irinotecan, Oxaliplatin, or Gemcitabine which demonstrated at least additive activity with no increases in toxicity with the combinations as indicated by body weights. These results demonstrate that combination treatment with monoclonal antibody 3.19.3 and chemotherapy leads to improvements in efficacy without additive toxicity in pre-clinical models of cancer.

The results of the monoclonal antibody 3.19.3 xenograft combination studies with VEGF inhibitors and chemotherapeutic agents are summarized in below:

TABLE 6

Summary of 3.19.3 with VEGF inhibitors and chemotherapeutic agents:

| Xenograft | Chemotherapeutic Agent | % Inhibition | Significance (T-test) |
|---|---|---|---|
| Lovo | 5-flurouracil (100 mg/kg) | 62% | p < 0.02 |
| | 3.19.3 (10 mg/kg) | 59% | p < 0.09 |
| | Combination | 85% | p < 0.007 |
| HT-29 | Irinotecan (35 mg/kg) | 56% | p < 0.006 |
| | 3.19.3 (10 mg/kg) | 44% | p < 0.0005 |
| | Combination | 71% | p < 0.0001 |
| Colo205 | Gemcitabine (50 mg/kg) | 8% | p < 0.2 |
| | 3.19.3 (10 mg/kg) | 74% | p < 0.001 |
| | Combination | 88% | p < 0.0003 |

TABLE 6-continued

Summary of 3.19.3 with VEGF inhibitors and chemotherapeutic agents:

| Xenograft | Chemotherapeutic Agent | % Inhibition | Significance (T-test) |
|---|---|---|---|
| Calu6 | Docetaxel (15 mg/kg) | 43% | p < 0.0007 |
| | 3.19.3 (10 mg/kg) | 20% | p < 0.12 |
| | Combination | 71% | p < 0.0001 |
| H460 | Oxaliplatin (5 mg/kg) | 35% | p < 0.01 |
| | 3.19.3 (10 mg/kg) | 67% | p < 0.001 |
| | Combination | 75% | p < 0.0001 |

Example 8: Effect of Therapeutic Administration of the Ang-2 Antibody, 3.19.3 on Disease Progression in the DBA/1 Marine Model of Collagen Induced Arthritis In Vivo Preparation of rat collagen type 11 emulsion: Bovine Collagen Type II (MD Biosciences, Cat # IMBII; Lot 090205) was stored at 4° C. in the dark until use. Prior to immunisation of animals, bovine collagen was dissolved in 0.01 M acetic acid at a stock solution of 2 mg/mL and stored overnight in the dark at 4° C. On the day of immunisation, collagen was emulsified with equal volume of Freund's Complete Adjuvant (FCA [Difco, Cat #231131; Lot 850262/R1]) to give a solution at 1 mg/mL.

Induction of arthritis: On day 0, male DBA/1 mice (6-8 weeks old, Harlan Sprague Dawley, UK) were lightly anaesthetised with 3.5% isoflurane and immunized intra-dermal just above the root of the tail with 100 µg rat collagen type 11 emulsified in FCA (1 mg/mL; 0.1 mL/mouse).

Staphylococcal Enterotoxin B (SEB) booster: On day 21, all mice were anaesthetised as before and given a booster injection of 30 µg SEB (600 µg/ml in water for injections [Toxin Technology, Cat # BT202; Lot 70903] emulsified in an equal volume of Freund's Incomplete Adjuvant [Sigma, Cat # F5506; Lot 112K8930] to give a final concentration of 300 µg/ml). 50 µl×2 (equivalent to 30 µg SEB) is injected intra-dermal adjacent to the immunisation site.

Assessment of arthritis: Clinical observations regarding welfare of the animals were carried out daily at time of dosing. Observations for clinical signs of disease were carried out daily from day 20 post immunisation, whereby the animals were removed from their micro-environment, and scored using the scoring system outlined below.

TABLE 7

Scoring system for hind and forepaws

| Clinical score | Description |
|---|---|
| 0 | Normal |
| 1 | Erythema and slight swelling of one of more toes. |
| 2 | Erythema and obvious swelling of two or more toes, or mild swelling of the ankle or wrist without toe involvement. |
| 3 | Erythema and obvious swelling to some toes and ankle or fore paw and wrist. |
| 4 | Erythema and severe swelling of ankle and digits. |

Dosing:

Animals were randomly assigned to treatment groups, as outlined below.

TABLE 8

| Treatment groups | | |
|---|---|---|
| Group | Treatment | Number of animals |
| 1 | PBS Vehicle i.p | 15 |
| 2 | 3.19.3 10 mg/kg i.p | 15 |
| 3 | Human IgG control antibody i.p | 15 |
| 4 | Prednisolone 3 mg/kg p.o | 10 |

Animals in treatment group 2 were therapeutically dosed intraperitonealy (i.p.) with 3.19.3 10 mL/kg every 3 days for 14 days from disease onset (defined as a clinical score of 2 in one or more paw). Purified human IgG (hIgG) was used as a negative isotype control. Animals in treatment group 4 were therapeutically dosed per oral (p.o.) with Prednisolone 3 mg/kg daily for 14 days from disease onset (defined as a clinical score of 2 in one or more paw).

Termination: Animals were terminated 14 days post disease onset by exposure to rising concentration of carbon dioxide. Mouse paws were excised post mortem, fixed in 10% buffered formalin and decalcified. Decalcified paws were routinely processed and then embedded in paraffin blocks. Serial sections (10 µm) were cut and stained with hematoxylin and eosin for histologic analysis.

Data analysis: Area under the curve (AUC) for clinical disease progression was calculated for each animal from disease onset. Unless otherwise stated, statistical analysis was by one-way ANOVA with Dunnett's post-hoc comparison to vehicle controls. $P<0.05$ was considered to be statistically significant throughout the study.

Results: Significant reductions in both clinical signs of disease progression (arthritic score) and histological assessment of synovitis and joint destruction were observed with 3.19.3 at a dose of 10 mg/kg (One-Way ANOVA with Dunnett's post-hoc comparison to vehicle control).

TABLE 9

Therapeutic effects of 3.19.3 on CIA disease progression

| Treatment group | Area Under Curve (AUC) | % Inhibition |
|---|---|---|
| PBS Vehicle i.p | 100.9 ± 10.9 | — |
| 3.19.3 10 mg/kg i.p | 36.0 ± 8.7 | 64.3% ± 8.6% |
| hIgG isotype control i.p | 92.4 ± 11.2 | 8.4% ± 11.1% |
| Prednisolone 3 mg/kg p.o | 24.5 ± 9.6 | 76.1% ± 9.6% |

Table 9: Effect of therapeutic administration of 3.19.3 (10 mg/kg i.p every 3 days) on clinical disease progression throughout the time course of collagen-induced arthritis as measured by Area Under Curve [AUC] (values represent means±standard error of the mean, n=15 for 3.19.3, PBS vehicle and hIgG treatment groups, n=10 for Prednisolone control group)

Histolopathological evaluation of CIA model treatment groups: Results showed unequivocal evidence of an anti-arthritic effect following administration of 3.19.3—which morphologically was most evident upon synovial hyperplasia and fibrosis. There were no atypical cell forms in this study and no atypical presentation of bone. There is good correlation between clinical score and histological measurements in this study.

PBS Vehicle treatment group: Marked arthropathy was noted in the majority of animals treated with PBS vehicle. The pathology presentation was a widespread—essentially mononuclear cell—synovitis invading the tibio-talus space and spreading towards the superficial facet of the calcaneum.

There was extensive lytic destruction of bone—notably the talus and navicular bones—from both contact synovitis and from pannus expansion into the bone marrow cavities and stromal cavities. Fibrosis of the synovium was common, with occasional fibrinoid deposits, with variable degrees of synovial hyperplasia.

3.19.3 10 mg/kg treatment group: The 3.19.3 treatment group showed a histologically significant reduction in the incidence and severity of all arthropathy lesions, although it was most marked by reduction of synovial hyperplasia and fibrosis; together with a reduction in severity of both articular space and bone marrow localized pannus.

Human IgG isotype control treatment group: Histologically, there were no significant differences between this group and the PBS vehicle group.

Prednisolone 3 mg/kg treatment group: This group showed a marked reduction in the incidence and severity of all arthropathy lesions.

Figure 12A:
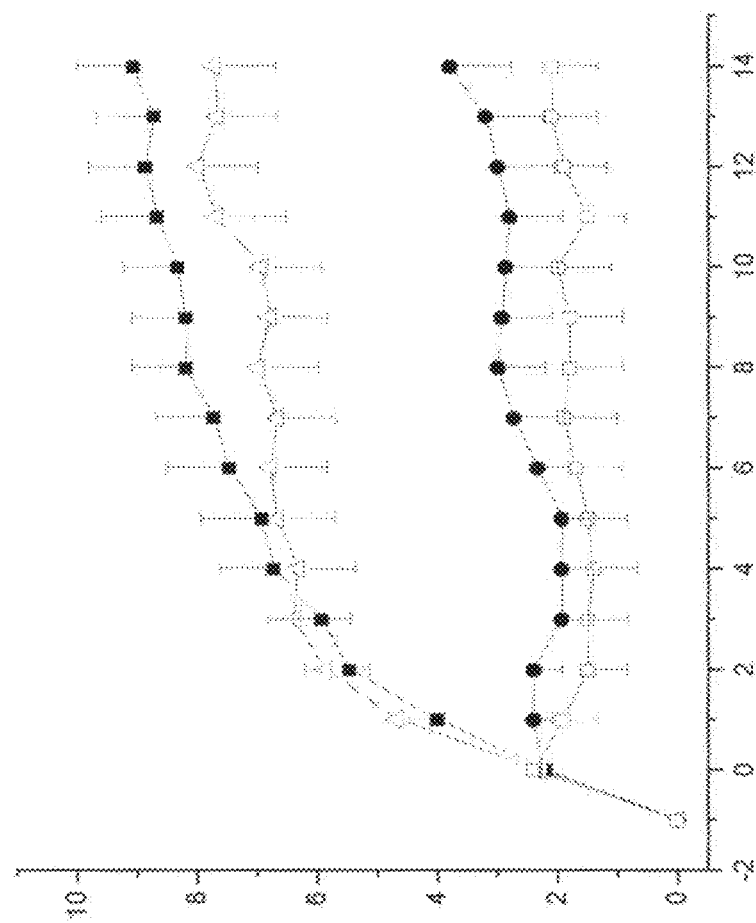
FIG. 12A Effect of 3.19.3 treatment on clinical disease progression in the collagen induced arthritis disease model. Collagen induced arthritis was induced in male DBA/1 mice and animals dosed therapeutically with test treatments.
Figure 12B:
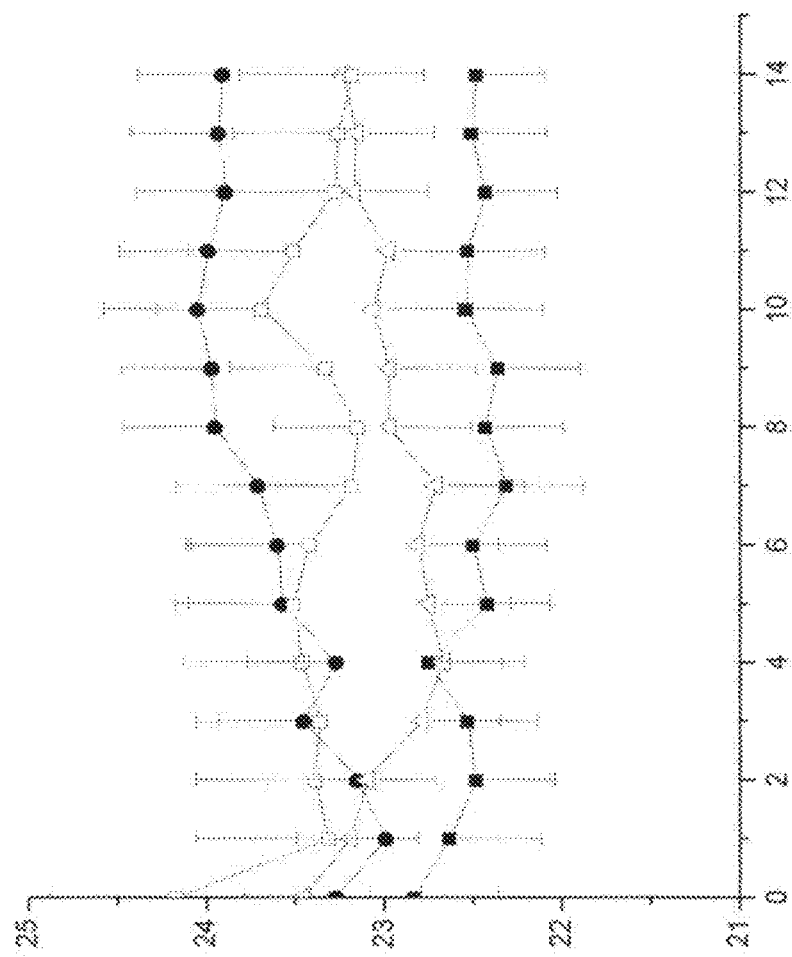
FIG. 12B Effect on mean animal body weights.

Summary: This study demonstrates that neutralization of angiopoietin-2 has been shown to be efficacious in ameliorating collagen-induced arthritis in male dba/1 mice (FIG. 12a) with no significant change in mean body weight observed between each treatment group throughout the period from disease onset, suggesting that 3.19.3 therapy was well tolerated (FIG. 12b). This study assessed efficacy of 3.19.3 at a dose of 10 mg/kg, and demonstrated reductions in both clinical signs of disease progression (arthritic score) and histological assessment of synovitis and joint destruction.

Example 9: Anti-Ang-2 Antibodies Inhibit Retinal Vascularization

The effect of anti-Ang-2 antibodies on retinal vascularization MEDI1/5 antibodies was studied by comparing retinal samples from treated mice versus control treated mice.

Methods: CD1 pups are either left untreated or dosed intraperitoneally with MEDI1/5 (1 mg/kg or 10 mg/kg) at p1, p3 and p5 (p1 being day of birth). At p10, pups were anesthetized with isoflurane and then perfused with 12.5 mg/ml FITC-dextran (Vector Labs). A small slit was made in the cornea and the entire eye was removed from the optic cup before placing into 10% neutral buffered formalin. After 1 hour fixation in formalin, eyes were briefly rinsed in PBS and then placed in a dish of PBS for dissection. Retinas were carefully dissected and cut into a clover leaf formation prior to mounting onto a glass slide with Vectashield (Vector Labs). Images of flatmounts were examined and acquired using fluorescence microscopy (Nikon) with attached digital camera system.

Figure 13A:
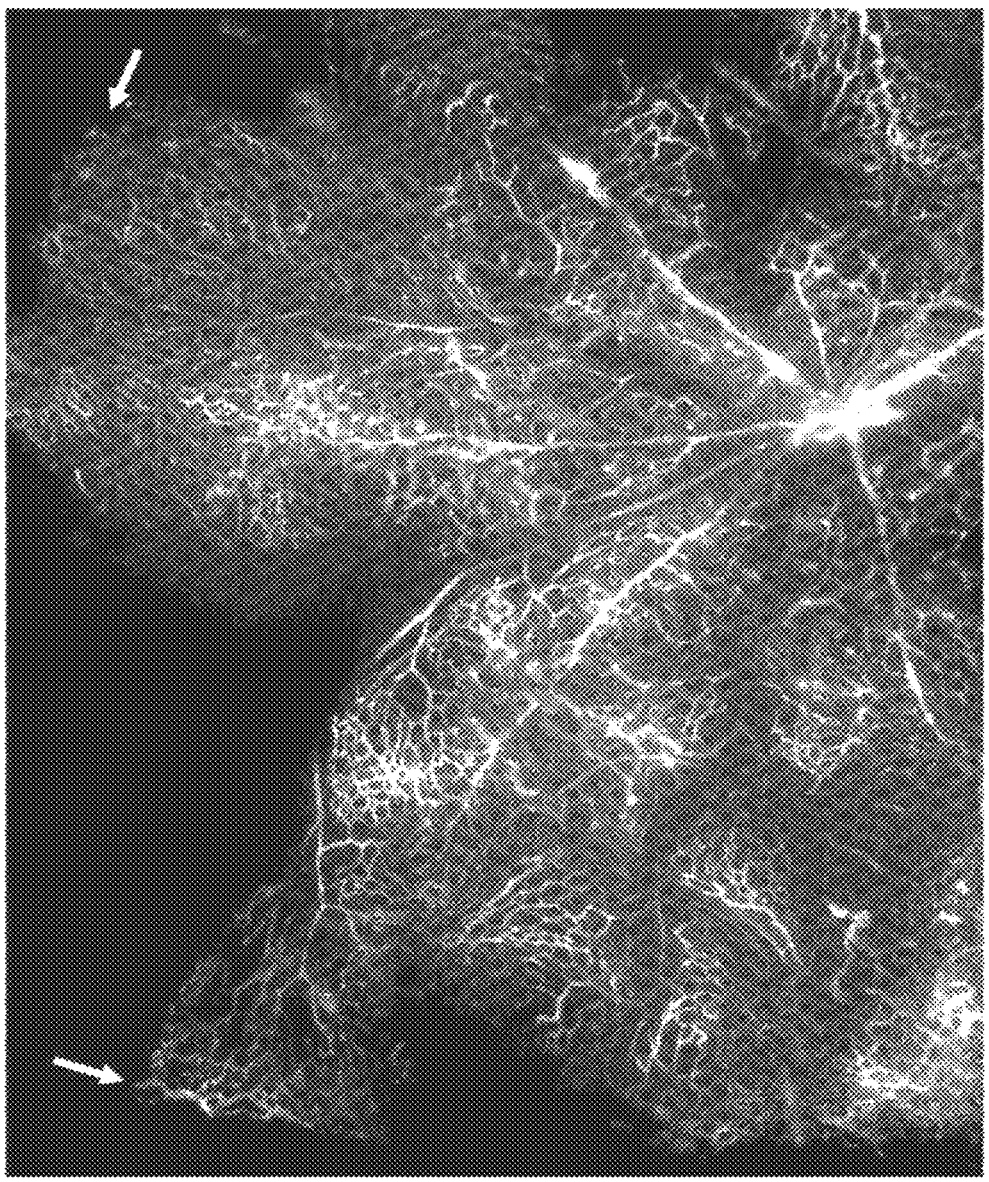
Figure 13C:
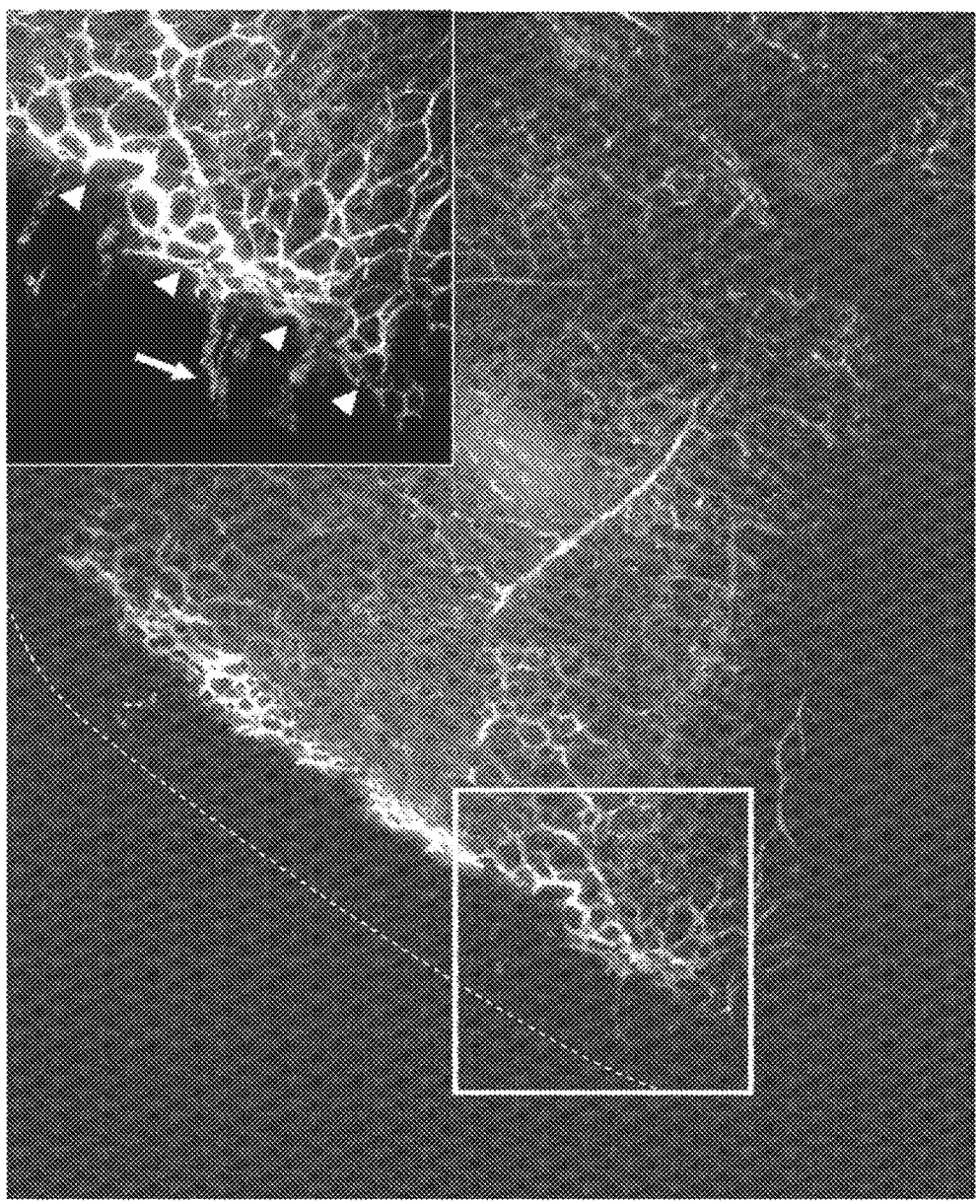
Figure 13D:
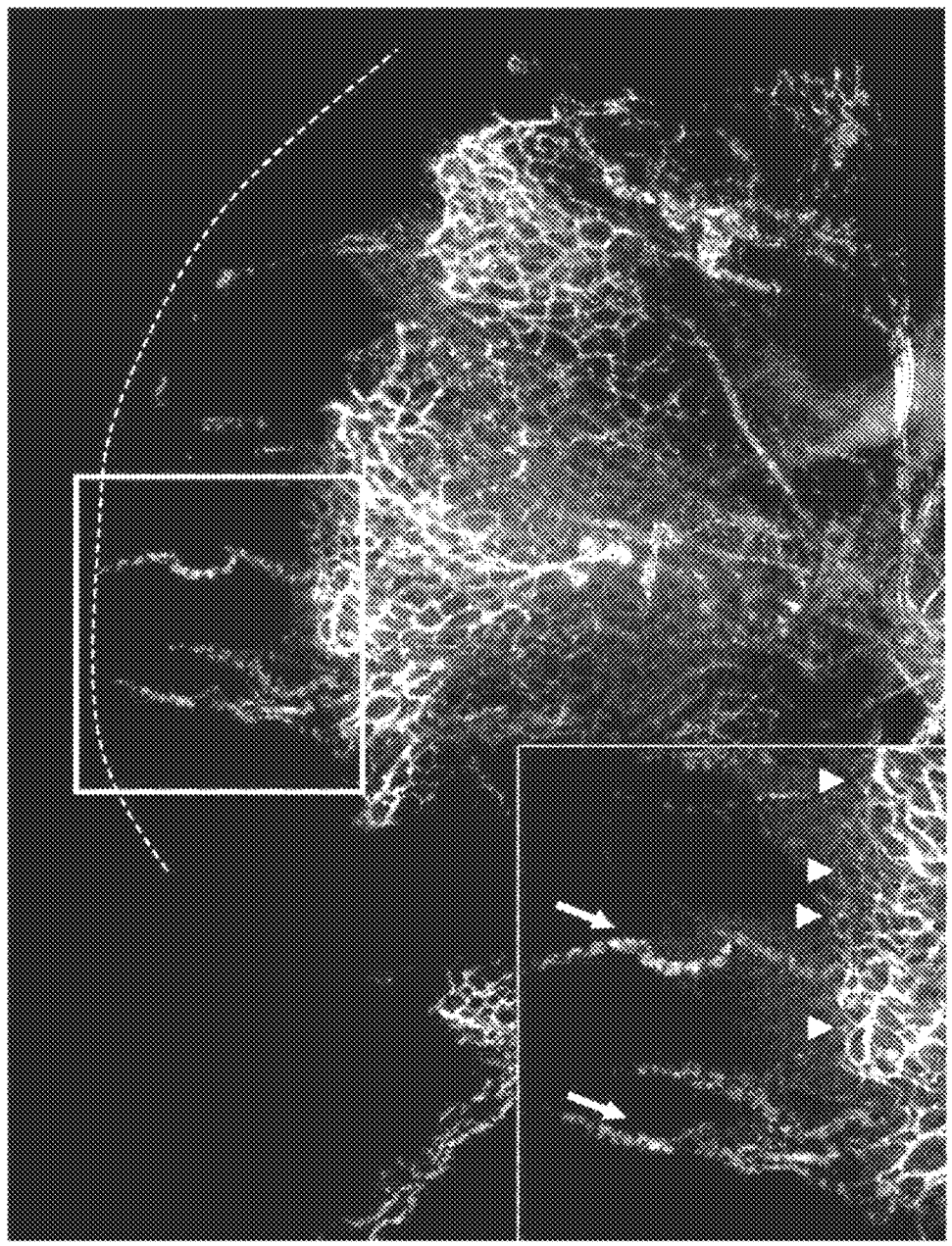

Results: Retina vasculature in untreated pups (FIG. 13a) and those treated with 0.3 mg/kg of MEDI1/5 (FIG. 13b) extend to the outer edge of retina, indicated with white arrow. Upon treatment with increasing dose of MEDI1/5, we see a dose response in the level of inhibition of advancing retina vessels (FIGS. 13c and 13d). The outer rim of retina is demarcated with dotted line and at both doses the hyloid vessels (white arrow) reach the outer rim of the retina but the retina vessels (white arrowheads) in 1 mg/kg MEDI1/5 (FIG. 13c) approach closer to the periphery of the retina in comparison to the 10 mg/kg MEDI1/5 (FIG. 13d) treated group. These results demonstrate a dose-dependent inhibition of retinal angiogenesis by the treatment of MEDI1/5 anti-Ang-2 antibodies.

Example 10. Anti-Ang-2 Antibodies Inhibit FGF-Mediated Angiogenesis

The anti-Ang-2 antibody, MEDI1/5 was evaluated for anti-angiogenic effects in a FGF2 (basic FGF)-induced Matrigel™ plug assay. Recombinant murine FGF2 (mFGF basic; R&D Systems) was pre-mixed with Matrigel™ (reduced growth factor, phenol red-free; Trevigen) at 1 µg/ml. Each 5-6 week old female athymic mouse was subcutaneously implanted with 500 µl of FGF2/Matrigel™ mixture. Antibody MEDI1/5 was administered 10 minutes prior to FGF2/Matrigel™ implantation and continued every three days given intraperitoneal at 1, 10, and 20 mg/kg for a total of 3 doses. The extent of angiogenesis was assessed after 10 days by measuring dextran functioning vessels. Mice were intervenously injected with 100 µl FTC-Dextran (250,000 MW; Sigma) at 25 mg/ml in saline. Twenty minutes post FITC-Dextran injection, mice are humanely euthanized and plugs dissected out. Plugs are then placed in lysing matrix tubes A (MP Biomedicals) containing 1 ml of PBS and homogenized on FastPrep machine (MP Biomedicals) for 60 seconds at 6.0M/S. Samples were then centrifuged at 10,000 rpm for 5 minutes and supernatant collected. 200 µl of each sample (in duplicates) was then placed into a white, clear bottom 96 well plate and FITC output was read on EnVision instrument (Perkin Elmer).

For histology purposes, plugs were harvested and placed into 10% neutral-buffered formalin, processed and then paraffin embedded. The paraffin embedded tissues were then sectioned and stained with hematoxylin and eosin.

Figure 14A:
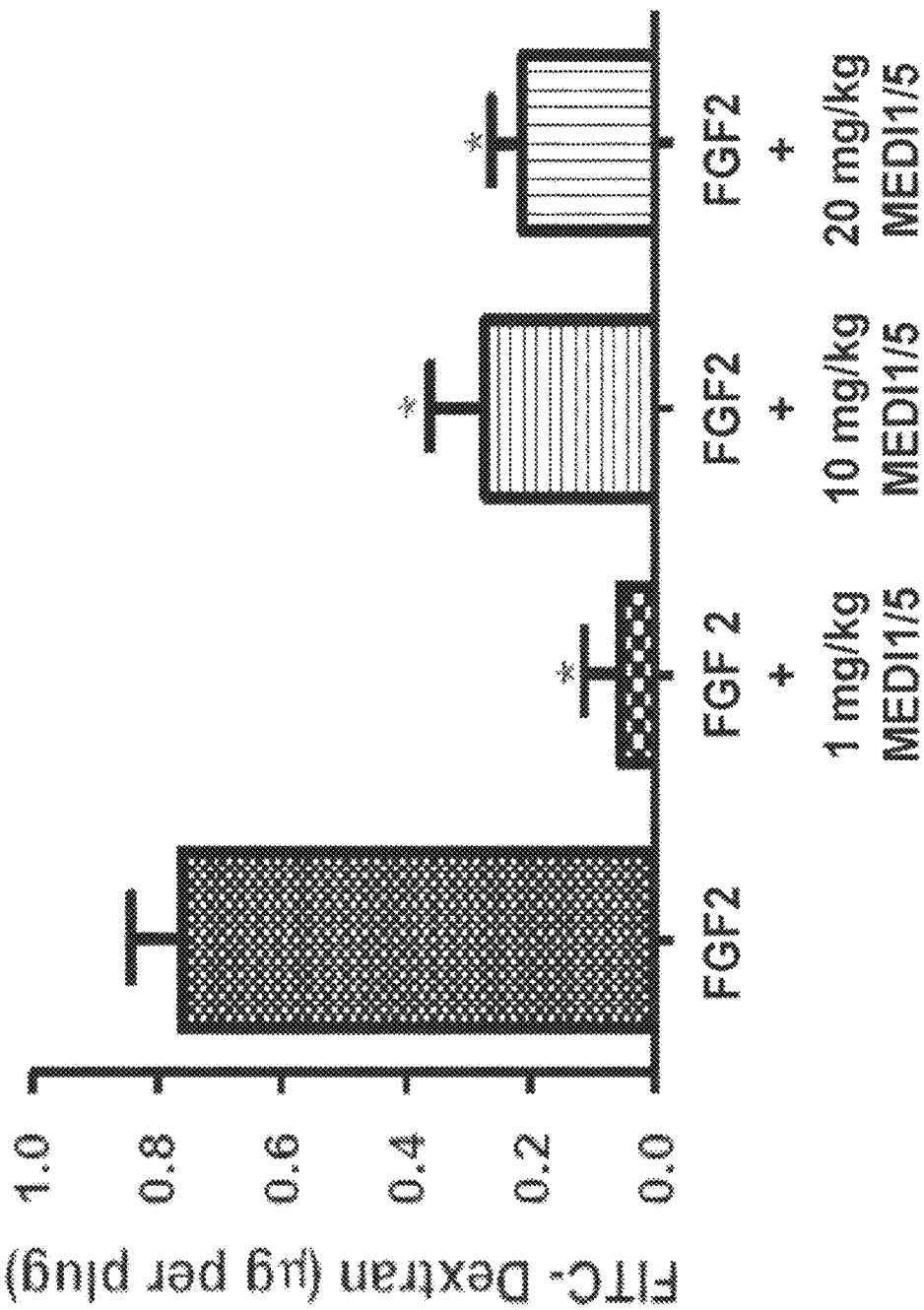
FIG. 14A-C Anti-Ang-2 antibodies inhibit FGF2 mediated angiogenesis.
Figure 14B:
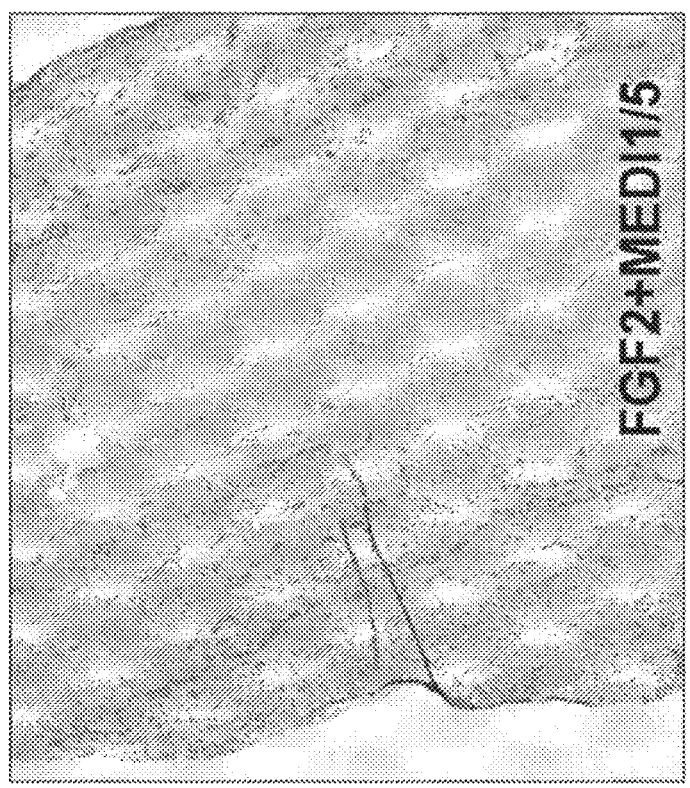
Figure 14C:
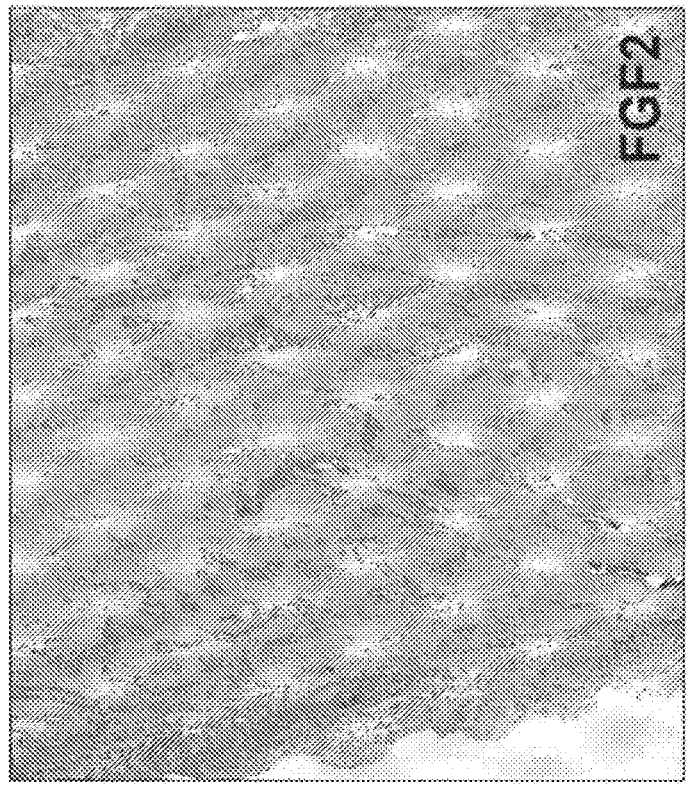

Results: Approximately 0.78 µg of FITC-dextran could be detected in plugs induced with 1 µg/ml of FGF2 (FIG. 14a). On the other hand, when these FGF2-treated plugs were exposed to 3 doses of MEDI1/5, ranging from 1, 10, and 20 mg/kg, the amount of FITC-dextran present in plugs harvested ranged from 0.05-3 µg. This significant reduction in FITC-dextran in MEDI1/5 treated animals suggests that MEDI1/5 inhibits FGF2-induced angiogenesis in the Matrigel™ plugs. Plugs when stained with hematoxylin and eosin (FIG. 14b) reveal that there are fewer vessels in FGF2+ MEDI1/5 plugs compared to FGF2 plugs alone, thus further providing evidence that the anti Ang-2 antibody MEDI1/5 inhibits FGF-mediated angiogenesis.

Example 11. Anti-Ang-2 Antibodies Inhibit Disease Progression in a Mouse Model of Arthritis In this Example, the Anti-Ang-2 antibody 3.19.3 was used in a collagen-induced arthritis (CIA) mouse model in an attempt to demonstrate therapeutic efficacy.

Materials and Methods: To study the effect of treatment on clinical disease progression in the collagen-induced arthritis (CIA) disease model collagen-induced arthritis was induced in male DBA/1 mice and animals dosed therapeutically with test treatments.

Preparation of rat collagen type II emulsion: Bovine Collagen Type II (MD Biosciences) was stored at 4° C. in the dark until use. Prior to immunization of animals, bovine collagen was dissolved in 0.01 M acetic acid at a stock solution of 2 mg/mL and stored overnight in the dark at 4° C. On the day of immunization, collagen was emulsified with equal volume of Freund's Complete Adjuvant (FCA (Difco)) to give a solution at 1 mg/mL.

Induction of arthritis: On day 0, male DBA/1 mice (6-8 weeks old, Harlan Sprague Dawley, UK) were lightly anaesthetized with 3.5% isoflurane and immunized intra-dermal just above the root of the tail with 100 µg rat collagen type II emulsified in FCA (1 mg/mL; 0.1 mL/mouse).

Staphylococcal Enterotoxin B (SEB) booster: On day 21, all mice were anaesthetised as before and given a booster injection of 30 µg SEB (600 µg/ml in water for injections (Toxin Technology) emulsified in an equal volume of Freund's Incomplete Adjuvant (Sigma) to give a final concentration of 300 µg/ml). 50 µl×2 (equivalent to 30 µg SEB) was injected intradermal adjacent to the immunization site.

Assessment of arthritis: Clinical observations regarding welfare of the animals were carried out daily at time of dosing. Observations for clinical signs of disease were carried out daily from day 20 post immunization, whereby the animals were removed from their micro-environment, and scored using the scoring system outlined below.

TABLE 10

Scoring system for hind and forepaws

| Score | Description |
|---|---|
| 0 | Normal |
| 1 | Erythema and slight swelling of one of more toes |
| 2 | Erythema and obvious swelling of two or more toes, or mild swelling of the ankle or wrist without toe involvement |
| 3 | Erythema and obvious swelling to some toes and ankle or fore paw and wrist |
| 4 | Erythema and severe swelling of ankle and digits |

Dosing:
Animals were randomly assigned to treatment groups, as outlined in Table 11 below.

TABLE 11

Treatment groups

| Group | Treatment | No. of animals |
|---|---|---|
| 1 | PBS Vehicle i.p. | 20 |
| 2 | 0.1 mg/kg Antibody 3.19.3 | 20 |
| 3 | 1 mg/kg 3.19.3 i.p. | 20 |
| 4 | 10 mg/kg 3.19.3 i.p. | 20 |
| 5 | Human IgG control i.p. | 20 |
| 6 | Prednisolone 3 mg/kg p.o. | 10 |

Animals in treatment groups 1-5 were therapeutically dosed intraperitoncally (i.p.) with 10 mL/kg every 3 days for 14 days from disease onset (defined as a clinical score of 2 in one or more paws). Purified human IgG (hIgG) was used as a negative isotype control. Animals in treatment group 6 were therapeutically dosed orally (p.o.) with Prednisolone 3 mg/kg daily for 14 days from disease onset (defined as a clinical score of 2 in one or more paws).

Termination: Animals were terminated 14 days post disease onset by exposure to rising concentration of carbon dioxide. Mouse paws were excised post mortem, fixed in 10% buffered formalin and decalcified. Decalcified paws were routinely processed and then embedded in paraffin blocks. Serial sections were cut and stained with hematoxylin and eosin for histologic analysis, as well as CD31 staining for quantitation of microvessel density in the synovium.

Results: Clinical Signs of Disease (Arthritis Score)
FIG. 15A shows the arthritic score mean (+/−standard error of the mean) against days from disease onset (i.e. days of treatment) (open squares=PBS, open triangles=isotype control, closed squares=0.1 mg/kg 3.19.3, closed triangles=1 mg/kg 3.19.3, closed circles-10 mg/kg 3.19.3 and open circles=prednisolone). Dose-dependent reductions in clinical signs of disease progression (arthritic score) and were observed. There was a significant reduction at doses of 1 and 10 mg/kg. Area under the curve (AUC) for clinical disease progression was calculated for each animal from disease onset (FIG. 15B), Table 12. Unless otherwise stated, statistical analysis was by one-way ANOVA with Dunnett's post-hoc comparison to vehicle controls. P<0.05 was considered to be statistically significant throughout the study.

TABLE 12

AUC of Clinical Score of CIA mice treated with 3.19.3

| Treatment | AUC | % inhibition |
|---|---|---|
| PBS Vehicle ip | 118 +/− 10 | |
| Human IgG 10 mg/kg ip | 102 +/− 13 | 12% +/− 11% |
| 3.19.3 0.1 mg/kg ip | 99 +/− 15 | 16% +/− 13% |
| 3.19.3 1 mg/kg ip | 46 +/− 9 | 53% +/− 7%* |
| 3.19.3 10 mg/kg ip | 67 +/− 11 | 44% +/− 9%* |
| Prednisolone 3 mg/kg po | 41 +/− 08 | 78% +/− 7%* |

*= P < 0.05 ANOVA - one way, post hoc Dunnets v. vehicle

Histolopathological evaluation of CIA model treatment groups: Results showed evidence of a dose-dependent anti-arthritic effect following administration of 3.19.3 on all parameters evaluated including synovial hyperplasmia (FIG. 15 C), synovitis (FIG. 15 D), pannus (FIG. 15 E), synovial fibrosis (FIG. 15F), and periostitis (FIG. 15G). Histologically, there were no significant differences between the isotype control-treated group and the PBS vehicle group (FIGS. 15C-G).

Figure 15H:
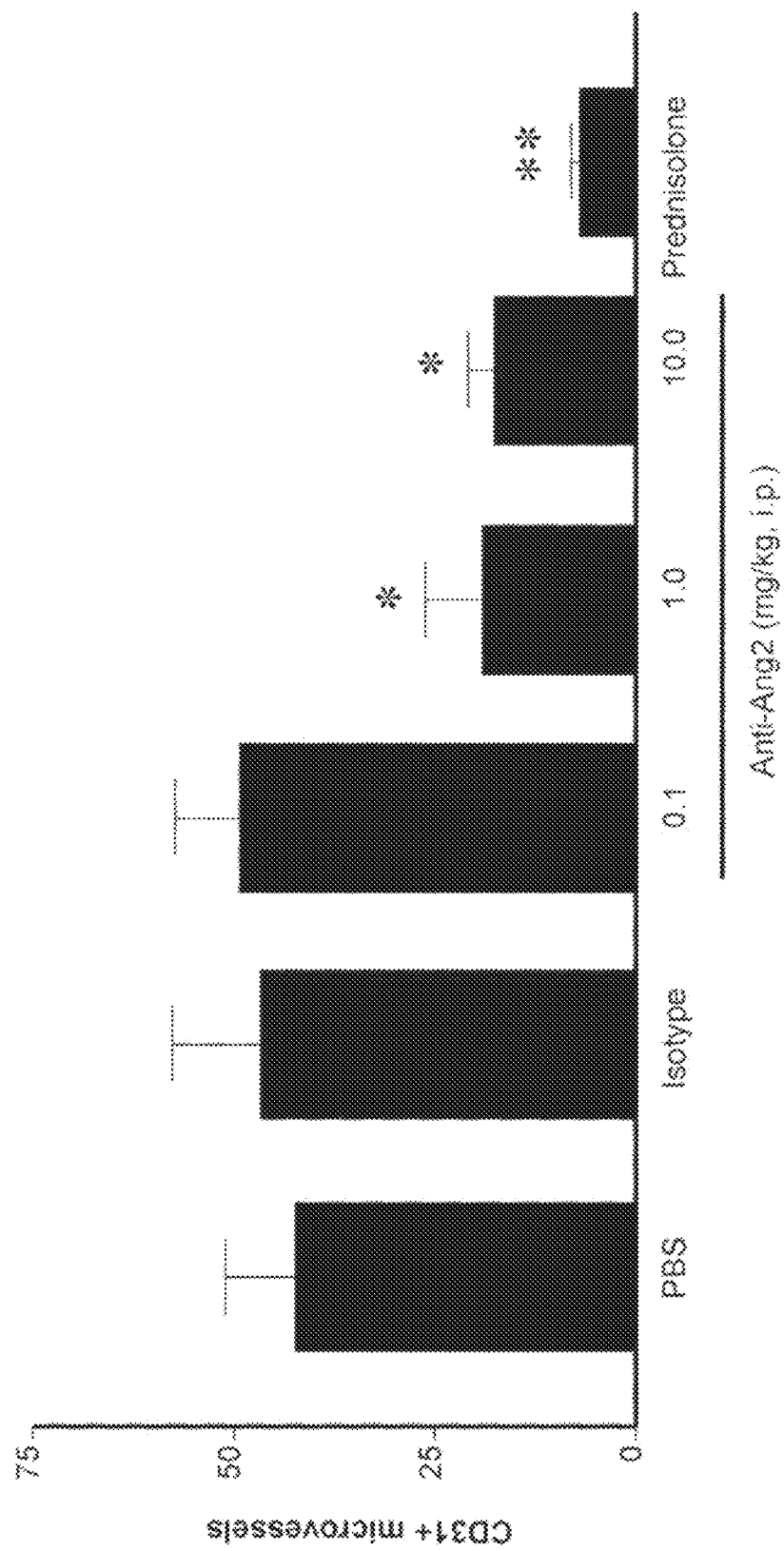

Immunohistological evaluation of CD31+ (microvessel density) in synovium: Results showed significant reduction in microvessel density in the synovium at doses of 1 and 10 mg/kg as well as with prednisolone. There was no effect with 0.1 mg/kg 3.19.3 treatment (FIG. 15H).

Overall Conclusions: This study demonstrates that neutralization of angiopoietin-2 is efficacious in ameliorating collagen-induced arthritis in male DBA/1 mice. This study assessed efficacy of 3.19.3 at a dose of 0.1, 1 and 10 mg/kg, and demonstrated dose-dependent reductions in both clinical signs of disease progression (arthritic score) and histological assessment of synovitis and joint destruction, as well as microvessel density in the synovium. The prednisolone-treated group showed a marked reduction in the incidence and severity of all measures.

Example 12: Anti-Ang-2 Antibodies+Anti-TNFα Agents in Combination are Effective in a Prophylactic Model of Arthritis In the Example, the anti-Ang-2 antibody MEDI1/5 as a standalone agent or in combination with the anti-TNFα agent ENBREL® was studied in a prophylactic model of arthritis. More specifically, the effect the MEDI1/5 antibody+/−ENBREL® on the clinical disease progression in the glucose 6 phosphate isomerase (G6PI) arthritis disease model.

Materials and Methods
Preparation of G6PI emulsion: On the day of immunization, FCA (Freund's complete adjuvant) was prepared by grinding M. tuberculosis (Difco) into IFA (Chondrex) to make a 1 mg/mL stock. Human G6PI was set to a concentration of 3 mg/mL in phosphate buffered saline (Gibco). G6PI was emulsified, by sonication, with equal volume of FCA to give an emulsion of 1.5 mg/mL.

Induction of arthritis: On day 0, male DBA/1J mice (9-10 week old, Jackson Laboratories) were administered 0.2 mL (300 µg G6PI) over two sites at the base of the tail via subcutaneous injections.

Assessment of arthritis: Observations for clinical signs of disease were carried out daily from day 0 post immunization, whereby the animals were removed from their microenvironment, and scored using the scoring system outlined in Table 13 below.

TABLE 13

Scoring system for hind and forepaws

| Score | Description |
|---|---|
| 0 | Normal |
| 0.5 | Eruthema and slight swelling |
| 1 | Swelling of digits only |
| 1.5 | Local mild/moderate swelling |
| 2 | Severe local swelling of major joint |
| 2.5 | Severe local swelling of major joint and other |
| 3 | Severe swelling of entire paw |
| 3.5 | Severe swelling and partial or total ankylosis |

Dosing: Animals were randomly assigned to treatment groups, as outlined in Table 14 below.

TABLE 14

Treatment groups

| Group | Treatment | No. of animals |
|---|---|---|
| 1 | 10 mg/kg Human IgG1 control antibody i.p. | 8 |
| 2 | 10 mg/kg MEDI1/5 i.p. | 8 |
| 3 | 1 mg/kg ENBREL ® i.p. | 8 |
| 4 | 4 mg/kg ENBREL ® i.p. | 8 |
| 5 | 10 mg/kg MEDI1/5 i.p + 1 mg/kg ENBREL ® i.p. | 8 |
| 6 | 10 mg/kg MEDI1/5 i.p + 1 mg/kg ENBREL ® i.p. | 8 |

Animals in the enbrel treatment group were dosed daily with 10 mL/kg from days 0-9, then every 3 days until termination on day 16. All other treatments were administered every 3 days.

Termination: Animals were terminated 16 days post immunization by exposure to rising concentration of carbon dioxide. Mouse paws were excised post mortem, fixed in 10% buffered formalin, assessed for bone mineral density and then decalcified. Decalcified paws were routinely processed and then embedded in paraffin blocks. Serial sections were cut and stained with hematoxylin and cosin for histologic analysis. The histological analysis was scored by the following schedule:

Total joint scores
  Both hind knee and ankle joints scored for:
    Inflammation
    Bone damage
    Pannus formation
    Cartilage damage
  Score of 0-5
    0=normal
    1=minimal
    2=mild
    3=moderate
    4=marked
    5=severe
Bone Mineral Density Bone mineral density was assessed in the stifle joint of the hind limbs using DEXA imaging (GE Piximus). Following collection, hind limbs were placed in 10% neutral buffered saline for 4 days. Just prior to imaging, limbs were placed in 70% ethanol, then allowed to dry.

Results:

Reductions in clinical signs of disease progression (arthritic score) (FIG. 16A (closed circles=isotype control, closed diamond=10 mg/kg MEDI1/5, open diamond=1 mg/kg etanercept, grey diamond=combination of 10 mg/kg MEDI1/5 with 1 mg/kg etanercept, open square=4 mg/kg enbrel, grey square=combination of 10 mg/kg MEDI1/5 with 4 mg/kg etanercept) and 16B) were observed with either etanercept or MEDI1/5 treatment. There was a further reduction in clinical score when MEDI1/5 was administered in combination with the lower dose of etanercept (One-Way ANOVA with Dunnett's post-hoc comparison to isotype control). All joints in the isotype control antibody treated animals showed evidence of disease, whereas MEDI1/5 or 1 mg/kg etanercept treatments resulted in 31% or 22% of the joints showing no signs of disease, respectively. When the 10 mg/kg MEDI1/5 and 1 mg/kg etanercept were administered in combination, 50% of the joints of the animals in this group were disease free, comparable to the level of protection provided by the high dose (4 mg/kg) of enbrel (53%) (Table 15). Histological assessment of synovitis and joint destruction (FIG. 16C) supported the clinical score results as did the protection from loss of bone mineral density (FIG. 16D).

TABLE 15

Disease free joints observed in MEDI1/5 treated arthritic mice

| Treatment | % Disease free joints |
|---|---|
| 10 mg/ml Isotype control | 0% |
| 10 mg/kg MEDI1/5 | 31% |
| 1 mg/kg etanercept | 22% |
| 10 mg/kg MEDI1/5 + 1 mg/kg etanercept | 50% |
| 4 mg/kg etanercept | 53% |
| 10 mg/kg MEDI1/5 + 1 mg/kg etanercept | 56% |

Conclusions:

This study demonstrates that neutralization of angiopoietin-2 is efficacious in inhibiting the development of G6PI-induced arthritis in male DBA/1J mice comparable to the anti-TNF comparator, etanercept. This study also assessed efficacy of MEDI1/5 combined with etanercept and demonstrated that combination treatment with the lower dose of enbrel provides further efficacy in both clinical signs of disease progression (arthritic score) and histological assessment of synovitis and joint destruction, as well as loss of bone mineral density, when administered prior to onset of disease.

Example 13: Anti-Ang-2 Antibodies+Anti-TNFα Agents in Combination are Effective in a Therapeutic Model of Arthritis The effect of treatment with MEDI 1/5 with or without etanercept was evaluated following onset of clinical disease in the glucose 6 phosphate isomerase (G6PI) arthritis disease model. G6PI-induced arthritis was induced in male DBA/1J mice and animals dosed therapeutically with test treatments.

Materials and Methods: The mice in this study were prepared similarly as presented in Example 12.

Dosing: This was a rolling admissions study: once an animal reached a clinical score of 3.5 to 5.0, it was randomly assigned to treatment groups (as outlined below) and dosing began. The day of initial dosing became study day 0 for that animal. Treatment groups were similar to those presented in Example 12.

Termination: Study was terminated 12 days post treatment initiation. No further endpoints were assessed on these animals.

Results: When administered in a therapeutic approach following the onset of clinical disease, modest reductions in clinical signs of disease progression (arthritic score) were observed with MEDI1/5 treatment, while both doses of etanercept tested had no effect on disease progression. There was a more dramatic inhibition of progression of disease when MEDI1/5 (10 mg/kg) was administered in combination with the higher dose of etanercept (4 mg/kg) (FIG. 17A (closed circles=isotype control, closed diamond=MEDI1/5, open diamond=1 mg/kg etanercept, grey diamond=combination of MEDI1/5 with 1 mg/kg etanercept, open square=4 mg/kg etanercept, grey square=combination of MEDI1/5 with 4 mg/kg etanercept).

Conclusions: This study demonstrates that neutralization of angiopoietin-2 is efficacious in ameliorating G6PI-induced arthritis in male DBA/1 mice comparable to the anti-TNF comparator, etanercept, when administered following the onset of clinical signs of disease. This study also assessed efficacy of MEDI1/5 combined with etanercept and demonstrated that combination treatment provides enhanced efficacy over either agent alone.

We claim:

1. An isolated antibody that binds to angiopoietin-2 (Ang-2), wherein the antibody comprises a heavy chain variable region of SEQ ID No:7 (MEDI5) and a light chain variable region selected from the group consisting of:
   a) SEQ ID No:3 (MEDI1);
   b) SEQ ID No:4 (MEDI2);
   c) SEQ ID No:5 (MEDI3);
   d) SEQ ID No:6 (MEDI4); and
   e) SEQ ID No:8 (MEDI6);
   wherein the antibody is a full-length antibody or fragment thereof.

2. The antibody according to claim 1, wherein the antibody comprises a light chain variable region of SEQ ID No:3 (MEDI1).

3. The antibody according to claim 1, wherein the antibody, when produced, exhibits a production efficiency in a mammalian host cell equal to or greater than 2 times the production efficiency of an Ang-2 antibody comprising SEQ ID No: 1 and SEQ ID No: 2 (3.19.3).

4. The antibody according to claim 1, wherein the antibody exhibits an aggregation rate that is at least 10% lower than the aggregation rate of an Ang-2 antibody comprising SEQ ID No: 1 and SEQ ID No: 2 (3.19.3).

5. The antibody according to claim 1, wherein the antibody exhibits a melting temperature that is higher than the melting temperature of an Ang-2 antibody comprising SEQ ID No: 1 and SEQ ID No: 2 (3.19.3).

6. A pharmaceutical composition comprising: an isolated antibody according to claim 1, wherein the antibody comprises a light chain variable region of SEQ ID No:3 (MEDI1) and a heavy chain variable region of SEQ ID No:7 (MEDI5); and an excipient.

7. A method of inhibiting angiogenesis of a cancer tumor in an human in need thereof, wherein the method comprises administering to the human a composition comprising: an isolated antibody of claim 1; and an excipient.

8. The method according to claim 7, wherein the composition further comprises one or more other cancer therapeutic agents.

9. The method according to claim 7, wherein the cancer is selected from the group consisting of melanoma, colon, colorectal, lung, small cell lung carcinoma, non-small cell lung carcinoma, breast, rectum, stomach, glioma, prostate, ovary, testes, thyroid, kidney, liver, hepatocellular carcinoma pancreas, brain, neck, glioblastoma, endometrial cancer, and central nervous system cancer.

10. The method according to claim 7, wherein the composition is administered intravenously, subcutaneously, intratumorally, intramuscularly, parenterally, or orally.

11. A method of treating arthritis in a human in need thereof, wherein the method comprises administering a composition comprising: an isolated antibody of claim 1; and an excipient.

12. The method according to claim 11, wherein the method further comprises administering one or more anti-inflammatory therapeutic agents.

13. The method according to claim 12, wherein the anti-inflammatory therapeutic agent is a TNF-α antagonist.

14. The antibody according to claim 1, wherein the antibody is a full-length antibody.

15. The antibody according to claim 1, wherein the antibody is an antibody fragment.

* * * * *

SEQUENCE LISTING

```
<160> NUMBER OF SEQ ID NOS: 8

<210> SEQ ID NO 1
<211> LENGTH: 215
<212> TYPE: PRT
<213> ORGANISM: Artificial
<220> FEATURE:
<223> OTHER INFORMATION: synthetic construct

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Cys Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 2
<211> LENGTH: 123
<212> TYPE: PRT
<213> ORGANISM: Artificial
<220> FEATURE:
<223> OTHER INFORMATION: Synthetic construct

<400> SEQUENCE: 2
```

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Gly Met His Trp Gly Arg Gln Ala Pro Gly Lys Gly Leu Glu Trp Val
        35                  40                  45

Ala Val Ile Ser His Asp Gly Asn Asn Lys Tyr Tyr Val Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Asp Phe Trp Ser Gly Leu Asn Trp Phe Asp Pro
            100                 105                 110

Trp Gly Gln Gly Thr Leu Val Thr Val Ser Ser
        115                 120
```

```
<210> SEQ ID NO 3
<211> LENGTH: 215
<212> TYPE: PRT
<213> ORGANISM: Artificial
<220> FEATURE:
<223> OTHER INFORMATION: Synthetic construct

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Thr Gly Ala Ser Ser Trp Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 4
```

```
<211> LENGTH: 215
<212> TYPE: PRT
<213> ORGANISM: Artificial
<220> FEATURE:
<223> OTHER INFORMATION: Synthetic construct

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Asn Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 5
<211> LENGTH: 215
<212> TYPE: PRT
<213> ORGANISM: Artificial
<220> FEATURE:
<223> OTHER INFORMATION: Synthetic construct

<400> SEQUENCE: 5

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Asp Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110
```

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 6
<211> LENGTH: 215
<212> TYPE: PRT
<213> ORGANISM: Artificial
<220> FEATURE:
<223> OTHER INFORMATION: Synthetic construct

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
                20                  25                  30

Tyr Leu Ala Trp Tyr Gln Gln Lys Pro Gly Gln Ala Pro Arg Leu Leu
            35                  40                  45

Ile Ala Gly Ala Ser Ser Trp Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210                 215

<210> SEQ ID NO 7
<211> LENGTH: 123
<212> TYPE: PRT
<213> ORGANISM: Artificial
<220> FEATURE:
<223> OTHER INFORMATION: Synthetic construct

```
<400> SEQUENCE: 7

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Thr Asn Tyr
            20                  25                  30

Gly Met His Trp Val Arg Gln Ala Pro Gly Lys Gly Leu Glu Trp Val
            35                  40                  45

Ala Val Ile Ser His Asp Gly Asn Asn Lys Tyr Tyr Val Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Asp Phe Trp Ser Gly Leu Asn Trp Phe Asp Pro
            100                 105                 110

Trp Gly Gln Gly Thr Leu Val Thr Val Ser Ser
            115                 120

<210> SEQ ID NO 8
<211> LENGTH: 215
<212> TYPE: PRT
<213> ORGANISM: Artificial
<220> FEATURE:
<223> OTHER INFORMATION: Synthetic construct

<400> SEQUENCE: 8

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
            35                  40                  45

Ile Thr Gly Ala Ser Ser Trp Ala Thr Gly Ile Ala Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215
```